US006872704B2

(12) United States Patent
Kelly et al.

(10) Patent No.: US 6,872,704 B2
(45) Date of Patent: Mar. 29, 2005

(54) ACIDIC MAMMALIAN PROTEINS AND POLYNUCLEOTIDES ENCODING THE SAME

(75) Inventors: Karen M. Kelly, Branford, CT (US); David A. Lewin, New Haven, CT (US); Timothy A. Stewart, San Francisco, CA (US)

(73) Assignees: Genentech, Inc., South San Francisco, CA (US); Curagen Corporation, New Haven, CT (US)

( * ) Notice: Subject to any disclaimer, the term of this patent is extended or adjusted under 35 U.S.C. 154(b) by 0 days.

(21) Appl. No.: 10/268,919

(22) Filed: Oct. 9, 2002

(65) Prior Publication Data

US 2003/0203375 A1 Oct. 30, 2003

Related U.S. Application Data

(60) Provisional application No. 60/327,902, filed on Oct. 9, 2001.

(51) Int. Cl.[7] .............................................. A61K 38/00
(52) U.S. Cl. .............................. 514/12; 514/2; 514/12; 514/21; 530/300; 530/324
(58) Field of Search .............................. 514/2, 12, 21; 530/300, 324

(56) References Cited

U.S. PATENT DOCUMENTS

| | | |
|---|---|---|
| 4,469,863 A | 9/1984 | Ts'o et al. |
| 5,023,243 A | 6/1991 | Tullis |
| 5,130,302 A | 7/1992 | Spielvogel et al. |
| 5,177,198 A | 1/1993 | Spielvogel et al. |
| 5,223,618 A | 6/1993 | Cook et al. |
| 5,256,775 A | 10/1993 | Froehler |
| 5,264,562 A | 11/1993 | Matteucci |
| 5,264,564 A | 11/1993 | Matteucci |
| 5,366,878 A | 11/1994 | Pederson et al. |
| 5,378,825 A | 1/1995 | Cook et al. |
| 5,386,023 A | 1/1995 | Sanghvi et al. |
| 5,476,925 A | 12/1995 | Letsinger et al. |
| 5,489,677 A | 2/1996 | Sanghvi et al. |
| 5,508,270 A | 4/1996 | Baxter et al. |
| 5,539,082 A | 7/1996 | Nielsen et al. |
| 5,602,240 A | 2/1997 | De Mesmaeker et al. |
| 5,610,289 A | 3/1997 | Cook et al. |
| 5,623,068 A | 4/1997 | Reddy et al. |
| 5,700,923 A | 12/1997 | Goodchild et al. |
| 5,719,262 A | 2/1998 | Buchardt et al. |

FOREIGN PATENT DOCUMENTS

| | | | |
|---|---|---|---|
| WO | WO 94/17093 A1 | 8/1994 | |
| WO | WO 01/23430 A2 | 4/2001 | |
| WO | WO 01/36633 A1 | 5/2001 | |

OTHER PUBLICATIONS

Boot et al. 2001, J. of Biol. Chem. vol. 276, No. 9, pp. 6770–6778.*

Aron, D., J. Fingling, and J. Tyrrell. 1997. Hypothalamus and pituitary. In Basic & clinical endocrinology/ F. Greenspan and G. Strewler, editors. Appleton & Lang, Stamford. 95–156.

Beck, B. 2001. KO's and organization of peptidergic feeding mechanisms. *Neurosci Biobehav Rev.* 25:143–58.

Bolivar, F., Rodriguez, R.L. Greene, P.J., Betlach, M.C., Heyneker, H.L. and Bayer, H.W. (1977) Construction and characterization of new cloning vehicles. II. A multipurpose cloning system. *Gene* 2:95–113.

Boot, R.G., E.F.C. Blommaart, E. Swart, K. Ghauharali–van der Vlugt, N. Bijl. C. Moe, A. Place, and J.M.F.G. Aerts. 2001. Identification of a Novel Acidic Mammalian Chitinase Distinct from Chitotriosidase. *J. Biol. Chem.* 276(9):6770–6778.

Boot, R.G., Renkema, G.H., Stryland, A., van Zonneveld, A.J. and Aerts, J.M. (1995). Cloning of cDNA encoding chitotriosidases, a human chitonase produced by macrophages. *J. Biol. Chem.* 270:26252–26256.

Cancela, J.M. 2001. Specific Ca2+ signaling evoked by cholecystokinin and acetylcholine: the roles of NAADP, cADPR, and IP3. *Annu Rev Physiol.* 63:99–117.

Clement, K., C. Vaisse, N. Lahlou, S. Cabrol, et al. 1998. A mutation in the human leptin receptor gene causes obesity and pituitary dysfunction. *Nature.* 392:398–401.

Comuzzie, A.G., and D.B. Allison. 1998. The search for human obesity genes. *Science.* 280:1374–7.

Fusetti, F., H. von Moeller, Houston, D., Rozeboom, H.J., et al., Jul. 12, 2002. Structure of human chitotriosidase. Implications for specific inhibitor design and function of mammalian chitinase–like lectins. *J. Biol. Chem.*, 277(28):25537–44.

Giraldo, P., Cenarro, A., Alfonso, P., Perez–Calvo, J.I., Rubio–Felix, D., Giralt, M. and Pocovi, M. (2001) Chitotriosidase genotype and plasma activity in patients type 1 Gaucher's disease and their relatives (carriers and non–carriers). *Haematologica* 86:977–984.

Guan, X.M., H. Yu, and L.H. Van der Ploeg. 1998. Evidence of altered hypothalamic pro–opiomelanocortin/neuropeptide Y mRNA expression in tubby mice. *Brain Res Mol Brain Res.* 59:273–9.

(Continued)

*Primary Examiner*—Christopher R. Tate
*Assistant Examiner*—B. Dell Chism
(74) *Attorney, Agent, or Firm*—Merchant & Gould P.C.

(57) ABSTRACT

Genes are disclosed that are differentially-regulated during feeding and fasting cycles. These genes, and their encoded polypeptides are useful to combat obesity and other metabolic disorders.

8 Claims, 1 Drawing Sheet

OTHER PUBLICATIONS

Hill, J.O., and J.C. Peters. 1998. Environmental contributions to the obesity epidemic. *Science.* 280:1371–4.

Hollack, C.E., van Weely, S., van Oeis, M.H. and Aerts. J.M. (1994) Marked evelation of plasma chitotriosidase activity. A novel hallmark of Gaucher disease. *J. Clin. Invest.* 93:1288–1292.

Kersten, S. 2001. Mechanisms of nutritional and hormonal regulation of lipogenesis. *EMBO Rep.* 2:282–6.

Montague, C.T., I.S. Farooqi, J.P. Whitehead, M.A. Soos, et al. 1997. Congenital leptin deficiency is associated with severe early–onset obesity in humans. *Nature.* 387:903–8.

Nakazato, M., N. Murakami, Y.Date, M. Kojima, et al. 2001. A role for ghrelin in the central regulation of feeding. *Nature.* 409:194–8.

Norman, R.A., C. Boigardus, and E. Ravussin. 1995. Linkage between obesity and a marker near the tumor necrosis factor–alpha locus in Pima Indians. *J Clin Invest.* 96:158–62.

Owhashi, M., H. Arita, and N. Hayai. 2000. Identification of a Novel Eosinophil Chemotactic Cytokine (ECF–L) as a Chitinase Family Protein. *J. Biol. Chem.* 275(2):1279–1286.

Peptide Nucleic Acids (PNA): Synthesis, Properties and Potential Applications. *Bioorganic and Medicinal Chemistry* 4:5–23 (1996).

Phillips, M.S., Q. Liu, H.A. Hammond, V. Dugan, et al. 1996. Leptin receptor missense mutation in the fatty Zucker rat. *Nat Genet.* 13:18–9.

Renkema, G.H., Boot, R.G., Muysers, P.O., Donker–Koopman, W.E. and Aerts, J.M. (1995). Purification and characterizations of human chitotriosidase, a novel member of the chitanase family of proteins. *J. Biol. Chem.* 270:2198–2202.

Ruppert, S., Wang, E.H. and Tjian, R. (1993) Cloning and expression of human TAFII250: a TBP–associated factor implicated in cell–cycle regulats. *Nature.* 362:175–179.

Sakurai, T., A. Amemiya, M. Ishii, I. Matsuzaki, et al. 1998. Orexins and orexin receptors: a family of hypothalamic neuropeptides and G protein–coupled receptors that regulate feeding behavior. *Cell.* 92:573–85.

Sakurai, T., A. Amemiya, M. Ishii, I. Matsuzaki, et al. 1998. Orexins and orexin receptors: a family of hypothalamic neuropeptides and G. protein–coupled receptors that regulate feeding behavior. *Cell.* 92:1 page following 696.

Schrauwen, P., K. Walder, and E. Ravussin. 1999. Human uncoupling proteins and obesity. *Obes Res.* 7:97–105.

Shimkets, R.A., D.G. Lowe, J.T. Tai, P. Sehl, et al. 1999. Gene expression analysis by transcript profiling coupled to a gene database query. *Nat Biotechnol.* 17:798–803.

Sompayrac, L.M. & Darma, K.J. (1981) Efficient infections of monkey cells with DNA of simian virus 40. *Proc. Natl Acad Sci USA* 78:7575–7578.

Spiegelman, B.M., and J.S. Flier. 1996. Adipogenesis and obesity: rounding out the big picture. *Cell.* 87:377–89.

Strosberg, A. D. 1997. Structure and function of the beta 3–adrenergic receptor. *Annu Rev Pharmacol Toxicol.* 37:421–50.

Suziki, M., W. Fugimoto, Goto, M., et al., Aug. 2002 Cellular expression of gut chitinase mRNA in the gastrointestinal tract of mice and chickens. *J. Histochem. Cytochem,* 50(8):1081–9.

Weigle, D.S., and J.L. Kuijper. 1996. Obesity genes and the regulation of body fat content. *Bioessays.* 18:867–74.

Wikberg, J.E., R. Muceniece, I. Mandrika, P. Prusis, et al. 2000. New aspects on the melanocortins and their receptors. *Pharmacol Res.* 42:393–420.

Yaswen, L., N. Diehl, M.B. Brennan, and U. Hochgeschwender. 1999. Obesity in the mouse model of pro–opiomelanocortin deficiency responds to peripheral melanocortin. *Nat Med.* 5:1066–70.

Young, E., C. Chatterton, Vellodi, A., and Winchester, B., Aug. 1997. Plasma chitotriosidase activity in Gaucher disease patients who have been treated either by bone marrow transplantation or by enzyme replacement therapy with alglucerase. *J. Inherit. Metab. Dis.*, 20(4):595–602.

Boot, R.G., et al. Accession No. AAG60018.

Boot, R.G., et al., Accession No. AAG60019.

Boot, R.G., et al., Accession No. AF290003.

Boot, R.B., et al., Accession No. AF290004.

Saito, A., et al. Accession No. NM_021797.

Strasberg, R. Accession No. BC011134.

* cited by examiner

ACIDIC MAMMALIAN PROTEINS AND POLYNUCLEOTIDES ENCODING THE SAME

RELATED APPLICATIONS

This application claims priority to U.S. provisional application Ser. No. 60/327,902 filed Oct. 9, 2001, which is incorporated herein by reference in its entirety.

BACKGROUND

Metabolic Disorders

Millions of people throughout the world are affected daily by metabolic disorders such as obesity, anorexia, cachexia, and diabetes. Though the causes for these disorders are as varied as the disorders themselves, many candidate genes and gene products, such as insulin, leptin, and ghrelin, have been identified as potential drug targets for treatment of these disorders. However, these disorders have yet to be conquered.

Obesity, Anorexia, Cachexia, and Diabetes

Understanding metabolic disorders has been hampered by the absence of an animal model that immediately reflects the human situation. Human metabolic disorders do not generally follow a Mendelian inheritance pattern, wherein a single gene determines a metabolic disorder phenotype (physical manifestation of a gene's expression; Weigle and Kuijper, 1996), although there are several rodent models that do (Spiegelman and Flier, 1996; Weigle and Kuijper, 1996). Human metabolism is a quantitative trait that, along with environmental and behavioral aspects, is responsible for metabolic activities and disorders (Clement et al., 1998; Montague et al., 1997; Comuzzie and Allison, 1998; Hill and Peters, 1998).

Obesity is an excess of subcutaneous fat in proportion to lean body mass, relating to calorie intake and use. Anorexia is a prolonged loss of appetite whereas cachexia is a general physical wasting and malnutrition usually associated with chronic disease, such as certain types of cancers or HIV. Diabetes, another type of metabolic disorder, is a variable disorder of carbohydrate metabolism caused by a combination of hereditary and environmental factors and usually characterized by excessive urine production and excessive amounts of sugar in the blood and urine, as well as by thirst, hunger and loss of weight. Underlying metabolic dysfunctions contribute substantially to all of the aforementioned metabolic disorders.

Fasting and Feeding Experimental Models

While there are many known candidate genes that may contribute to metabolic disorders (Table 1), other targets for various therapies are desirable. Optimal targets include those genes that are differentially-regulated during fasting and feeding because of their immediate relationship to food intake.

TABLE 1

Selected candidate genes for human obesity/body composition (Comuzzie and Allison, 1998)

| Phenotype | Gene | Notes |
|---|---|---|
| Obesity | agouti signaling polypeptide | In mutant ($a^Y/a^Y$) mice, agouti is expressed ubiquitously (instead of only skin in wild-type mice), and antagonizes melanocyte stimulating hormone receptor ligation. |
| | carboxypeptidase | In agouti ($a^Y/a^Y$) mice, a mutation in this enzyme prevents processing of proopiomelanocortin. |
| | leptin | In mice, encoded by ob gene; mutant homozygotes express the obese diabetic (db) mouse phenotype due to aberrant leptin translational termination. |
| | leptin receptor | fa/fa (fatty) rats (Phillips et al., 1996) |
| | tubby polypeptide | May effect processing of other obesity-related polypeptides: neuropeptide Y and POMC (Aron et al., 1997; Guan et al., 1998; Spiegelman and Flier, 1996; Weigle and Kuijper, 1996). |
| | proopiomelanocortin (POMC) | Knock-out mice express a phenotype resembling that of agouti mutants (Yaswen et al., 1999). |
| | tumor necrosis factor-α | Genetic linkage study of Pima Indians; up-regulated in adipose tissue in obese people and rodents (Norman et al., 1995). |
| Energy balance | uncoupling polypeptides (1, 2, 3) | Uncoupling proteins disengage ATP synthesis from mitochondrial respiration, thereby affecting metabolic rate (Schrauwen et al., 1999). |
| Satiety | cholecystokinin A and its receptor | (CCK) stimulates secretion of digestive enzyme and promotes cell growth (Cancela, 2001). |
| Feeding behavior | melanocortin and its receptors (3, 4) | Appetite suppressants, control feeding behavior, among many other diverse functions (Wikberg et al., 2000). |
| Appetite regulation | neuropeptide Y | Promote feeding, although knockout mice expressed a weaker phenotype than expected. Double mutant mice, such as ob/ob npy-/npy- have more striking phenotypes (Beck, 2001). |
| | neuropeptide Y receptor | |
| | ghrelin | Stimulates feeding and weight gain in mice (Nakazato et al., 2001). |

TABLE 1-continued

Selected candidate genes for human obesity/body composition (Comuzzie and Allison, 1998)

| Phenotype | Gene | Notes |
| --- | --- | --- |
| | other orexins | Stimulate feeding, e.g. (Sakurai et al., 1998a; Sakurai et al., 1998b). |
| Adipocyte differentiation | peroxisome proliferator activated receptor-γ | Adipogenic transcription factor (Kersten, 2001). |
| | β-3-adrenergic receptor | Expressed mostly in adipocytes. May be coupled to lipolysis (Strosberg, 1997). |

Non-pharmaceutical interventions for treating and controlling metabolic disorders, include diet, exercise, psychiatric treatment and surgery. Pharmaceutical interventions include mostly appetite suppressants and energy expenditure/nutrient-modifying agents. However both forms of treatments are often unsatisfactory, due to either unwanted complications, difficulties in maintaining weight loss after treatment, and/or unwanted side effects. While there are many known candidate genes that may contribute to obesity (Table 1), other targets are desirable. Optimal targets include those genes that are differentially-regulated during fasting and feeding because of their immediate relationship to food intake. These genes, along with their expression regulatory elements and encoded polypeptides represent a class of molecules that are desirable therapeutic targets and are also useful in predicting treatment success by expression profiling.

SUMMARY

In a first aspect, the present invention is an isolated polypeptide, having at least 80% sequence identity to the sequence of SEQ ID NO:2. The polypeptide may have at least 85%, 90%, 95%, 98% and 99% sequence identity to the sequence of SEQ ID NO:2.

In a second aspect, the present invention is an isolated polynucleotide, having at least 80% sequence identity to the sequence of SEQ ID NO:1, or a complement of the polynucleotide. The polynucleotide may have at least 85%, 90%, 95%, 98% and 99% sequence identity to the sequence of SEQ ID NO:1.

In a third aspect, the present invention is a method of treating a metabolic disorder, comprising modulating the activity of Acidic Mammalian Molecule.

In a fourth aspect, the present invention is a method of detecting a disorder associated with changes in Acidic Mammalian Molecule gene expression, comprising detecting a change in expression or activity of Acidic Mammalian Molecule.

In a fifth aspect, the present invention is a method for determining whether a compound up-regulates or down-regulates the transcription of an Acidic Mammalian Molecule gene, comprising contacting the compound with a composition comprising a RNA polymerase and the gene and measuring the amount of Acidic Mammalian Molecule gene transcription.

In a sixth aspect, the present invention is a method for determining whether a compound up-regulates or down-regulates the translation of an Acidic Mammalian Molecule gene, comprising contacting the compound with a composition comprising a ribosome and a polynucleotide corresponding to a mRNA of the gene and measuring the amount of Acidic Mammalian Molecule gene translation.

In a seventh aspect, the present invention is a transgenic non-human animal, having a disrupted Acidic Mammalian Molecule gene.

In an eighth aspect, the present invention is a transgenic non-human animal, comprising an exogenous polynucleotide having at least 80% sequence identity to the sequence of SEQ ID NO:1, or a complement of the polynucleotide. The polynucleotide may have at least 85%, 90%, 95%, 98% and 99% sequence identity to the sequence of SEQ ID NO:2.

In a ninth aspect, the present invention is a method of screening a sample for an Acidic Mammalian Molecule gene mutation, comprising comparing an Acidic Mammalian Molecule nucleotide sequence in the sample with SEQ ID NO:1.

In a tenth aspect, the present invention is a method of measuring Acidic Mammalian Molecule agonist or antagonist activity of a compound comprising contacting the compound with a composition comprising a polypeptide having at least 80% sequence identity to the sequence of SEQ ID NO:2 and, determining if Acidic Mammalian Molecule activity is changed.

DETAILED DESCRIPTION

Figure 1:
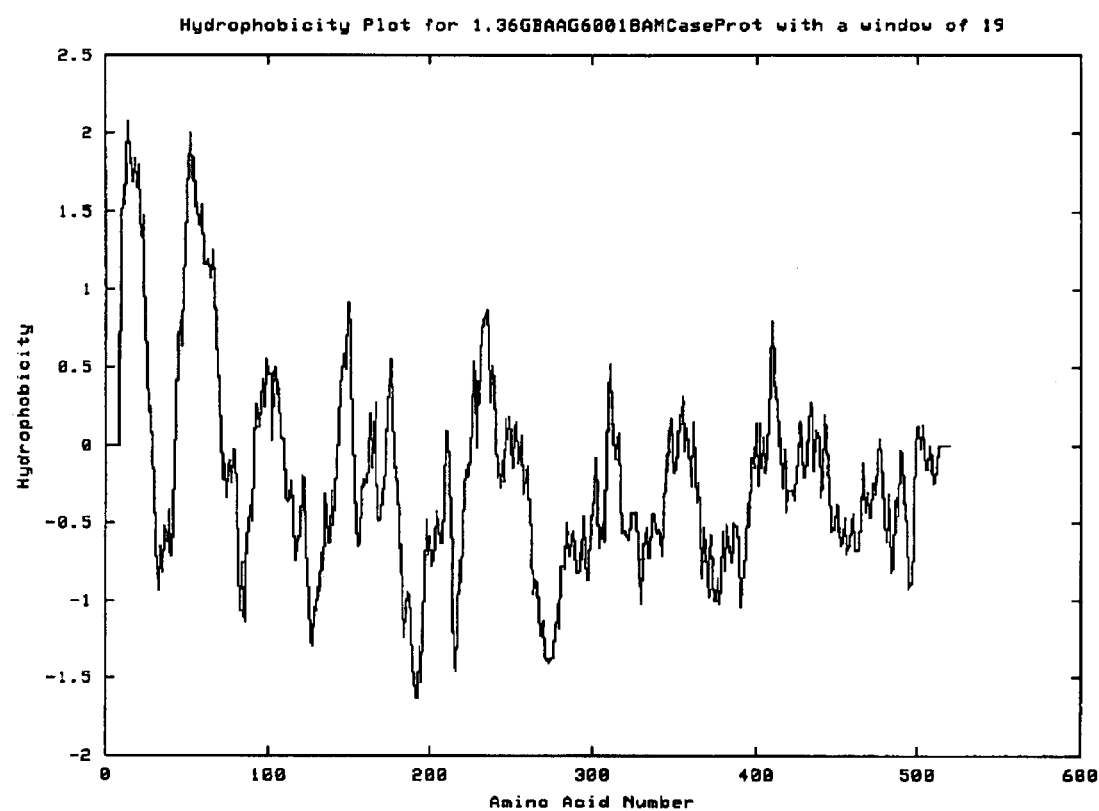
FIG. 1 shows a hydrophobicity plot (19 aa window) for SEQ ID NO:3 (Mouse AMCase precursor polypeptide).

Genes that are remarkably differentially-regulated during fasting-feeding cycles are important weapons in the arsenal to treat and predict treatment success in obese subjects, as well as those afflicted with other metabolic disorders. These genes are useful in treating obesity, as markers for obesity diagnosis or propensity, and prognosis of the potential success of various treatment plans.

To identify those genes that are differentially-regulated during fasting-feeding cycles, mice were put on various feeding regimes and, at pre-determined time points, mRNA was isolated from the stomach. Expression levels in fasting and feeding mice were then assessed and compared to identify those mRNA messages that were either up- or down-regulated, using GeneCalling experiments (Shimkets et al., 1999) (see Examples) and homology searches such as BLAST (Altschul et al., 1997) and hydrophobicity plots to characterize the encoded polypeptide. In one set of experiments, novel acidic mammalian molecules (AMMs) were identified that were differentially-expressed: they are down-regulated two-fold down in response to fasting followed by two-fold induction in response to feeding after fasting.

These differentially-expressed genes, mRNAs and polypeptides can be manipulated in a variety of ways to treat obesity. Those messages that are up-regulated during feeding, such as the novel acidic mammalian proteins, represent molecules that play roles in metabolic rate, satiety, and appetite suppression, as well as the expression and activation of molecules that play such roles. For example, if a molecule up-regulated during feeding signals satiety, then increased expression of this gene or administration of the polypeptide (or its active fragments) to obese subjects that habitually overeat can aid the subject in diminishing the quantity of food that they need to feel satisfied. Differentially-regulated genes during fasting and feeding after fasting are those molecules that signal or effect metabolic rate. Those that accelerate metabolic rate could be up-regulated in treatment to enhance the caloric utilization.

Recently, two novel chitinase family proteins, eosinophil chemotactic cytokine (ECF-L) and acidic mammalian chitinase (AMCase) have been isolated from the stomach tissues of both humans and rodents.

Next to cellulose, chitin is the most abundant glycopolymer on earth, being present as a structural component in cell walls of most fungi, the microfilarial sheath of parasitic nematodes and the exoskeleton of all types of arthropods, as well as in the lining of the guts of many insects. Recently, the first human chitinases, chitotriosdiase and acidic mammalian chitinase, have been isolated and cloned (Boot et al., 2001, Boot et al., 1995, Renkema et al., 1995). The relevance of chitinases to human physiology is yet to be understood.

Chitotriosidase activity is modulated in several disorders, including Gaucher disease, sarcoidosis and leishamaniasis (Hollak et al., 1994). Chitotriosidase activity is highly elevated in the plasma of symptomatic Gaucher disease patients. Gaucher disease is an autosomal recessive genetic disorder, wherein no or little glucocerebrosidase is produced and resulting in abberrant lipid storage. A hematologic abnormality, Gaucher disease often causes hyperspleenism, bone lesions, skin pigmentation and pingueculae. This disorder is particularly frequent in Ashkenazi Jews and may strike at any age.

Individuals that are homozygous null for chitotriosidase exist in about 6% of the population (Giraldo et al., 2001), although no gross abnormalities are observed. The role or chitotriosidase in human physiology is unknown, although suggestions that it may be expressed to combat chitin-containing pathogens as well as in morphogenetic events has been made (Boot et al., 1995). That only 6% of the population is null for this gene, and not the prediction of 25% based on Mendelian single gene inheritance patterns leads to the speculation that chitotriosidase plays an important role.

Chitotriosidase is remarkably homologous to chitinases from plants, bacteria, fungi, nematodes and insects. Analogous to some plant chitinases, recombinant chitotriosidase has been found to inhibit hyphal growth of chitin-containing fungi such as *Canidida* and *Aspergillus* species. The specific expression by phagocytes also suggests a physiological role in defense against chitin-containing pathogens.

A second mammalian chitinolytic enzyme, Acidic Mammalian Chitinase (AMCase) that is expressed in the gastrointestinal tract of man and rodent has also been described (Boot et al., 2001). Like chitotriosidase, AMCase is synthesized as a 50-kDa protein containing a 39-kDa N-terminal catalytic domain, a hinge region, and a C-terminal chitin binding domain. However, AMCase is extremely acid stable and shows a distinct second pH optimum around pH 2.

AMCase is 99% similar to another, earlier identified member of the chitinase protein family, eosinophil chemotactic cytokine (ECF-L). Using a comprehensive search of GenBank and EMBL polynucleotide data bases, Owhashi et al. (Owhashi et al., 2000) found that ECF-L possesses significant homology with prokaryotic chitinases, class III plant chitinases, fungus chitinase, insect and nematode chitinase, and chitinase family proteins distributed in vertebrate animals. ECF-L also possesses the chemokine CXC consensus sequence near the $NH_2$ terminus. However, the rest of ECF-L shows poor homology with chemokines.

ECF-L is produced in parasitic infections upon stimulation of specific antigens. ECF-Ls are also expressed in allergic and inflammatory reactions. Production of ECF-L at local sites of pathogen invasion would contribute to the triggering of the influx of eosinophils that act as effectors of parasite killing. Thus ECF-L may have evolved from a chitinase as an immune molecule from invading parasites by means of accumulating eosinophils followed by secreting toxic substances rather than directly digesting parasites.

Embodiments

The following embodiments are given as examples of various ways to practice the invention. Many different versions will be immediately apparent to one of skill in the various arts to which this invention pertains.

Obesity Treatment

AMMs can be exogenously regulated via a variety of means well-known in the art to treat or prevent obesity and other metabolic disorders, including: gene therapy techniques (including cell transformation of polynucleotides encoding active portions of a gene, anti-sense oligonucleotides), small molecule antagonists and agonists, polypeptide administration (for example, in replacement therapies), antibody administration to inhibit ligand-receptor interactions, etc.

Diagnostic and Prognostic Tools

Another application for differentially-regulated genes is treatment prognosis and diagnosis. For example, if an obese subject constitutively expresses a gene that should be differentially-regulated, such as an AMM, then treatments can be designed that target the expression and/or activity of that particular polypeptide. If an obese subject's expression profile (the totality of all, or preferably, a subset containing genes known to be differentially-regulated during fasting and feeding, such as AMMs) is aberrant when compared to a lean individual, then a skilled artisan can determine which genes represent therapeutic targets, thus allowing many targets to be identified simultaneously. Finally, such expression profiling can diagnose the susceptibility of a subject to become obese.

In addition, monitoring AMM polynucleotide or polypeptide expression levels can be used as marker to monitor weight control treatments or treatments for other metabolic conditions, much as chitotriosidase can be used to monitor treatment of type 1 Gaucher's disease (Giraldo et al., 2001).

Differentially-expressed Molecules During Fasting and Feeding

To distinguish between genes (and related polynucleotides) and the polypeptides that they encode, the abbreviations for polynucleotides are indicated by italicized (or underlined) text, while abbreviations for the polypeptides are not italicized. Thus, AMM refers to the polynucleotide sequence that encodes AMM.

Acidic Mammalian Molecules

In experiments examining gene expression during fasting and feeding, AMM, mRNA was found to have a complex pattern of modulation: fasting induced an approximately two-fold down-regulation; and, after post-fasting feeding, approximate two-fold up-regulation.

The novel AMMs of the invention include the polynucleotides that encode AMMs, which sequence comprises, for example, that provided in Table 2, or fragments thereof. Mutant or variant acidic mammalian molecules, any of whose bases may be changed from the corresponding base shown in Table 2 while still encoding a polypeptide that maintains the activity or a physiological function of the AMM fragment, or a fragment of such a polynucleotide, are also useful. Furthermore, polynucleotides, or fragments, whose sequences are complementary to those of Table 2, are also advantageous. The invention additionally includes polynucleotides or polynucleotide fragments, or their complements, whose structures include chemical modifications. Such modifications include modified bases, and polynucleotides whose sugar phosphate backbones are modified or derivatized. These modifications are carried out at least in part to enhance the chemical stability of the modified polynucleotide, such that they may be used, for example, as anti-sense binding polynucleotides in therapeutic applications. In the mutant or variant polynucleotides, and their complements, up to 20% or more of the bases may be so changed.

The invention also includes polypeptides and nucleotides having 80–100%, including 81, 82, 83, 84, 85, 86, 87, 88, 89, 90, 91, 92, 93, 94, 95, 96, 97, 98 and 99%, sequence identity to the sequence presented in Table 2, as well as nucleotides encoding any of these polypeptides, and compliments of any of these nucleotides.

The novel acidic mammalian molecule polypeptides of the invention include the polypeptide fragments which sequences comprise that provided in Table 3, or both sequences and fragments thereof The invention also includes acidic mammalian molecule mutant or variant polypeptides, any residues of which may be changed from the corresponding residue shown in Table 3, while still encoding a polypeptide that maintains a native activity or physiological function, or a functional fragment thereof. In the mutant or variant AMM, up to 20% or more of the residues may be so changed.

The invention further encompasses antibodies (Abs) and Ab fragments, such as $F_{ab}$ or $(F_{ab})'_2$, that bind immunospecifically to any of the AMMs of the invention.

Because of its differential regulation in fasting (down-regulated) vs. feeding (up-regulated) mice, AMM polypeptides and/or AMM-interacting polypeptides are useful as drugs or drug targets for treating metabolic diseases, including diabetes, obesity, cachexia and anorexia. AMM can also serve as a marker for monitoring metabolic phenomena. For example, in obese individuals (or individuals prone to obesity), AMM expression and/or activity can be up-regulated to discourage feeding or increase metabolism. Likewise, in individuals dangerously below weight, such as those suffering from cachexia or anorexia, AMM expression and/or activity can be down-regulated to promote feeding or slow metabolism.

TABLE 2

AMM polynucleotide sequence (SEQ ID NO: 1)
```
gtaggaagtg agagtggggg tggaagcttc cggaggaagc tttggaggca gtggattttg   60
tgccgacaaa gcagatggcc tttaccctgt ggcagatgac agaaatgctt tttggcagtg  120
catcaatgga atcacatacc agcagcattg tcaagcaggg cttgtttttg ataccagctg  180
taattgctgc aactggccat gaacctaatg ccattttttcc agaaattttt gcatttttcct 240 ttattcctca ccaaaagtaa cttttttccc tttaaccttta tgcaataaaa ttggtagccg  300
taaaaaaaaa aaaaaaaa                                                319
```

Table 3 presents the novel acidic mammalian molecule polypeptide amino acid sequence encoded by SEQ ID NO:1.

TABLE 3

Novel AMM polypeptide sequence (SEQ ID NO:2)
```
Glu Val Arg Val Gly Val Glu Ala Ser Gly Gly Ser Phe Gly Gly Ser
1               5                   10                  15

Gly Phe Cys Ala Asp Lys Ala Asp Gly Leu Tyr Pro Val Ala Asp Asp
            20                  25                  30

Arg Asn Ala Phe Trp Gln Cys Ile Asn Gly Ile Thr Tyr Gln Gln His
                35                  40                  45

Cys Gln Ala Gly Leu Val Phe Asp Thr Ser Cys Asn Cys Cys Asn Trp
        50                  55                  60

Pro
65
```

The predicted molecular weight of the novel AMM, which is 65 amino acids in length, without post-translational modifications or alternative splicing, is 6937.6 Daltons, with a predicted pI of 4.18. Table 4 presents other predicted physical characteristics of the novel acidic mammalian molecule polypeptide (SEQ ID NO:2).

TABLE 4

Predicted physical properties of Novel AMM

| | Wavelength | | | | |
|---|---|---|---|---|---|
| | 276 nm | 278 nm | 279 nm | 280 nm | 282 nm |
| Values assuming all Cys residues appear as half cystines | | | | | |
| Extinction Coefficient | 14135 | 14381 | 14370 | 14300 | 13900 |
| Optical Density | 2.037 | 2.073 | 2.071 | 2.061 | 2.004 |
| Values assuming no Cys residues appear as half cystines | | | | | |
| Extinction Coefficient | 13700 | 14000 | 14010 | 13940 | 13600 |

TABLE 4-continued

Predicted physical properties of Novel AMM

| | Wavelength | | | | |
|---|---|---|---|---|---|
| | 276 nm | 278 nm | 279 nm | 280 nm | 282 nm |
| Optical Density | 1.975 | 2.081 | 2.019 | 2.009 | 1.960 |

[1] Conditions at which these equations are valid are: pH 6.5, 6.0 M guanidium hydrochloride, 0.02 M phosphate buffer.

Mouse AMCase Precursor

Acidic Mammalian Chitinase (AMCase) is an acid stable enzyme, capable of cleaving artificial chitin-like substrates as well as crab shell chitin and chitin as present in the fungal cell wall.

Table 5 shows a partial nucleotide sequence (SEQ ID NO:3; GenBank Accession Number: AAG60018/NP_068569) representing the mouse homolog of the human AMCase precursor (SEQ ID NO:5)/Eosinophil Chemokine precursor (SEQ ID NO:3).

TABLE 5

Polypeptide sequence of AMCase Precursor (mouse)
(SEQ ID NO:3; GenBank Accession No: AAG60018)

```
Gly Ile Gly Asx Ala Ala Gly Ala Phe Ala Cys Ile Asp Ile Cys Met
1               5                   10                  15
Ala Met Met Ala Leu Ile Ala Asn Cys His Ile Thr Ile Asn Ala Ser
            20                  25                  30
Glu Pro Arg Glu Cys Arg Ser Arg Met Ser Met Ser Cys Leu Ser Met
            35                  40                  45
Ala Lys Leu Leu Leu Val Thr Gly Leu Ala Leu Leu Leu Asn Ala Gln
        50                  55                  60
Leu Gly Ser Ala Tyr Asn Leu Ile Cys Tyr Phe Thr Asn Trp Ala Gln
65                  70                  75                  80
Tyr Arg Pro Gly Leu Gly Ser Phe Lys Pro Asp Asp Ile Asn Pro Cys
                85                  90                  95
Leu Cys Thr His Leu Ile Tyr Ala Phe Ala Gly Met Gln Asn Asn Glu
                100                 105                 110
Ile Thr Thr Ile Glu Trp Asn Asp Val Thr Leu Tyr Lys Ala Phe Asn
            115                 120                 125
Asp Leu Lys Asn Arg Asn Ser Lys Leu Lys Thr Leu Leu Ala Ile Gly
        130                 135                 140
Gly Trp Asn Phe Gly Thr Ala Pro Phe Thr Thr Met Val Ser Thr Ser
145                 150                 155                 160
Gln Asn Arg Gln Thr Phe Ile Thr Ser Val Ile Lys Phe Leu Arg Gln
                165                 170                 175
Tyr Gly Phe Asp Gly Leu Asp Leu Asp Trp Glu Tyr Pro Gly Ser Arg
                180                 185                 190
Gly Ser Pro Pro Gln Asp Lys His Leu Phe Thr Val Leu Val Lys Glu
            195                 200                 205
Met Arg Glu Ala Phe Glu Gln Glu Ala Ile Glu Ser Asn Arg Pro Arg
        210                 215                 220
Leu Met Val Thr Ala Ala Val Ala Gly Gly Ile Ser Asn Ile Gln Ala
225                 230                 235                 240
Gly Tyr Glu Ile Pro Glu Leu Ser Lys Tyr Leu Asp Phe Ile His Val
                245                 250                 255
Met Thr Tyr Asp Leu His Gly Ser Trp Glu Gly Tyr Thr Gly Glu Asn
```

TABLE 5-continued

Polypeptide sequence of AMCase Precursor (mouse)
(SEQ ID NO:3; GenBank Accession No: AAG60018)

```
                    260                 265                 270
Ser Pro Leu Tyr Lys Tyr Pro Thr Glu Thr Gly Ser Asn Ala Tyr Leu
        275                 280                 285

Asn Val Asp Tyr Val Met Asn Tyr Trp Lys Asn Asn Gly Ala Pro Ala
        290                 295                 300

Glu Lys Leu Ile Val Gly Phe Pro Glu Tyr Gly His Thr Phe Ile Leu
305                 310                 315                 320

Arg Asn Pro Ser Asp Asn Gly Ile Gly Ala Pro Thr Ser Gly Asp Gly
                325                 330                 335

Pro Ala Gly Ala Tyr Thr Arg Gln Ala Gly Phe Trp Ala Tyr Tyr Glu
                340                 345                 350

Ile Cys Thr Phe Leu Arg Ser Gly Ala Thr Glu Val Trp Asp Ala Ser
            355                 360                 365

Gln Glu Val Pro Tyr Ala Tyr Lys Ala Asn Glu Trp Leu Gly Tyr Asp
        370                 375                 380

Asn Ile Lys Ser Phe Ser Val Lys Ala Gln Trp Leu Lys Gln Asn Asn
385                 390                 395                 400

Phe Gly Gly Ala Met Ile Trp Ala Ile Asp Leu Asp Asp Phe Thr Gly
                405                 410                 415

Ser Phe Cys Asp Gln Gly Lys Phe Pro Leu Thr Ser Thr Leu Asn Lys
                420                 425                 430

Ala Leu Gly Ile Ser Thr Glu Gly Cys Thr Ala Pro Asp Val Pro Ser
            435                 440                 445

Glu Pro Val Thr Thr Pro Pro Gly Ser Gly Ser Gly Gly Gly Ser Ser
        450                 455                 460

Gly Gly Ser Ser Gly Gly Ser Gly Phe Cys Ala Asp Lys Ala Asp Gly
465                 470                 475                 480

Leu Tyr Pro Val Ala Asp Asp Arg Asn Ala Phe Trp Gln Cys Ile Asn
                485                 490                 495

Gly Ile Thr Tyr Gln Gln His Cys Gln Ala Gly Leu Val Phe Asp Thr
                500                 505                 510

Ser Cys Asn Cys Cys Asn Trp Pro
            515                 520
```

Mouse AMCase precursor is a polypeptide of approximately 520 residues with a predicted molecular weight, disregarding post-translational modifications, of 56895.9Daltons, and a pI of 4.86. Table 6 shows other predicted physical properties of mouse AMCase precursor (SEQ ID NO:3). FIG. 1 presents a hydrophobicity plot of mouse AMCase precursor using a sliding window of 19 residues.

TABLE 6

Mouse AMCase Precursor (SEQ ID NO: 3; AAG60018) physical properties

| | Wavelength (nm) | | | | |
|---|---|---|---|---|---|
| | 276 | 278 | 279 | 280 | 282 |
| Values assuming all Cys appear as half cystines | | | | | |
| Extinction coefficient | 107610 | 108816 | 108165 | 106930 | 103600 |
| Optical density | 1.891 | 1.913 | 1.901 | 1.879 | 1.821 |
| Values assuming no Cys appear as half cystines | | | | | |
| Extinction coefficient | 106450 | 107800 | 107205 | 105970 | 102800 |
| Optical density | 1.871 | 1.895 | 1.884 | 1.863 | 1.807 |

TABLE 6-continued

Mouse AMCase Precursor (SEQ ID NO: 3; AAG60018) physical properties

| Wavelength (nm) | | | | |
|---|---|---|---|---|
| 276 | 278 | 279 | 280 | 282 |

The conditions at which these equations are valid are: pH 6.5, 6.0 M guanidium hydrochloride, phosphate buffer.

Table 7 shows the Human AMCase Precursor sequence (SEQ ID NO:5; GenBank Accession No. AAG60019).

TABLE 7

Human AMCase Precursor sequence (SEQ ID NO:5; GenBank Accession No. AAG60019)

Met Thr Lys Leu Ile Leu Leu Thr Gly Leu Val Leu Ile Leu Asn Leu
1               5                   10                  15

Gln Leu Gly Ser Ala Tyr Gln Leu Thr Cys Tyr Phe Thr Asn Trp Ala
            20                  25                  30

Gln Tyr Arg Pro Gly Leu Gly Arg Phe Met Pro Asp Asn Ile Asp Pro
            35                  40                  45

Cys Leu Cys Thr His Leu Ile Tyr Ala Phe Ala Gly Arg Gln Asn Asn
50                  55                  60

Glu Ile Thr Thr Ile Glu Trp Asn Asp Val Thr Leu Tyr Gln Ala Phe
65                  70                  75                  80

Asn Gly Leu Lys Asn Lys Asn Ser Gln Leu Lys Thr Leu Leu Ala Ile
                85                  90                  95

Gly Gly Trp Asn Phe Gly Thr Ala Pro Phe Thr Ala Met Val Ser Thr
            100                 105                 110

Pro Glu Asn Arg Gln Thr Phe Ile Thr Ser Val Ile Lys Phe Leu Arg
            115                 120                 125

Gln Tyr Glu Phe Asp Gly Leu Asp Phe Asp Trp Glu Tyr Pro Gly Ser
    130                 135                 140

Arg Gly Ser Pro Pro Gln Asp Lys His Leu Phe Thr Val Leu Val Gln
145                 150                 155                 160

Glu Met Arg Glu Ala Phe Glu Gln Glu Ala Lys Gln Ile Asn Lys Pro
                165                 170                 175

Arg Leu Met Val Thr Ala Ala Val Ala Ala Gly Ile Ser Asn Ile Gln
            180                 185                 190

Ser Gly Tyr Glu Ile Pro Gln Leu Ser Gln Tyr Leu Asp Tyr Ile His
        195                 200                 205

Val Met Thr Tyr Asp Leu His Gly Ser Trp Glu Gly Tyr Thr Gly Glu
    210                 215                 220

Asn Ser Pro Leu Tyr Lys Tyr Pro Thr Asp Thr Gly Ser Asn Ala Tyr
225                 230                 235                 240

Leu Asn Val Asp Tyr Val Met Asn Tyr Trp Lys Asp Asn Gly Ala Pro
            245                 250                 255

Ala Glu Lys Leu Ile Val Gly Phe Pro Thr Tyr Gly His Asn Phe Ile
            260                 265                 270

Leu Ser Asn Pro Ser Asn Thr Gly Ile Gly Ala Pro Thr Ser Gly Ala
        275                 280                 285

Gly Pro Ala Gly Pro Tyr Ala Lys Glu Ser Gly Ile Trp Ala Tyr Tyr
    290                 295                 300

Glu Ile Cys Thr Phe Leu Lys Asn Gly Ala Thr Gln Gly Trp Asp Ala
305                 310                 315                 320

TABLE 7-continued

Human AMCase Precursor sequence (SEQ ID NO:5; GenBank Accession No. AAG60019)

```
Pro Gln Glu Val Pro Tyr Ala Tyr Gln Gly Asn Val Trp Val Gly Tyr
            325                 330                 335

Asp Asn Ile Lys Ser Phe Asp Ile Lys Ala Gln Trp Leu Lys His Asn
            340                 345                 350

Lys Phe Gly Gly Ala Met Val Trp Ala Ile Asp Leu Asp Asp Phe Thr
            355                 360                 365

Gly Thr Phe Cys Asn Gln Gly Lys Phe Pro Leu Ile Ser Thr Leu Lys
            370                 375                 380

Lys Ala Leu Gly Leu Gln Ser Ala Ser Cys Thr Ala Pro Ala Gln Pro
385                 390                 395                 400

Ile Glu Pro Ile Thr Ala Ala Pro Ser Gly Ser Gly Asn Gly Ser Gly
                405                 410                 415

Ser Ser Ser Ser Gly Gly Ser Ser Gly Gly Ser Gly Phe Cys Ala Val
                420                 425                 430

Arg Ala Asn Gly Leu Tyr Pro Val Ala Asn Asn Arg Asn Ala Phe Trp
            435                 440                 445

His Cys Val Asn Gly Val Thr Tyr Gln Gln Asn Cys Gln Ala Gly Leu
        450                 455                 460

Val Phe Asp Thr Ser Cys Asp Cys Cys Asn Trp Ala
465                 470                 475
```

Human AMCase, a polypeptide of approximately 525 amino acid residues, has a predicted molecular weight, disregarding post-translational modifications) of 57416.7 Daltons, and a pI of 5.86. Some additional physical properties are shown in Table 8.

TABLE 8

Human AMCase Precursor (SEQ ID NO: 5; AAG60019) physical properties

| | Wavelength (nm) | | | | |
|---|---|---|---|---|---|
| | 276 | 278 | 279 | 280 | 282 |
| Values assuming all Cys appear as half cystines | | | | | |
| Extinction coefficient | 109060 | 110216 | 109510 | 108210 | 104800 |
| Optical density | 1.899 | 1.920 | 1.907 | 1.885 | 1.825 |
| Values assuming no Cys appear as half cystines | | | | | |
| Extinction coefficient | 107900 | 109200 | 108550 | 107250 | 104000 |
| Optical density | 1.879 | 1.902 | 1.891 | 1.868 | 1.811 |

The conditions at which these equations are valid are: pH 6.5, 6.0 M guanidium hydrochloride, phosphate buffer.

Comparison of mouse contig and human AMCase precursor by BLASTX is shown in Table 9. The query sequence was the mouse contig cgmm10e1167.4_37627-215EXT (SEQ ID NO:2), and the subject sequence was >ptnr:SPTREMBL-ACC:Q9BZP6 ACIDIC MAMMALIAN CHITINASE PRECURSOR (EC3.2.1.14)-(Human), GenBank ACC:AAG60019; SEQ ID NO:5; Table 8: plus strand HSPs).

Table 9 Alignment by BLASTX of residues 5–64 of SEQ ID NO: 2 (wherein polynucleotide sequence SEQ ID NO:1 is translated; the numbers refer to nucleotides 17–96 of SEQ ID NO:1) and 5 (amino acid residues 416–475).

TABLE 9

Alignment by BLASTX of residues 5-64 of SEQ ID NO:2 (wherein polynucleotide
sequence SEQ ID NO:1 is translated; the numbers refer to nucleotides
17-196 of SEQ ID NO:1) and 5 (amino acid residues 416-475).

```
Query:   17 GVEASGGSFGGSGFCADKADGLYPVADDRNAFWQCINGITYQQHCQAGLVFDTSCNCCNW 196
            G +SGGS GGSGFCA +A+GLYPVA++RNAFW C+NG+TYQQ+CQAGLVFDTSC+CCNW
Sbjct:  416 GSSSSGGSSGGSGFCAVRANGLYPVANNRNAFWHCVNGVTYQQNCQAGLVFDTSCDCCNW 475
```

The BLASTX program gave the following results: Score= 282 (99.3 bits), Expect=3.1e-23, P=3.1e-23 and Identities= 46/60 (76%), Positives=55/60 (91%), Frame=+2. Thus the mouse contig cgmm10e1167.4_37627-215 (SEQ ID NO:1) represents a partial nucleotide sequence representing the mouse homologue of the human AMCase precursor/ Eosinophil Chemokine precursor (SEQ ID NO:5).

Other sequences that have limited homology, as determined by BlastN analysis, include a novel *Homo sapiens* polynucleotide (Atsushi and Shigeru, WO/0136633, 2001) that is 79% similar. Another polypeptide with very low similarity (50%) includes sequence CAC37768 (Dietsch et al., WO/0123430, 2001).

CLUSTALW software, useful in viewing the specific details of where related sequences align, mismatch, or have gap, was used to determine nearest neighbors (Thompson et al., 1994). The following sequences were compared for homology using the CLUSTALW software (Table 14) the human eosinophil chemotactic-like cytokine (SEQ ID NO:6), Table 10; NM_021797 (of which the polypeptide sequence is provided in Table 10a; SEQ ID NO:7)), human mammalian acid chitinase precursor (SEQ ID NO:8; Table 11; AF290004.1), novel acidic mammalian molecule/ LOE1167.4/1.3610e1167.4_367EXT (SEQ ID NO:1; Table 2), mammalian chitinase precursor/ 1.36Gbaf290003Mmchitinaseprecu) (SEQ ID NO:9; Table 12; AAG60019), and mammalian chemokine/ 1.36GBbc011134Mmchemokine (SEQ ID NO:10; Table 13; BC011134). Highly conserved regions (black) suggest those regions of the polypeptide that are most important for function. The sequence type was explicitly set to DNA and the sequence format is Pearson.

TABLE 10

Human eosiniphil chemotactic-like cytokine (SEQ ID NO:6)

```
gaaacctcct cgtctgtgca cgaacaggtg gccgactctg gagcccaggc tgttgctttc   60
cagtctggtg gtgaatcctc catagtctgg aacagccagc tgaaaactct cctggccatt  120
ggaggctgga acttcaggac tgcccctttc actgccatgg tttctactcc tgagaaccgc  180
cagactttca tcacctcagt catcaaattc ctgcgccagt atgagtttga cgggctggac  240
tttgactggg agtaccctgg ctctcgtggg agccctcctc aggacaagca tctcttcact  300
gtcctggtgc aggaaatgcg tgaagctttt gagcaggagg ccaagcagat caacaagccc  360
aggctgatgg tcactgctgc agtagctgct ggcatctcca atatccagtc tggctatgag  420
atcccccaac tgtcacagta cctggactac atccatgtca tgacctacga cctccatggc  480
tcctgggagg gctacactgg agagaacagc cccctctaca aatacccgac tgacaccggc  540
agcaacgcct acctcaatgt ggattatgtc atgaactact ggaaggacaa tggagcacca  600
gctgagaagc tcatcgttgg attccctacc tatggacaca acttcatcct gagcaacccc  660
tccaacactg gaattggtgc ccccacctct ggtgctggtc ctgctgggcc ctatgccaag  720
gagtctggga tctgggctta ctacgagatc tgtaccttcc tgaaaaatgg agccactcag  780
ggatgggatg cccctcagga agtgccttat gcctatcagg gcaatgtgtg ggttggctat  840
gacaacgtca agagcttcga tattaaggct caatggctta agcacaacaa atttggaggc  900
gccatggtct gggccattga tctggatgac ttcactggca ctttctgcaa ccagggcaag  960
tttcccctaa tctccaccct gaagaaggcc cttggcctgc agagtgcaag ttgcacggct 1020
ccagctcagc ccattgagcc aataactgct gctcccagtg gcagcgggaa cgggagcggg 1080
agtagcagct ctggaggcag ctcgggaggc agtggattct gtgctggcag agccaacggc 1140
ctctacccg tggcaaataa cagaaatgcc ttctggcact gcgtgaatgg agtcacgtac 1200
cagcagaact gccaggccgg gcttgtcttc gacaccagct gtgattgctg caactgggca 1260
```

TABLE 10-continued

Human eosiniphil chemotactic-like cytokine taaacctgac ctggtctata ttccctagag ttccagtctc ttttgcttag gacatgttgc 1320
ccctacctaa agtcctgcaa taaaatcagc agtc 1354

TABLE 10a

Human eosiniphil chemotactic-like cytokine (SEQ ID NO:7)

```
Met Val Ser Thr Pro Glu Asn Arg Gln Thr Phe Ile Thr Ser Val Ile
1               5                   10                  15
Lys Phe Leu Arg Gln Tyr Glu Phe Asp Gly Leu Asp Phe Asp Trp Glu
                20                  25                  30
Tyr Pro Gly Ser Arg Gly Ser Pro Pro Gln Asp Lys His Leu Phe Thr
            35                  40                  45
Val Leu Val Gln Glu Met Arg Glu Ala Phe Glu Gln Glu Ala Lys Gln
    50                  55                  60
Ile Asn Lys Pro Arg Leu Met Val Thr Ala Ala Val Ala Ala Gly Ile
65                  70                  75                  80
Ser Asn Ile Gln Ser Gly Tyr Glu Ile Pro Gln Leu Ser Gln Tyr Leu
                85                  90                  95
Asp Tyr Ile His Val Met Thr Tyr Asp Leu His Gly Ser Trp Glu Gly
                100                 105                 110
Tyr Thr Gly Glu Asn Ser Pro Leu Tyr Lys Tyr Pro Thr Asp Thr Gly
            115                 120                 125
Ser Asn Ala Tyr Leu Asn Val Asp Tyr Val Met Asn Tyr Trp Lys Asp
130                 135                 140
Asn Gly Ala Pro Ala Glu Lys Leu Ile Val Gly Phe Pro Thr Tyr Gly
145                 150                 155                 160
His Asn Phe Ile Leu Ser Asn Pro Ser Asn Thr Gly Ile Gly Ala Pro
                165                 170                 175
Thr Ser Gly Ala Gly Pro Ala Gly Pro Tyr Ala Lys Glu Ser Gly Ile
            180                 185                 190
Trp Ala Tyr Tyr Glu Ile Cys Thr Phe Leu Lys Asn Gly Ala Thr Gln
            195                 200                 205
Gly Trp Asp Ala Pro Gln Glu Val Pro Tyr Ala Tyr Gln Gly Asn Val
    210                 215                 220
Trp Val Gly Tyr Asp Asn Val Lys Ser Phe Asp Ile Lys Ala Gln Trp
225                 230                 235                 240
Leu Lys His Asn Lys Phe Gly Gly Ala Met Val Trp Ala Ile Asp Leu
                245                 250                 255
Asp Asp Phe Thr Gly Thr Phe Cys Asn Gln Gly Lys Phe Pro Leu Ile
            260                 265                 270
Ser Thr Leu Lys Lys Ala Leu Gly Leu Gln Ser Ala Ser Cys Thr Ala
            275                 280                 285
Pro Ala Gln Pro Ile Glu Pro Ile Thr Ala Ala Pro Ser Gly Ser Gly
    290                 295                 300
Asn Gly Ser Gly Ser Ser Ser Gly Gly Ser Ser Gly Gly Ser Gly
305                 310                 315                 320
Phe Cys Ala Gly Arg Ala Asn Gly Leu Tyr Pro Val Ala Asn Asn Arg
                325                 330                 335
```

TABLE 10a-continued

Human eosiniphil chemotactic-like cytokine

```
Asn Ala Phe Trp His Cys Val Asn Gly Val Thr Tyr Gln Gln Asn Cys
        340                 345                 350
Gln Ala Gly Leu Val Phe Asp Thr Ser Cys Asp Cys Cys Asn Trp Ala
        355                 360                 365
```

TABLE 11

Human mammalian acid chitinase precursor (SEQ ID NO:8)

```
gctttccagt ctggtggtga atcctccata gtctgaagcc tttgtgataa ccacagaatc   60
agaacatata aaaagctctg cgggactggt gctgactgca accatgacaa agcttattct  120
cctcacaggt cttgtcctta tactgaattt gcagctcggc tctgcctacc agctgacatg  180
ctacttcacc aactgggccc agtaccggcc aggcctgggg cgcttcatgc ctgacaacat  240
cgaccoctgc ctctgtaccc acctgatcta cgcctttgct gggaggcaga caacgagat   300
caccaccatc gaatgaacg atgtgactct ctaccaagct tcaatggcc tgaaaaataa   360
gaacagccag ctgaaaactc tcctggccat ggaggctgg aacttcggga ctgcccttt   420
cactgccatg gtttctactc ctgagaaccg ccagacttc atcacctcag tcatcaaatt   480
cctgcgccag tatgagtttg acgggctgga ctttgactgg gagtaccctg gctctcgtgg   540
gagccctcct caggacaagc atctcttcac tgtcctggtg caggaaatgc gtgaagcttt   600
tgagcaggag gccaagcaga tcaacaagcc caggctgatg gtcactgctg cagtagctgc   660
tggcatctcc aatatccagt ctggctatga gatccccaa ctgtcacagt acctggacta   720
catccatgtc atgacctacg acctccatgg ctcctgggag ggctacactg agagaacag   780
ccccctctac aaatacccga ctgacaccgg cagcaacgcc tacctcaatg tggattatgt   840
catgaactac tggaaggaca atggagcacc agctgagaag ctcatcgttg gattccctac   900
ctatggacac aacttcatcc tgagcaaccc ctccaacact ggaattggtg cccccacctc   960
tggtgctggt cctgctgggc ctatgccaa ggagtctggg atctgggctt actacgagat  1020
ctgtaccttc ctgaaaaatg gagccactca gggatgggat gcccctcagg aagtgcctta  1080
tgcctatcag ggcaatgtgt gggttggcta tgacaacatc aagagcttcg atattaaggc  1140
tcaatggctt aagcacaaca aattggagg cgccatggtc tgggccattg atctggatga  1200
cttcactggc actttctgca accagggcaa gtttcccta atctccaccc tgaagaaggc  1260
cctcggcctg cagagtgcaa gttgcacggc tccagctcag cccattgagc aataactgc   1320
tgctcccagt ggcagcggga acgggagcgg gagtagcagc tctggaggca gctcgggagg  1380
cagtggattc tgtgctgtca gagccaacgg cctctacccc gtggcaaata acagaaatgc  1440
cttctggcac tgcgtgaatg gagtcacgta ccagcagaac tgccaggccg gcttgtctt   1500
cgacaccagc tgtgattgct gcaactgggc ataaacctga cctggtctat attccctaga  1560
gttccagtct cttttgctta ggacatgttg cccctaccta agtcctgca ataaaatcag  1620
cagtc 1625
```

TABLE 12

Mammalian chitinase precursor (Mus musculus; SEQ ID NO:9)

| | | | | | |
|---|---|---|---|---|---|
| cgatggccaa | gctacttctc | gtcacaggtc | tggctcttct | gctgaatgct | cagctggggt 60 |
| ctgcctacaa | tctgatatgc | tatttcacca | actgggccca | gtatcggcca | ggtctgggga 120 |
| gcttcaagcc | tgatgacatt | aaccectgcc | tgtgtactca | cctgatctat | gcctttgctg 180 |
| ggatgcagaa | caatgagatc | accaccatag | aatggaatga | tgttactctc | tataaagctt 240 |
| tcaatgactt | gaaaaacagg | aacagcaaac | tgaaaaccct | cctggcaatt | ggaggctgga 300 |
| actttggaac | tgctcctttc | actaccatgg | tttccacttc | tcagaaccgc | cagaccttca 360 |
| ttacctcagt | catcaaattt | ctgcgtcagt | atgggtttga | tggactggac | ctggactggg 420 |
| aatacccagg | ctcacgtggg | agccctcctc | aggacaagca | tctcttcact | gtcctggtga 480 |
| aggaaatgcg | tgaagctttt | gagcaggagg | ctattgagag | caacaggccc | agactgatgg 540 |
| ttactgctgc | tgtagctggt | gggatttcca | acatccaggc | tggctatgag | atccctgaac 600 |
| tttctaagta | cctggatttc | atccatgtca | tgacatatga | cctccatggc | tcctgggaag 660 |
| gctacactgg | ggagaatagt | cctctttaca | atacccctac | tgagactggt | agcaatgcct 720 |
| acctcaatgt | ggattatgtc | atgaactatt | ggaagaacaa | tggagcccca | gctgagaagc 780 |
| tcattgttgg | attcccagag | tatggacaca | ccttcatcct | gagaaacccc | tctgataatg 840 |
| gaattggtgc | ccctacctct | ggtgatggcc | ctgctggcgc | ctataccaga | caggctgggt 900 |
| tctgggccta | ctatgagatt | tgcacctttc | tgagaagtgg | agccactgag | gtctgggatg 960 |
| cctcccaaga | agtgcctat | gcctataagg | ccaacgagtg | gcttggctat | gacaatatca 1020 |
| agagcttcag | tgttaaggct | cagtggctta | agcagaacaa | ttttggaggt | gccatgatct 1080 |
| gggccattga | ccttgatgac | ttcactggct | ctttctgtga | tcagggaaaa | ttcctctga 1140 |
| cttctacttt | gaacaaagcc | cttggcatat | ccactgaagg | ttgcacagct | cctgacgtgc 1200 |
| cttccgagcc | agtgactact | cctccaggaa | gtgggagtgg | gggtggaagc | tccggaggaa 1260 |
| gctctggagg | cagtggattc | tgtgccgaca | agcagatgg | cctctaccct | gtggcagatg 1320 |
| acagaaatgc | ttttggcag | tgcatcaatg | gaatcacata | ccagcagcat | tgtcaagcag 1380 |
| ggcttgtttt | tgataccagc | tgtaattgct | gcaactggcc | atgaacctaa | tgccattctt 1440 |
| ccagaaattt | ctgcactctc | ctttactcct | caccaaaagt | aactatcttc | cctttaacct 1500 |
| tatgcaataa | aattggtagc | caaaacaaaa 1530 | | | |

TABLE 13

Mammalian chemokine (Mus musculus; SEQ ID NO: 10)

| | | | | | |
|---|---|---|---|---|---|
| ggccaagcta | cttctcgtca | caggtctggc | tcttctgctg | aatgctcagc | tggggtctgc 60 |
| ctacaatctg | atatgctatt | tcaccaactg | gcccagtat | cggccaggtc | tggggagctt 220 |
| caagcctgat | gacattaacc | cctgcctgtg | tactcacctg | atctatgcct | tgctgggat 180 |
| gcagaacaat | gagatcacca | ccatagaatg | gaatgatgtt | actctctata | aagcttcaa 240 |
| tgacttgaaa | aacaggaaca | gcaaactgaa | aaccctcctg | caattggag | ctggaactt 300 |
| tggaactgct | cctttcacta | ccatggtttc | cacttctcag | aaccgccaga | ccttcattac 360 |
| ctcagtcatc | aaatttctgc | gtcagtatgg | gtttgatgga | ctggacctgg | actgggaata 420 |
| cccaggctca | cgtgggagcc | ctcctcagga | caagcatctc | ttcactgtcc | tggtgaagga 480 |
| aatgcgtgaa | gcttttgagc | aggaggctat | tgagagcaac | aggcccagac | tgatggttac 540 |

TABLE 13-continued

Mammalian chemokine (Mus musculus; SEQ ID NO: 10)

```
tgctgctgta gctggtggga tttccaacat ccaggctggc tatgagatcc ctgaactttc   600
taagtacctg gatttcatcc atgtcatgac atatgacctc catggctcct gggagggcta   660
cactggggag aatagtcctc tttacaaata ccctactgag actggtagca atgcctacct   720
caatgtggat tatgtcatga actattggaa gaacaatgga gccccagctg agaagctcat   780
tgttggattc ccagagtatg gacacacctt catcctgaga aacccctctg ataatggaat   840
tggtgcccct acctctggtg atggccctgc tgggccctat accagacagg ctgggttctg   900
ggcctactat gagatttgca cctttctgag aagtggagcc actgaggtct gggatgcctc   960
ccaagaagtg ccctatgcct ataaggccaa cgagtggctt ggctatgaca atatcaagag  1020
cttcagtgtt aaggctcagt ggcttaagca gaacaatttt ggaggtgcca tgatctgggc  1080
cattgacctt gatgacttca ctggctcttt ctgtgatcag ggaaaatttc ctctgacttc  1140
tactttgaac aaagcccttg gcatatccac tgaaggttgc acagctcctg acgtgccttc  1200
cgagccagtg actactcctc caggaagtgg gagtgggggt ggaagctccg gaggaagctc  1260
tggaggcagt ggattctgtg ccgacaaagc agatggcctc taccctgtgg cagatgacag  1320
aaatgctttt tggcagtgca tcaatggaat cacataccag cagcattgtc aagcagggct  1380 tgttttttgat accagctgta attgctgcaa ctggccatga acctaatgcc attcttccag  1440
aaatttctgc actctccttt actcctcacc aaaagtaact atcttccctt taaccttatg  1500
caataaaatt ggtagccaaa acaaaaaaaa aaaaaaaa                          1538
```

TABLE 14

ClustalW of Nearest Neighbors: nucleotides

| SEQ ID NO: | Name | Reference | bp |
|---|---|---|---|
| Residues 30-1354 of 6 | Human eosinophil chemotactic-like cytokine (HsEosChemokineNM021797) | NM_021797 | 1354 |
| Residues 301-1625 of 8 | Human mammalian acidic chitinase precursor (HsAMCaseprecAF290004.1) | AF290004.1 | 1625 |
| 1 | Acidic Mammalian Molecule/L0E1167.4 (1.3610e1167.4cgmm10e1167.4_376EXT) | SEQ ID NO:1 | 319 |
| Residues 200-1530 of 9 | Mammalian chitinase precursor (1.36GBaf290003Mmchitinaseprecu) | AAG60019 | 1530 |
| Residues 196-1538 of 10 | Mammalian chemokine (1.36GBbc011134Mmchemokine) | BC011134 | 1538 |

TABLE 14-continued

ClustalW of Nearest Neighbors: nucleotides

```
1.3610E1167.4cgmm10e1167.4_376   ------------------------------------------------------------
1.36GBbc011134Mmehemokine        CACCACCATAGAATGGAATGATGTTACTCTCTATAAAGCTTTCAATGACTTGAAAAACAG
1.36GBaf290003Mmchitinaseprecu   CACCACCATAGAATGGAATGATGTTACTCTCTATAAAGCTTTCAATGACTTGAAAAACAG
HsEosChemokineNM021797           GGCCGACTCTGGAGCCCAGGCTGTTGCTTTCAGTCTGGTGGTGAATCCTCCATAGTCTG
HsAMCaseprecAF290004.1           CACCACCATCGAATGGAACGATGTGACTCTCTACCAAGCTTTCAATGGCCTGAAAAATAA 1.3610e1167.4cgmm10e1167.4_376   ------------------------------------------------------------
1.36GBbc011134Mmehemokine        GAACAGCAAACTGAAAACCCTCCTGGCAATTGGAGGCTGGAACTTTGGAACTGCTCCTTT
1.36GBaf290003Mmchitinaseprecu   GAACAGCAAACTGAAAACCCTCCTGGGAATTGGAGGCTGGAACTTTGGAACTGCTCCTTT
HsEosChemokineNM021797           GAACAGCCAGCTGAAAACTCTCCTGGCCATTGGAGGCTGGAAGTTCAGGACTGCCCCTTT
HsAMCaseprecAF290004.1           GAACAGCCAGCTGAAAACTCTCCTGGCCATTGGAGGCTGGAACTTCGGGACTGCCCCTTT 1.3610e1167.4cgmm10e1167.4_376   ------------------------------------------------------------
1.36GBbc011134Mmehemokine        CACTACCATGGTTTCCACTTCTCAGAACCGCCAGACCTTCATTACCCTCAGTGATGAAATT
1.36GBaf290003Mmchitinaseprecu   CACTACCATGGTTTCCACTTCTCAGAACCGCCAGACCTTCATTACCCTCAGTCATCAAATT
HsEosChemokineNM021797           CACTGCCATGGTTTCTACTCCTGAGAACCGCCAGACTTTCATCACCTCAGTCATGAAATT
HsAMCaseprecAF290004.1           CACTGCCATGGTTTCTACTCCTGAGAACCGCCAGACTTTCATCACCTCAGTCATCAAATT 1.3610e1167.4cgmm10e1167.4_376   ------------------------------------------------------------
1.36GBbc011134Mmehemokine        TCTGCGTCAGTATGGGTTTGATGGACTGGACCTGGACTGGGAATACCCAGGCTCACGTGG
1.36GBaf290003Mmchitinaseprecu   TCTGCCTCAGTATGGGTTTGATGGACTGGACCTGGACTGGGAATACCCAGGCTCACGTGG
HsEosChemokineNM021797           CCTGCGCCAGTATGAGTTTGACGGGCTGGACTTTGACTGGGAGTACCCTGGCTCTCGTGG
HsAMCaseprecAF290004.1           CCTGCGCCAGTATGAGTTTGACGGGCTGGACTTTGACTGGGAGTACCCTGGCTCTCGTGG 1.3610e1167.4cgmm10e1167.4_376   ------------------------------------------------------------
1.36GBbc011134Mmehemokine        GAGCCCTCCTCAGGACAAGCATCTCTTCACTGTCCTGGTCAAGGAAATGCGTGAAGCTTT
1.36GBaf290003Mmchitinaseprecu   GAGCCCTCCTCAGGACAAGCATCTCTTCACTGTCCTGGTGAAGGAAATGCGTGAAGCTTT
HsEosChemokineNM021797           GAGCCCTCCTCAGGACAAGCATCTCTTCACTGTCCTGGTCCAGGAAATGCGTGAAGCTTT
HsAMCaseprecAF290004.1           GAGCCCTCCTCAGGACAAGCATCTCTTCACTGTCCTGGTCCAGGAAATGCGTGAAGCTTT 1.3610e1167.4cgmm10e1167.4_376   ------------------------------------------------------------
1.36GBbc011134Mmehemokine        TGAGCAGGAGGCTATTGAGAGCAACAGGCCCAGACTGATGGTTACTGCTGCTGTAGCTGG
1.36GBaf290003Mmchitinaseprecu   TGAGCAGGAGGCTATTGAGAGCAACAGGCCCAGACTGATGGTTACTGCTGCTGTAGCTGG
HsEosChemokineNM021797           TGAGCAGGAGGCCAAGCAGATCAACAAGCCCAGGCTGATGGTCACTGCTGCAGTAGCTGC
HsAMCaseprecAF290004.1           TGAGCAGGAGGCCAAGCAGATCAACAAGCCCAGGCTGATGGTCACTGCTGCAGTAGCTGC 1.3610e1167.4cgmm10e1167.4_376   ------------------------------------------------------------
1.36GBbc011134Mmehemokine        TGGGATTTCCAACATCCAGCTGGCTATGAGATCCCTGAAGTTTCTAAGTACCTGGATTT
1.36GBaf290003Mmchitinaseprecu   TGGGATTTCCAACATCCAGCTGGCTATGAGATCCCTGAACTTTCTAAGTACCTGGATTT
HsEosChemokineNM021797           TGGCATCTCCAATATCCAGTCTGGCTATGAGATCCCCCAACTGTCACAGTACCTGGACTA
HsAMCaseprecAF290004.1           TGGCATCTCCAATATCCAGTCTGGCTATGAGATCCCCCAACTGTCACAGTACCTGGACTA 1.3610e1167.4cgmm10e1167.4_376   ------------------------------------------------------------
1.36GBbc011134Mmehemokine        CATCCATGTCATGACATATGACCTCCATGGCTCCTGGGAGGGCTACACTGGGGAGAATAG
1.36GBaf290003Mmchitinaseprecu   CATCCATGTCATGACATATGACCTCCATGGCTCCTGGGAGGGCTACACTGGGGAGAATAG
HsEosChemokineNM021797           CATCCATGTCATGACCTACGACCTCCATGGCTCCTGGGAGGGCTACACTGGAGAGAACAG
HsAMCaseprecAF290004.1           CATCCATGTCATGACCTACGACCTCCATGGCTCCTGGGAGGGCTACACTGGAGAGAACAG 1.3610e1167.4cgmm10e1167.4_376   ------------------------------------------------------------
1.36GBbc011134Mmehemokine        TCCTCTTTACAAATACCCTACTGAGACTGGTAGCAATGCCTACCTCAATGTGGATTATGT
1.36GBaf290003Mmchitinaseprecu   TCCTCTTTACAAATACCCTACTGAGACTGGTAGCAATGCCTACCTCAATGTGGATTATGT
HsEosChemokineNM021797           CCCCCTCTACAAATACCCGACTGACACCGGCAGCAACGCCTACCTCAATGTGGATTATGT
HsAMCaseprecAF290004.1           CCCCCTCTACAAATACCCGACTGACACCGGCAGCAACGCCTACCTCAATGTGGATTATGT 1.3610e1167.4cgmm10e1167.4_376   ------------------------------------------------------------
1.36GBbc011134Mmehemokine        CATGAACTATTGGAAGAACAATGGACCCCAGCTGAGAAGCTCATTGTTGGATTCCCAGA
1.36GBaf290003Mmchitinaseprecu   CATGAACTATTGGAAGAACAATGGACCCCAGCTGAGAAGCTCATTGTTGGATTCCCAGA
HsEosChemokineNM021797           CATGAACTACTGGAAGACAATGGAGCACCACCTGAGAAGCTCATCGTTGGATTCCCTAC
HsAMCaseprecAF290004.1           CATGAACTACTGGAAGACAATGGAGCACCACCTGAGAAGCTCATCGTTGGATTCCCTAC
```

TABLE 14-continued

ClustalW of Nearest Neighbors: nucleotides

```
1.3610e1167.4cgmm10e1167.4_376   ----------------------------------------------------------
1.36GBbc011134Mmehemokine        GTATGGACACACCTTCATCCTGAGAAACCCCTCTGATAATGGAATTGGTGCCCCTACCTC
1.36GBaf290003Mmchitinaseprecu   GTATGGACACACCTTCATCCTGAGAAACCCCTCTGATAATGGAATTGGTGCCCCTACCTC
HsEosChemokineNM021797           CTATGGACACAACTTCATCCTGAGCAACCCCTCCAACACTGGAATTGGTGCCCCCACCTC
HsAMCaseprecAF290004.1           CTATGGACACAACTTCATCCTGAGCAACCCCTCCAACACTGGAATTGGTGCCCCCACCTC 1.3610e1167.4cgmm10e1167.4_376   ----------------------------------------------------------
1.36GBbc011134Mmehemokine        TGGTGATGGCCCTGCTGGCGCCTATACCAGACAGGCTGGGTTCTGGGCCTACTATGAGAT
1.36GBaf290003Mmchitinaseprecu   TGGTGATGGCCCTGCTGGCGCCTATACCAGACAGGCTGGGTTCTGGGCTACTATGAGAT
HsEosChemokineNM021797           TGGTGCTGGTTCTGCTGGGCCCTATGCCAAGGAGTCTGGGATCTGGGCTTACTACGAGAT
HsAMCaseprecAF290004.1           TGGTGCTGGTTCTGCTGGGCCCTATGCCAAGGAGTCTGGGATCTGGGCTTACTACGAGAT 1.3610e1167.4cgmm10e1167.4_376   ----------------------------------------------------------
1.36GBbc011134Mmehemokine        TTGCACCTTTCTGAGAAGTGGAGCCACTGAGGTCTGGGATGCCTCCCAAGAAGTGCCCTA
1.36GBaf290003Mmchitinaseprecu   TTGCACCTTTCTGAGAAGTGGAGCCACTGAGGTCTGGGATGCCTCCCAAGAAGTGCCCTA
HsEosChemokineNM021797           CTGTACCTTCCTGAAAAATGGAGCCACTCAGGGATGGGATGCCCCTCAGGAAGTGCCTTA
HsAMCaseprecAF290004.1           CTGTACCTTCCTGAAAAATGGAGCCACTCAGGGATGGGATGCCCCTCAGGAAGTGCCTTA 1.3610e1167.4cgmm10e1167.4_376   ----------------------------------------------------------
1.36GBbc011134Mmehemokine        TGCCTATAAGGCCAACGAGTGGCTTGGCTATGACAATATCAAGAGCTTCAGTGTTAAGGC
1.36GBaf290003Mmchitinaseprecu   TGCCTATAAGGCCAACGAGTGGCTTGGCTATGACAATATCAAGAGCTTCAGTGTTAAGGC
HsEosChemokineNM021797           TGCCTATCAGGGCAATGTGTGGGTTGGCTATGACAACGTCAAGAGCTTCGATATTAAGGC
HsAMCaseprecAF290004.1           TGCCTATCAGGGCAATGTGTGGGTTGGCTATGACAACGTCAAGAGCTTCGATATTAAGGC 1.3610e1167.4cgmm10e1167.4_376   ----------------------------------------------------------
1.36GBbc011134Mmehemokine        TCAGTGGCTTAAGCAGAACAATTTTGGAGGTGCCATGATCTGGGCCATTGACCTTGATGA
1.36GBaf290003Mmchitinaseprecu   TCAGTGGCTTAAGCAGAACAATTTTGGAGGTGCCATGATCTGGGCCATTGACCTTGATGA
HsEosChemokineNM021797           TCAATGGCTTAAGCACAACAAATTTGGAGGCGCCATGGTCTGGGCCATTGATCTGGATGA
HsAMCaseprecAF290004.1           TCAATGGCTTAAGCACAACAAATTTGGAGGCGCCATGGTCTGGGCCATTGATCTGGATGA 1.3610e1167.4cgmm10e1167.4_376   ----------------------------------------------------------
1.36GBbc011134Mmehemokine        CTTCACTGGCTCTTTCTGTGCATCAGGGAAAATTTCCTCTGACTTCTACTTTGAACAAAGC
1.36GBaf290003Mmchitinaseprecu   CTTCACTGGCTCTTTCTGTGCATCAGGGAAAATTTCCTCTGACTTCTACTTTGAACAAAGC
HsEosChemokineNM021797           CTTCACTGGCACTTTCTGCAACCAGGGCAAGTTTCCCTAATCTCCACCCTGAAGAAGGC
HsAMCaseprecAF290004.1           CTTCACTGGCACTTTCTGCAACCAGGGCAAGTTTCCCTAATCTCCACCCTGAAGAAGGC 1.3610e1167.4cgmm10e1167.4_376   ----------------------------------------------------------
1.36GBbc011134Mmehemokine        CCTTGGCATATCCACTGAAGGTTGCACAGCTCCTGACGTGCCTTCCGAGCCAGTGACTAC
1.36GBaf290003Mmchitinaseprecu   CCTTGGCATATCCACTGAAGGTTGCACAGCTCCTGACGTGCCTTCCGAGCCAGTGACTAC
HsEosChemokineNM021797           CCTTGGCCTGCAGAGTGCAAGTTGCACGGCTCCAGCTCAGCCCATTGAGCCAATAACTGC
HsAMCaseprecAF290004.1           CCTTGGCCTGCAGAGTGCAAGTTGCACGGCTCCAGCTCAGCCCATTGAGCCAATAACTGC 1.3610e1167.4cgmm10e1167.4_376   -----------GTAG--GAAGTGAGAGTGGGCGTGGAAGCTTCCGGAGGAAGCTTTGGAG
1.36GBbc011134Mmehemokine        TCCT-------CCAG--GAAGTGGGAGTGGGCGTGCAAGCT-CCGGAGGCAAGCTCTGGAG
1.36GBaf290003Mmchitinaseprecu   TCCT-------CCAG--GAAGTGGGAGTGGGCGTGCAAGCT-CCGGAGGCAAGCTCTGGAG
HsEosChemokineNM021797           TGCTCCCAGTGGCAGCGGGAACGGGAGCGGCAGTACAGCT-CTGGAGCCAGCTCGGGAG
HsAMCaseprecAF290004.1           TGCTCCCAGTGGCAGCGGGAACGGGAGCGGCAGTACAGCT-CTGGAGCCAGCTCGGGAG 1.3610e1167.4cgmm10e1167.4_376   GCAGTGGATTTTGTGCCGACAAAGGAGATGGCCTTTACCCTGTGGCAGATGACAGAAATG
1.36GBbc011134Mmehemokine        GCAGTGGATTCTGTGCCGACAAAGGAGATGGCCTCTACCCTGTGGCACATGACAGAAATG
1.36GBaf290003Mmchitinaseprecu   GCAGTGGATTCTGTGCCGACAAAGGAGATGGCCTCTACCCTGTGGCACATGACAGAAATG
HsEosChemokineNM021797           GCAGTGGATTCTGTGCTGCAGAACCAACGGCCTCTACCCGTGGGAAATAACAGAAATG
HsAMCaseprecAF290004.1           GCAGTGGATTCTGTGCTGCAGAACCAACGGCCTCTACCCGTGGGAAATAACAGAAATG 1.3610e1167.4cgmm10e1167.4_376   CTTTTTGGCAGTGCATCAATGGAATCACATACCAGCAGCATTGTCAAGCAGGGCTTGTTT
1.36GBbc011134Mmehemokine        CTTTTTGGCAGTGCATCAATGGAATCACATACCAGCAGCATTGTCAAGCAGGGCTTGTTT
1.36GBaf290003Mmchitinaseprecu   CTTTTTGGCAGTGCATCAATGGAATCACATACCAGCAGCATTGTCAAGCAGGGCTTGTTT
HsEosChemokineNM021797           CCTTCTGGCACTGCGTGAATGAGTCACGTACCAGCAGAACTGCCAGGCCGGGCTTGTCT
HsAMCaseprecAF290004.1           CCTTCTGGCACTGCGTGAATGAGTCACGTACCAGCAGAACTGCCAGGCCGGGCTTGTCT 1.3610e1167.4cgmm10e1167.4_376   TTGATACCAGCTGTAATTGCTGCAACTGGCCATGAACCTAT----GCCATTTTTCCAGAA
1.36GBbc011134Mmehemokine        TTGATACCAGCTGTAATTGCTGCAACTGGCCATGAACCTAAT---GCCATTTTTCCAGAA
1.36GBaf290003Mmchitinaseprecu   TTGATACCAGCTGTAATTGCTGCAACTGGCCATGAACCTAAT---GCCATTTTTCCAGAA
HsEosChemokineNM021797           TCGACACCAGCTGTGATTGCTGCAACTGGGCATAAACCTGACCTGGTCTATATTCCCTAG
HsAMCaseprecAF290004.1           TCGACACCAGCTGTGATTGCTGCAACTGGGCATAAACCTGACCTGGTCTATATTCCCTAG 1.3610e1167.4cgmm10e1167.4_376   ATTTTTGCATTTTCCTTTATTCCTCACCAAAAGTAACTTTTTTCCCTTTAACCTTATGCA
1.36GBbc011134Mmehemokine        ATTTCTGCACTCTCCTTTACTCCTCACCAAAAGTAACATATCTTCCCTTTAACCTTATGCA
1.36GBaf290003Mmchitinaseprecu   ATTTCTGCACTCTCCTTTACTCCTCACCAAAAGTAACATATCTTCCCTTTAACCTTATGCA
HsEosChemokineNM021797           AGTTC---CAGTCTCTTT----TGCTTAGGACATGTTGCCC-CTACC---T-AAAGTCCTGCA
HsAMCaseprecAF290004.1           AGTTC---CAGTCTCTTT----TGCTTAGGACATGTTGCCC-CTACC---T-AAAGTCCTGCA 1.3610e1167.4cgmm10e1167.4_376   ATAAAATTGGTAGCCGTAAAAAAAAAAAAAAAAAA-
1.36GBbc011134Mmehemokine        ATAAAATTGGTAGCCAAAACAAAAAAAAAAAAAAAA
1.36GBaf290003Mmchitinaseprecu   ATAAAATTGGTAGCCAAAACAAAA------------
HsEosChemokineNM021797           ATAAAATCAGCAGTC---------------------
HsAMCaseprecAF290004.1           ATAAAATCAGCAGTC---------------------
```

CLUSTALW software was also used to determine nearest neighbors of the novel acidic mammalian molecule protein sequence, as well as to determine where the sequences align, mismatch or have gaps. In this analysis (Table 15) the following sequences were compared: mouse AMCase (1.36Q99PH2) (SEQ ID NO:11), mouse eosinophil chemotactic-like cytokine (1.36AAH11134) (SEQ ID NO:4), novel human chitinase (1.36Q9ULY4) (SEQ ID NO:13), human AMCase precursor (1.36Q9BZP6) (SEQ ID:5), and novel acidic mammalian molecule protein sequence (1.3610e1167.4cgmm10e1167.4_37627_215_EXT) (SEQ ID NO:2). Highly conserved regions (black) suggest those regions of the polypeptide that are most important for function. The sequence type was set specifically to protein and the sequence format was Pearson.

TABLE 15

Sequences used in CLUSTALW Protein Analysis

| Sequences | SEQ ID NO: |
|---|---|

Sequences analyzed:

1. 1.36Q99PH2MmAMCase
2. 1.36AAH11134MmEosChemo
3. 1.36Q9ULY4HsNovChitinase
4. 1.36Q9BZP6HsAMCasePrec
5. 1.3610e1167.4cgmml0e1167.4_37627_215_EXT Clustal Details:

CLUSTAL W (1.7) Multiple Sequence Alignments
Sequence type explicitly set to Protein
Sequence format is Pearson
Sequence 1: 1.36Q99PH2MmAMCase        473 aa  11
Sequence 2: 1.36AAH11134MmEosChemo    365 aa  4
Sequence 3:                           368 aa  13
1.36Q9ULY4HsNovChitinase
Sequence 4: 1.36Q9BZP6HsAMCasePrec    476 aa  5
Sequence 5:                            65 aa  2
1.3610e1167.4cgmml0e1167.4_376

Multiple Alignment:

```
1 36Q99PH2MmAMCase              1    MAKLLLVTGLALLLNAQLGSAYNLICYFTNWAQYRPGLGSFKPDDINPCLCTHLIYAFAG    60
1 36aaH11134MmEosChemo          ***  ------------------------------------------------------------    ***
1 3610e11674cgmml0311674_376    ***  ------------------------------------------------------------    ***
1 36Q9ULY4HsNovChitmase         ***  ------------------------------------------------------------    ***
1 36Q9BZP6HsAMCasePrec          1    MTKLILLTGLVLILNLQLGSAYQLTCYFTNWAQYRPGLGRFMPDNIDPCLCTHLIYAFAG    60

1 36Q99PH2MmAMCase              61   MQNNEITTIEWNDVTLYKAFNDLKNRNSKLKTLLAIGGWNFGTAPFTTMVSTSQNRQTFI   120
1 36aaH11134MmEosChemo          1    ------------------------------------------------MVSTSQNRQTFI    12
1 3610e11674cgmml0311674_376    ***  ------------------------------------------------------------    ***
1 36Q9ULY4HsNovChitinase        1    ------------------------------------------------MVSTPENRQTFI    12
1 36Q9BZP6HsAMCasePrec          61   RQNNEITTIEWNDVTLYQAFNGLKNKNSQLKTLLAIGGWNFGTAPFTAMVSTPENRQTFI   120

1 36Q99PH2MmAMCase              121  TSVIKFLRQYGFLGLCLDWEYFGSRGSPPQDKHLFTVLVKEMREAFQEAIESNRPRLMV   180
1 36aaH11134MmEosChemo          13   TSVIKFLRQYGFLGLCLDWEYFGSRGSPPQDKHLFTVLVKEMREAFQEAIESNRPRLMV    72
1 3610e11674cgmml0311674_376    ***  ------------------------------------------------------------    ***
1 36Q9ULY4HsNovChitmase         13   TSVIKFLRQYEFLGLCFDWEYFGSRGSPPQDKHLFTVLVQEMREAFQEAKQINKPRLMV    72
1 36Q9BZP6HsAMCasePrec          121  TSVIKFLRQYEFLGLCFDWEYFGSRGSPPQDKHLFTVLVQEMREAFQEAKQINKPRLMV   180

1 36Q99PH2MmAMCase              181  TAAVAGGISNIQAGYEIPELSKVLDFIHVMTYDLGHSWEGYTGENSPLYKYPTETGSNAY   240
1 36aaH11134MmEosChemo          73   TAAVAGGISNIQAGYEIPELSKVLDFIHVMTYDLGHSWEGYTGENSPLYKYPTETGSNAY   132
1 3610e11674cgmml0311674_376    ***  ------------------------------------------------------------    ***
1 36Q9ULY4HsNovChitmase         73   TAAVAAGISNIQSGYEIPQLSQVLDYIHVMTYDLGHSWEGYTGENSPLYKYPTDTGSNAY   132
1 36Q9BZP6HsAMCasePrec          181  TAAVAAGISNIQSGYEIPQLSQVLDYIHVMTYDLGHSWEGYTGENSPLYKYPTDTGSNAY   240

1 36Q99PH2MmAMCase              241  LNVDYVMNYWKNNGAPAEKLIVGFPEYGHTFILRNPSDNGIGAPTSGDGPAGATRQAGF   300
1 36aaH11134MmEosChemo          133  LNVDYVMNYWKNNGAPAEKLIVGFPEYGHTFILRNPSDNGIGAPTSGDGPAGYTRQAGF   192
1 3610e11674cgmml0311674_376    ***  ------------------------------------------------------------    ***
1 36Q9ULY4HsNovChitmase         133  LNVDYVMNYWKDNGAPAEKLIVGFPTYGHNFILSNPSNTGIGAPTSGAGPAGPYAKESGI   192
1 36Q9BZP6HsAMCasePrec          241  LNVDYVMNYWKDNGAPAEKLIVGFPTYGHNFILSNPSNTGIGAPTSGAGPAGPYAKESGI   300

1 36Q99PH2MmAMCase              301  WAYYEICTFLRSGATEVWDASDEVPYAYKANEWLGYDNIKSESVKAQWLKQNNFGGAMI   360
1 36aaH11134MmEosChemo          193  WAYYEICTFLRSGATEVWDASDEVPYAYKANEWLGYDNIKSESVKAQWLKQNNFGGAMI   252
1 3610e11674cgmml0311674_376    ***  ------------------------------------------------------------    ***
1 36Q9ULY4HsNovChitmase         193  WAYYEICTFLKNGATQGWDAPDEVPYAYQGNVWVGYDNIKSEDIKAQWLKHNKFGGAMV   252
1 36Q9BZP6HsAMCasePrec          301  WAYYEICTFLKNGATQGWDAPDEVPYAYQGNVWVGYDNIKSEDIKAQWLKHNKFGGAMV   360
```

TABLE 15-continued

Sequences used in CLUSTALW Protein Analysis

| 1 | 36Q99PH2MmAMCase | 361 | AIDLDDFTGSFGDQGKFPLTSTTNKALGISTEGSTAEDVESEPVTTPP---GSGSGGGS | 417 |
|---|---|---|---|---|
| 1 | 36aaH11134MmEosChemo | 253 | AIDLDDFTGSFGDQGKFPLTSTTNKALGISTEGSTAEDVESEPVTTPP---GSGSGGGS | 309 |
| 1 | 3610e11674cgmml0311674_376 | 1 | ------------------------------------------EVRVGVEA | 9 |
| 1 | 36Q9ULY4HsNovChitmase | 253 | AIDLDDFTGTFGNQGKFPLISTTKKALGLQSASSTAEAQEIEEITAAESGSGNGSGSSS | 312 |
| 1 | 36Q9BZP6HsAMCasePrec | 361 | AIDLDDFTGTFGNQGKFPLISTTKKALGLQSASSTAEAQEIEEITAAESGSGNGSGSSS | 420 |
| 1 | 36Q99PH2MmAMCase | 418 | GGSSGGSGFCADKADGLYPVADDRNAFWQCINGITYQQHGQAGLVFDTSCNCCNWP | 473 |
| 1 | 36aaH11134MmEosChemo | 310 | GGSSGGSGFCADKADGLYPVADDRNAFWQCINGITYQQHGQAGLVFDTSCNCCNWP | 365 |
| 1 | 3610e11674cgmml0311674_376 | 10 | GGSFGGSGFCADKADGLYPVADDRNAFWQCINGITYQQHGQAGLVFDTSCNCCNWP | 65 |
| 1 | 36Q9ULY4HsNovChitmase | 313 | GGSSGGSGFCAGRANGLYPVANNRNAFWHCVNGITYQQNGQAGLVFDTSCDCCNWA | 368 |
| 1 | 36Q9BZP6HsAMCasePrec | 421 | GGSSGGSGFCAVRANGLYPVANNRNAFWHCVNGITYQQNGQAGLVFDTSCDCCNWA | 476 |

Practicing the Invention

Unless defined otherwise, all technical and scientific terms have the same meaning as is commonly understood by one of skill in the art to which this invention belongs. The definitions below are presented for clarity.

"Isolated," when referred to a molecule, refers to a molecule that has been identified and separated and/or recovered from a component of its natural environment. Contaminant components of its natural environment are materials that interfere with diagnostic or therapeutic use.

Polynucleotides

Probes

Probes are polynucleotide sequences of variable length, preferably between at least about 10 nucleotides (nt), 100 nt, or many (e.g., 6,000 nt) depending on the specific use. Probes are used to detect identical, similar, or complementary polynucleotide sequences. Longer length probes can be obtained from a natural or recombinant source, are highly specific, and much slower to hybridize than shorter-length oligomer probes. Probes may be single- or double-stranded and designed to have specificity in PCR, membrane-based hybridization technologies, or ELISA-like technologies. Probes are substantially purified oligonucleotides that will hybridize under stringent conditions to at least optimally 12, 25, 50, 100, 150, 200, 250, 300, 350 or 400 consecutive sense strand nucleotide sequence of SEQ ID NO:1; or an anti-sense strand nucleotide sequence of SEQ ID NO:1; or of naturally-occurring mutants of SEQ ID NO:1.

The full- or partial length native sequence AMM may be used to "pull out" similar (homologous) sequences (Ausubel et al., 1987; Sambrook, 1989), such as: (1) full-length or fragments of AMM cDNA from a cDNA library from any species (e.g. human, murine, feline, canine, bacterial, viral, retroviral, or yeast), (2) from cells or tissues, (3) variants within a species, and (4) homologs, orthologues and variants from other species. To find related sequences that may encode related genes, the probe may be designed to encode unique sequences or degenerate sequences. Sequences may also be AMM genomic sequences including promoters, enhancer elements and introns.

For example, AMM coding region in another species may be isolated using such probes. A probe of about 40 bases is designed, based on mouse AMM (mAMM; SEQ ID NO:2), and made. To detect hybridizations, probes are labeled using, for example, radionuclides such as $^{32}P$ or $^{35}S$, or enzymatic labels such as alkaline phosphatase coupled to the probe via avidin-biotin systems. Labeled probes are used to detect polynucleotides having a complementary sequence to that of mAMM in libraries of cDNA, genomic DNA or mRNA of a desired species.

Probes can be used as a part of a diagnostic test kit for identifying cells or tissues which mis-express an AMM, such as by measuring a level of an AMM in a sample of cells from a subject e.g., detecting AMM mRNA levels or determining whether a genomic AMM has been mutated or deleted. Probes are also useful in arrays that allow for the simultaneous examination of multiple sequences.

Control Sequences

Control sequences are DNA sequences that enable the expression of an operably-linked coding sequence in a particular host organism. Prokaryotic control sequences include promoters, operator sequences, and ribosome binding sites. Eukaryotic cells utilize promoters, polyadenylation signals, and enhancers.

Operably-linked

Polynucleotide is operably-linked when placed into a functional relationship with another polynucleotide sequence. For example, a promoter or enhancer is operably-linked to a coding sequence if it affects the transcription of the sequence, or a ribosome-binding site is operably-linked to a coding sequence if positioned to facilitate translation. Generally, "operably-linked" means that the DNA sequences being linked are contiguous, and, in the case of a secretory leader, contiguous and in reading phase. However, enhancers do not have to be contiguous. Linking can be accomplished by conventional recombinant DNA methods.

Isolated Polynucleotides

An isolated polynucleotide molecule is purified from the setting in which it is naturally found and is separated from at least one contaminant polynucleotide molecule. Isolated AMM molecules are distinguished from the specific AMM molecule in cells. However, an isolated AMM molecule includes AMM molecules contained in cells that ordinarily express AMM where, for example, the polynucleotide molecule is in a chromosomal location different from that of natural cells.

Oligonucleotides

An oligonucleotide comprises a series of linked nucleotide residues, which oligonucleotide has a sufficient number of nucleotide bases to be useful, such as in PCR reactions or as probes. A short oligonucleotide sequence may be based on, or designed from, a genomic or cDNA AMM sequence and is used to amplify, confirm, or reveal the presence of an identical, similar or complementary DNA or RNA in a particular cell or tissue. Oligonucleotides comprise portions of a polynucleotide sequence having about 10 nt, 50 nt, or 100 nt in length, preferably about 15 nt to 30 nt in length. An oligonucleotide comprising a polynucleotide molecule less than 100 nt in length would further comprise at least 6 contiguous nucleotides of SEQ ID NO:1, or complements thereof. Oligonucleotides may be chemically synthesized.

Complementary Polynucleotide Sequences; Binding

In another embodiment, an isolated polynucleotide molecule of the invention comprises a polynucleotide molecule that is a complement of the nucleotide sequence shown in SEQ ID NO:1, or a portion of these sequences (e.g., fragments that can be used as a probes, primers or fragments encoding a biologically-active portion of an AMM). A polynucleotide molecule that is complementary to the nucleotide sequence shown in SEQ ID NO:1, is one that is sufficiently complementary to the nucleotide sequence shown in SEQ ID NO:1, that it can hydrogen bond with little or no mismatches to the nucleotide sequence shown in SEQ ID NO:1, thereby forming a stable duplex.

"Complementary" refers to Watson-Crick or Hoogsteen base-pairing between nucleotides of a polynucleotide molecule. "Binding" means the physical or chemical interaction between two polypeptides or compounds, or associated polypeptides, or compounds or combinations thereof. Binding includes ionic, non-ionic, van der Waals and hydrophobic interactions. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Fragments are at least 6 contiguous polynucleotides or at least 4 contiguous amino acids, sufficient lengths to allow for specific hybridization in the case of polynucleotides or for specific recognition of an epitope in the case of amino acids, respectively, and are at most some portion less than a full-length sequence. Fragments may be derived from any contiguous portion of a polynucleotide or amino acid sequence of choice.

Derivatives and Analogs

Derivatives are polynucleotide sequences or amino acid sequences formed from native compounds either directly, by modification or partial substitution. Analogs are polynucleotide sequences or amino acid sequences that have a structure similar to, but not identical, the native compound but differ from it in respect to certain components or side chains. Analogs may be synthetic or from a different evolutionary origin and may have a similar or opposite metabolic activity compared to wild type. Homologs are polynucleotide sequences or amino acid sequences of a particular gene that are derived from different species.

Derivatives and analogs may be full length or other than full length, if the derivative or analog contains a modified polynucleotide or amino acid. Derivatives or analogs of the polynucleotides or polypeptides of the invention include, but are not limited to, molecules comprising regions that are substantially homologous to AMM polynucleotides or polypeptides by at least about 70%, 80%, or 95% identity (with a preferred identity of 80%, 81%, 82%, 83%, 84%, 85%, 86%, 87%, 88%, 89%, 90%, 91%, 92%, 93%, 94%, 95%) over a polynucleotide or amino acid sequence of identical size or when compared to an aligned sequence in which the alignment is done by a well-known algorithm in the art, or whose encoding polynucleotide is capable of hybridizing to the complement of a sequence encoding the aforementioned polypeptides under stringent, moderately stringent, or low stringent conditions (Ausubel et al., 1987).

Homology

A "homologous polynucleotide sequence" or "homologous amino acid sequence," or variations thereof, refer to sequences characterized by a homology at the nucleotide or amino acid level. Homologous nucleotide sequences encode those sequences coding for isoforms of AMM. Isoforms can be expressed in different tissues of the same organism as a result of, for example, alternative splicing. Alternatively, different genes can encode isoforms. Homologous AMM nucleotide sequences may be of a species other than mice, including other vertebrates, such as human, frog, rat, rabbit, dog, cat, cow, horse, and other organisms. Homologous nucleotide sequences also include naturally-occurring allelic variations and mutations of SEQ ID NO:1. A homologous nucleotide sequence does not, however, include the exact nucleotide sequence encoding mouse AMMs. Homologous polynucleotide sequences may encode conservative amino acid substitutions (see below) in SEq ID NO:2, as well as a polypeptide possessing AMM biological activity.

Open Reading Frames

The open reading frame (ORF) of an AMM gene encodes AMM. An ORF is a nucleotide sequence that has a start codon (ATG) and terminates with one of the three "stop" codons (TAA, TAG, or TGA). In this invention, however, an ORF may be any part of a coding sequence that may or may not comprise a start codon and a stop codon. To achieve a unique sequence, preferable AMM ORFs encode at least 50 amino acids.

Polypeptides

Polypeptide, Polypeptides and Peptides

A polypeptide has an amino acid sequence that is longer than a peptide. A peptide contains 2 to about 50 amino acid residues. "Polypeptide" includes polypeptides and peptides. Examples of polypeptides include antibodies, enzymes, lectins and receptors; lipopolypeptides and lipopolypeptides; and glycopolypeptides and glycopolypeptides. Examples of polypeptides include neuropeptides, functional domains (e.g. PDZ domains) of polypeptides, peptides having 3–20 residues obtained from phage display libraries, etc.

Mature

An AMM can encode a mature AMM. A "mature" form of a polypeptide or polypeptide is the product of a naturally-occurring polypeptide or precursor form or propolypeptide. The naturally-occurring polypeptide, precursor or propolypeptide includes the full-length gene product, encoded by the corresponding genomic sequence or open reading frame. The product "mature" form arises as a result of one or more processing steps as they may take place within the cell, or host cell, in which the gene product arises. Examples of such processing steps include cleavage of the N-terminal methionine residue encoded by the initiation codon of an open reading frame, or cleavage of the signal peptide or leader sequence. Thus a mature form arising from a precursor polypeptide or polypeptide that has residues 1 to n, where residue 1 is the N-terminal methionine, would have residues 2 through n after removal of the N-terminal methionine. Alternatively, a mature form arising from a precursor polypeptide or polypeptide having residues 1 to n in which an N-terminal signal sequence from residue 1 to residue m is cleaved, would have the residues from residue m+1 to residue n remaining. A "mature" form of a polypeptide or polypeptide may arise from other post-translational modifications, such as glycosylation, myristoylation or phosphorylation. In general, a mature polypeptide or polypeptide may result from the operation of only one of these processes, or a combination of any of them.

Purified Polypeptide

When the molecule is a purified polypeptide, the polypeptide will be purified (1) to obtain at least 15 residues of N-terminal or internal amino acid sequence using a sequenator, or (2) to homogeneity by SDS-PAGE under non-reducing or reducing conditions using Coomassie blue or silver stain. Isolated polypeptides include those expressed heterologously in genetically-engineered cells or expressed in vitro, since at least one component of the AMM natural environment is absent. Ordinarily, isolated polypeptides are prepared by at least one purification step.

Active Polypeptide

An active AMM or AMM fragment retains a biological and/or an immunological activity of native or naturally-occurring AMM. Immunological activity refers to the ability to induce the production of an antibody against an antigenic epitope possessed by a native AMM; biological activity refers to a function caused by a native AMM that excludes immunological activity. In addition, activity is further defined by the up-regulation of AMM expression during feeding, and its down-regulation during fasting.

Epitope Tags

An epitope tagged polypeptide refers to a chimeric polypeptide fused to a "tag polypeptide". Such tags provide epitopes against which Abs can be made or are available, but do not interfere with polypeptide activity. To reduce anti-tag Ab reactivity with endogenous epitopes, the tag polypeptide is preferably unique. Suitable tag polypeptides generally have at least six amino acid residues, usually between about 8 and 50 amino acid residues, preferably between 8 and 20 amino acid residues. Examples of epitope tag sequences include HA from Influenza A virus and FLAG.

AMM Polynucleotide Variants and Hybridization

Variant Polynucleotides, Genes and Recombinant Genes

The invention further encompasses polynucleotide molecules that differ from the nucleotide sequences shown in SEQ ID NO:1 due to degeneracy of the genetic code and thus encode same AMM as that encoded by the nucleotide sequences shown in SEQ ID NO:1. An isolated polynucleotide molecule of the invention has a nucleotide sequence encoding a polypeptide having an amino acid sequence shown in SEq ID NO:2.

In addition to the AMM sequences shown in SEQ ID NO:1, DNA sequence polymorphisms that change the AMM amino acid sequences may exist within a population. For example, allelic variations among individuals exhibit genetic polymorphisms in AMMs. The terms "gene" and "recombinant gene" refer to polynucleotide molecules comprising an open reading frame (ORF) encoding an AMM. Such natural allelic variations can typically result in 1–5% variance in AMM. Any and all such nucleotide variations and resulting amino acid polymorphisms in the AMM, which are the result of natural allelic variation and leave intact AMM functional activity are within the scope of the invention.

Moreover, AMM from other species that have a nucleotide sequence that differs from the sequence of SEQ ID NO:1 are contemplated. Polynucleotide molecules corresponding to natural allelic variants and homologs of AMM cDNAs can be isolated based on their homology to SEQ ID NO:1 using cDNA-derived probes to hybridize to homologous AMM sequences under stringent conditions.

"AMM variant polynucleotide" or "AMM variant polynucleotide sequence" means a polynucleotide molecule which encodes an active AMM that (1) has at least about 80% polynucleotide sequence identity with a nucleotide acid sequence encoding a full-length native AMM, (2) a full-length native AMM lacking the signal peptide, (3) an extracellular domain of an AMM, with or without the signal peptide, or (4) any other fragment of a full-length AMM. Ordinarily, an AMM variant polynucleotide will have at least about 80% polynucleotide sequence identity, more preferably at least about 81%, 82%, 83%, 84%, 85%, 86%, 87%, 88%, 89%, 90%, 91%, 92%, 93%, 94%, 95%, 96%, 97%, 98% polynucleotide sequence identity and yet more preferably at least about 99% polynucleotide sequence identity with the polynucleotide sequence encoding a full-length native AMM. An AMM variant polynucleotide may encode full-length native AMM lacking the signal peptide, an extracellular domain of an AMM, with or without the signal sequence, or any other fragment of a full-length AMM. Variants do not encompass the native nucleotide sequence.

Ordinarily, AMM variants are at least about 30 nucleotides, often at least about 60, 90, 120, 150, 180, 210, 240, 270, 300, 450, 600 nucleotides in length, more often at least about 900 nucleotides in length, or more.

"Percent (%) polynucleotide sequence identity" with respect to AMM-encoding polynucleotide sequences is defined as the percentage of nucleotides in the AMM sequence of interest that are identical with the nucleotides in a candidate sequence, after aligning the sequences and introducing gaps, if necessary, to achieve the maximum percent sequence identity. Alignment can be achieved in various ways well-known in the art; for instance, using publicly available software such as BLAST, BLAST-2, ALIGN or Megalign (DNASTAR) software. Those skilled in the art can determine appropriate parameters for measuring alignment, including any necessary algorithms to achieve maximal alignment over the full length of the sequences being compared.

When nucleotide sequences are aligned, the % polynucleotide sequence identity of a given polynucleotide sequence C to, with, or against a given polynucleotide sequence D (which can alternatively be phrased as a given polynucleotide sequence C that has or comprises a certain % polynucleotide sequence identity to, with, or against a given polynucleotide sequence D) can be calculated as follows:

$$\% \text{ polynucleotide sequence identity} = W/Z \cdot 100$$

where

W is the number of nucleotides scored as identical matches by the sequence alignment program's or algorithm's alignment of C and D and Z is the total number of nucleotides in D.

When the length of polynucleotide sequence C is not equal to the length of polynucleotide sequence D, the % polynucleotide sequence identity of C to D will not equal the % polynucleotide sequence identity of D to C.

Stringency

Homologs (i.e., polynucleotides encoding AMM derived from species other than human) or other related sequences (e.g., paralogs) can be obtained by low, moderate or high stringency hybridization with all or a portion of the particular human sequence as a probe using methods well known in the art for polynucleotide hybridization and cloning.

The specificity of single stranded DNA to hybridize complementary fragments is determined by the "stringency" of the reaction conditions. Hybridization stringency increases as the propensity to form DNA duplexes decreases. In polynucleotide hybridization reactions, the stringency can be chosen to either favor specific hybridizations (high stringency), which can be used to identify, for example, full-length clones from a library. Less-specific hybridizations (low stringency) can be used to identify related, but not exact, DNA molecules (homologous, but not identical) or segments.

DNA duplexes are stabilized by: (1) the number of complementary base pairs, (2) the type of base pairs, (3) salt concentration (ionic strength) of the reaction mixture, (4) the temperature of the reaction, and (5) the presence of certain organic solvents, such as formamide which decreases DNA duplex stability. In general, the longer the probe, the higher the temperature required for proper annealing. A common approach to achieve different stringencies is to vary the temperature: higher relative temperatures result in more stringent reaction conditions. Ausubel et al. (1987) provide guidance and an excellent explanation of stringency of hybridization reactions. To hybridize under "stringent conditions" describes hybridization protocols in which nucleotide sequences at least 60% homologous to each other remain hybridized.

(a) High Stringency

"Stringent hybridization conditions" conditions enable a probe, primer or oligonucleotide to hybridize only to its target sequence. Stringent conditions are sequence-dependent and will differ. Stringent conditions comprise: (1) low ionic strength and high temperature washes (e.g. 15 mM sodium chloride, 1.5 mM sodium citrate, 0.1% sodium dodecyl sulfate at 50° C.); (2) a denaturing agent during hybridization (e.g. 50% (v/v) formamide, 0.1% bovine serum albumin, 0.1% Ficoll, 0.1% polyvinylpyrrolidine, 50 mM sodium phosphate buffer (pH 6.5; 750 mM sodium chloride, 75 mM sodium citrate at 42° C.); or (3) 50% formamide. Washes typically also comprise 5×SSC (0.75 M NaCl, 75 mM sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. Preferably, the conditions are such that sequences at least about 65%, 70%, 75%, 85%, 90%, 95%, 98%, or 99% homologous to each other typically remain hybridized to each other.

(b) Moderate Stringency

"Moderately stringent conditions" use washing solutions and hybridization conditions that are less stringent (Sambrook, 1989), such that a polynucleotide will hybridize to the entire, fragments, derivatives or analogs of SEQ ID NO:1. One example comprises hybridization in 6×SSC, 5× Denhardt's solution, 0.5% SDS and 100 mg/ml denatured salmon sperm DNA at 55° C., followed by one or more washes in 1×SSC, 0.1% SDS at 37° C. The temperature, ionic strength, etc., can be adjusted to accommodate experimental factors such as probe length. Other moderate stringency conditions are described (Ausubel et al., 1987; Kriegler, 1990).

(c) Low Stringency

"Low stringent conditions" use washing solutions and hybridization conditions that are less stringent than those for moderate stringency (Sambrook, 1989), such that a polynucleotide will hybridize to the entire, fragments, derivatives or analogs of SEQ ID NO:1. An example of low stringency hybridization conditions is hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency, such as those for cross-species hybridizations are described (Ausubel et al., 1987; Kriegler, 1990; Shilo and Weinberg, 1981).

Conservative Mutations

In addition to naturally-occurring allelic variants of AMM, changes can be introduced by mutation into SEQ ID NO:1 that incur alterations in the amino acid sequences of AMM but do not alter AMM function. For example, nucleotide substitutions leading to amino acid substitutions at "non-essential" amino acid residues can be made in SEQ ID NO:2. A "non-essential" amino acid residue is a residue that can be altered from the wild-type sequences of the AMM without altering their biological activity, whereas an "essential" amino acid residue is required for biological activity. For example, amino acid residues that are conserved among the AMMs of the invention are predicted to be particularly non-amenable to alteration (Table 15).

Useful conservative substitutions are shown in Table A, "Preferred substitutions." Conservative substitutions whereby an amino acid of one class is replaced with another amino acid of the same type fall within the scope of the invention so long as the substitution does not materially alter the biological activity of the compound. If such substitutions result in a change in biological activity, then more substantial changes, indicated in Table B as exemplary are introduced and the products screened for AMM biological activity.

TABLE A

Preferred substitutions

| Original residue | Exemplary substitutions | Preferred substitutions |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

Non-conservative substitutions that effect (1) the structure of the polypeptide backbone, such as a β-sheet or α-helical conformation, (2) the charge or (3) hydrophobicity, or (4) the bulk of the side chain of the target site can modify AMM polypeptide function or immunological identity. Residues are divided into groups based on common side-chain properties as denoted in Table B. Non-conservative substitutions entail exchanging a member of one of these classes for another class. Substitutions may be introduced into conservative substitution sites or more preferably into non-conserved sites.

TABLE B

Amino acid classes

| Class | Amino acids |
|---|---|
| hydrophobic | Norleucine, Met, Ala, Val, Leu, Ile |
| neutral hydrophilic | Cys, Ser, Thr |
| acidic | Asp, Glu |
| basic | Asn, Gln, His, Lys, Arg |
| disrupt chain conformation | Gly, Pro |
| aromatic | Trp, Tyr, Phe |

The variant polypeptides can be made using methods known in the art such as oligonucleotide-mediated (site-directed) mutagenesis, alanine scanning, and PCR mutagenesis. Site-directed mutagenesis (Carter, 1986; Zoller and Smith, 1987), cassette mutagenesis, restriction selection mutagenesis (Wells et al., 1985) or other known techniques can be performed on the cloned DNA to produce AMM variants (Ausubel et al, 1987; Sambrook, 1989).

Anti-sense Polynucleotides

Using anti-sense and sense AMM oligonucleotides can prevent AMM polypeptide expression. These oligonucleotides bind to target polynucleotide sequences to form duplexes that block transcription or translation of the target sequence by enhancing degradation of the duplexes, terminating prematurely transcription or translation, or by other means.

Anti-sense or sense oligonucleotides are singe-stranded polynucleotides, often RNA or DNA, which can bind target AMM mRNA (sense) or AMM DNA (anti-sense) sequences. Anti-sense polynucleotides can be designed according to Watson and Crick or Hoogsteen base pairing rules. The anti-sense polynucleotide molecule can be complementary to the entire coding region of AMM mRNA, but more preferably to only a portion of the coding or noncoding region of AMM mRNA. For example, an anti-sense oligonucleotide can be complementary to the region surrounding the translation start site of AMM mRNA. Anti-sense or sense oligonucleotides may comprise a fragment of the AMM coding region of at least about 14 nucleotides, preferably from about 14 to 30 nucleotides. In general, anti-sense RNA or DNA molecules can comprise at least 5, 10, 15, 20, 25, 30, 35, 40, 45, 50, 55, 60, 65, 70, 75, 80, 85, 90, 95, 100 bases in length or more. Methods to derive anti-sense or sense oligonucleotides have been well-described (Stein and Cohen, 1988; van der Krol et al., 1988a).

Examples of modified nucleotides that can be used to generate the anti-sense polynucleotide include: 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine. Alternatively, the anti-sense polynucleotide can be produced using an expression vector into which a polynucleotide has been sub-cloned in an anti-sense orientation such that the transcribed RNA will be complementary to a target polynucleotide of interest.

To introduce anti-sense or sense oligonucleotides into target cells (cells containing a target polynucleotide sequence), any gene transfer method may be used. Examples of gene transfer methods include (1) biological, such as gene transfer vectors like Epstein-Barr virus or conjugating the exogenous DNA to a ligand-binding molecule, (2) physical, such as electroporation and injection, and (3) chemical, such as $CaPO_4$ precipitation and oligonucleotide-lipid complexes.

An anti-sense or sense oligonucleotide is inserted into a suitable gene transfer retroviral vector. A cell containing the target polynucleotide sequence is contacted with the recombinant retroviral vector, either in vivo or ex vivo. Examples of suitable retroviral vectors include those derived from the murine retrovirus M-MuLV, N2 (a retrovirus derived from M-MuLV), or the double copy vectors designated DCT5A, DCT5B and DCT5C (WO 90/13641, 1990). To achieve sufficient polynucleotide molecule transcription, vector constructs in which the transcription of the anti-sense polynucleotide molecule is controlled by a strong pol II or pol III promoter are preferred. Also preferred are tissue- and cell-specific promoters.

To specify target cells in a mixed population of cells, cell surface receptors that are specific to the target cells can be exploited. Anti-sense and sense oligonucleotides are conjugated to a ligand-binding molecule (WO 91/04753, 1991). Examples of suitable ligand-binding molecules include cell surface receptors, growth factors, cytokines, or other ligands that bind to target cell surface molecules. Preferably, conjugation of the ligand-binding molecule does not substantially interfere with the ability of the receptors or molecule to bind the ligand-binding molecule conjugate, or block entry of the sense or anti-sense oligonucleotide or its conjugated version into the cell.

Liposomes efficiently transfer sense or an anti-sense oligonucleotide to cells (WO 90/10448, 1990). The sense or anti-sense oligonucleotide-lipid complex is preferably dissociated within the cell by an endogenous lipase.

The anti-sense polynucleotide molecule of the invention may be an α-anomeric polynucleotide molecule. An α-anomeric polynucleotide molecule forms specific double-stranded hybrids with complementary RNA in which, contrary to the usual α-units, the strands run parallel to each other (Gautier et al, 1987). The anti-sense polynucleotide molecule can also comprise a 2'-o-methylribonucleotide (Inoue et al., 1987a) or a chimeric RNA-DNA analog (Inoue et al., 1987b).

An anti-sense polynucleotide may be a catalytic RNA molecule with ribonuclease activity, a ribozyme. For example, hammerhead ribozymes (Haseloff and Gerlach, 1988) can be used to catalytically cleave AMM mRNA transcripts and thus inhibit translation. A ribozyme specific for an AMM-encoding polynucleotide can be designed based on the nucleotide sequence of an AMM cDNA (i.e., SEQ ID NO:1). For example, a derivative of a Tetrahymena L-19 IVS RNA can be constructed in which the nucleotide sequence of the active site is complementary to the nucleotide sequence to be cleaved in an AMM-encoding mRNA (Cech et al., U.S. Pat. No. 5,116,742, 1992; Cech et al., U.S. Pat. No. 4,987,071, 1991). AMM mRNA can also be used to select a catalytic RNA having a specific ribonuclease activity from a pool of RNA molecules (Bartel and Szostak, 1993).

Alternatively, AMM expression can be inhibited by targeting nucleotide sequences complementary to the regulatory region of an AMM (e.g., AMM promoter and/or enhancers) to form triple helical structures that prevent transcription of the AMM in target cells (Helene, 1991; Helene et al., 1992; Maher, 1992).

Modifications of anti-sense and sense oligonucleotides can augment their effectiveness. Modified sugar-phosphodiester bonds or other sugar linkages (WO 91/06629, 1991) increase in vivo stability by conferring resistance to endogenous nucleases without disrupting binding specificity to target sequences. Other modifications can increase the affinities of the oligonucleotides for their targets, such as covalently linked organic moieties (WO 90/10448, 1990) or poly-(L)-lysine. Other attachments modify binding specificities of the oligonucleotides for their targets, including metal complexes or intercalating (e.g. ellipticine) and alkylating agents.

For example, the deoxyribose phosphate backbone can be modified to generate peptide polynucleotides (Hyrup and Nielsen, 1996). "Peptide polynucleotides" (PNAs) refer to polynucleotide mimics in which the deoxyribose phosphate backbone is replaced by a pseudopeptide backbone, and only the four natural nucleobases are retained. The neutral backbone of PNAs allows for specific hybridization to DNA and RNA under conditions of low ionic strength. PNA oligomers can be synthesized using solid phase peptide synthesis protocols (Hyrup and Nielsen, 1996; Perry-O'Keefe et al., 1996).

PNAs of AMM can be used in therapeutic and diagnostic applications. For example, PNAs can be used as anti-sense or antigene agents for sequence-specific modulation of gene expression by inducing transcription or translation arrest or inhibiting replication. AMM PNAs may also be used in the analysis of single base pair mutations (e.g., PNA directed PCR clamping; as artificial restriction enzymes when used in combination with other enzymes, e.g., $S_1$ nucleases (Hyrup and Nielsen, 1996); or as probes or primers for DNA sequence and hybridization (Hyrup and Nielsen, 1996; Perry-O'Keefe et al., 1996).

AMM PNAs can be modified to enhance stability or cellular uptake. Lipophilic or other helper groups may be attached to PNAs, PNA-DNA dimers formed, or the use of liposomes or other drug delivery techniques. For example, PNA-DNA chimeras can be generated that combine the advantages of PNA and DNA. Such chimeras allow DNA recognition enzymes (e.g., RNase H and DNA polymerases) to interact with the DNA portion while the PNA portion provides high binding affinity and specificity. PNA-DNA chimeras can be linked using linkers of appropriate lengths selected in terms of base stacking, number of bonds between the nucleobases, and orientation (Hyrup and Nielsen, 1996). The synthesis of PNA-DNA chimeras are described (Finn et al., 1996; Hyrup and Nielsen, 1996). For example, a DNA chain can be synthesized on a solid support using standard phosphoramidite coupling chemistry, and modified nucleoside analogs, e.g., 5'-(4-methoxytrityl)amino-5'-deoxythymidine phosphoramidite, can be used between the PNA and the 5' end of DNA (Finn et al., 1996; Hyrup and Nielsen, 1996). PNA monomers are then coupled in a stepwise manner to produce a chimeric molecule with a 5' PNA segment and a 3' DNA segment (Finn et al., 1996). Alternatively, chimeric molecules can be synthesized with a 5' DNA segment and a 3' PNA segment (Petersen et al., 1976).

The oligonucleotide may include other appended groups such as peptides (e.g., for targeting host cell receptors in vivo), or agents facilitating transport across the cell membrane (Lemaitre et al., 1987; Letsinger et al., 1989) or the blood-brain barrier (Pardridge and Schimmel, WO89/10134, 1989). In addition, oligonucleotides can be modified with hybridization-triggered cleavage agents (van der Krol et al., 1988b) or intercalating agents (Zon, 1988). The oligonucleotide may be conjugated to another molecule, e.g., a peptide, a hybridization triggered cross-linking agent, a transport agent, a hybridization-triggered cleavage agent, and the like.

AMM Polypeptides

The invention pertains to isolated AMMs and biologically-active portions derivatives, fragments, analogs or homologs thereof. Also provided are polypeptide fragments suitable for use as immunogens to raise anti-AMM Abs. AMMs may be isolated from cells and tissues, produced by recombinant DNA techniques or chemically synthesized.

Polypeptides

An AMM polypeptide includes an amino acid sequence of AMM whose sequences are provided in SEq ID NO:2. The invention also includes a mutant or variant polypeptide any of whose residues may be changed from the corresponding residues shown in SEq ID NO:2, while still encoding an active AMM, or a functional fragment.

AMM Polypeptide Variants

In general, an AMM variant that preserves AMM-like function and includes any variant in which residues at a particular position in the sequence have been substituted by other amino acids, and further includes the possibility of inserting an additional residue or residues between two residues of the parent polypeptide as well as the possibility of deleting one or more residues from the parent sequence. Preferably, the substitution is a conservative substitution (Table A).

"AMM polypeptide variant" means an active AMM having at least: (1) about 80% amino acid sequence identity with a full-length native AMM sequence, (2) an AMM sequence lacking a signal peptide, (3) an extracellular domain of an AMM, with or without a signal peptide, or (4) any other fragment of a full-length AMM sequence. For example, AMM variants include those wherein one or more amino acid residues are added or deleted at the N- or C-terminus of the full-length native amino acid sequence. An AMM polypeptide variant will have at least about 80% amino acid sequence identity, preferably at least about 81% amino acid sequence identity, more preferably at least about 82%, 83%, 84%, 85%, 86%, 87%, 88%, 89%, 90%, 91%, 92%, 93%, 94%, 95%, 96%, 97%, 98% amino acid sequence identity and most preferably at least about 99% amino acid sequence identity with a full-length native sequence AMM sequence. Ordinarily, AMM variant polypeptides are at least about 10 amino acids in length, often at least about 20 amino acids in length, more often at least about 30, 40, 50, 60, 70, 80, 90, 100, 150, 200, or 300 amino acids in length, or more.

"Percent (%) amino acid sequence identity" is defined as the percentage of amino acid residues that are identical with amino acid residues in an AMM sequence in a candidate sequence when the two sequences are aligned. To determine % amino acid identity, sequences are aligned and if necessary, gaps are introduced to achieve the maximum % sequence identity; conservative substitutions are not considered as part of the sequence identity. Amino acid sequence alignment procedures to determine percent identity are well known to those of skill in the art. Publicly available computer software such as BLAST, BLAST2, ALIGN2 or Megalign (DNASTAR) can be used to align polypeptide sequences. Those skilled in the art will determine appropriate parameters for measuring alignment, including any algorithms needed to achieve maximal alignment over the full length of the sequences being compared.

When amino acid sequences are aligned, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as:

$$\%\text{amino acid sequence identity} = X/Y \cdot 100$$

where

X is the number of amino acid residues scored as identical matches by the sequence alignment program's or algorithm's alignment of A and B and Y is the total number of amino acid residues in B.

If the length of amino acid sequence A is not equal to the length of amino acid sequence B, the % amino acid sequence identity of A to B will not equal the % amino acid sequence identity of B to A.

Isolated/Purified Polypeptides

An "isolated" or "purified" polypeptide, polypeptide or biologically active fragment is separated and/or recovered from a component of its natural environment. Contaminant components include materials that would typically interfere with diagnostic or therapeutic uses for the polypeptide, and may include enzymes, hormones, and other polypeptideaceous or non-polypeptideaceous materials. Preferably, the polypeptide is purified to a sufficient degree to obtain at least 15 residues of N-terminal or internal amino acid sequence. To be substantially isolated, preparations having less than 30% by dry weight of contaminants, more preferably less than 20%, 10% and most preferably less than 5% contaminants. An isolated, recombinantly-produced AMM or biologically active portion is preferably substantially free of culture medium, i.e., culture medium represents less than 20%, more preferably less than about 10%, and most preferably less than about 5% of the volume of the AMM preparation. Examples of contaminants include cell debris, culture media, and substances used and produced during in vitro synthesis of AMM.

Biologically Active

Biologically active portions of AMM include peptides comprising amino acid sequences sufficiently homologous to, or derived from, the amino acid sequences of an AMM (SEq ID NO:2) that include fewer amino acids than the full-length AMM, and exhibit at least one activity of an AMM. Biologically active portions comprise a domain or motif with at least one activity of native AMM. A biologically active portion of an AMM can be a polypeptide that is 10, 25, 50, 100 or more amino acid residues in length. Other biologically active portions, in which other regions of the polypeptide are deleted, can be prepared by recombinant techniques and evaluated for one or more of the functional activities of a native AMM.

A biologically active portion of an AMM may have an amino acid sequence shown in SEq ID NO:2, or substantially homologous to SEq ID NO:2, and retains the functional activity of the polypeptide of SEq ID NO:2, yet differs in amino acid sequence due to natural allelic variation or mutagenesis. Other biologically active AMMs may comprise an amino acid sequence at least 45% homologous to the amino acid sequence of SEq ID NO:2, and retains the functional activity of native AMM. Homology can be determined as described in AMM polypeptide variants, above.

Chimeric and Fusion Polypeptides

Fusion polypeptides are useful in expression studies, cell-localization, bioassays, and AMM purification. An AMM "chimeric polypeptide" or "fusion polypeptide" comprises a AMM fused to a non-AMM polypeptide. A non-AMM polypeptide is not substantially homologous to AMM (SEq ID NO:2). An AMM fusion polypeptide may include any portion to an entire AMM, including any number of biologically active portions. In some host cells, heterologous signal sequence fusions may ameliorate AMM expression and/or secretion. Exemplary fusions are presented in Table C.

Other fusion partners can adapt AMM therapeutically. Fusions with members of the immunoglobulin (Ig) family are useful to inhibit AMM ligand or substrate interactions, consequently suppressing AMM-mediated signal transduction in vivo. AMM-Ig fusion polypeptides can also be used as immunogens to produce anti-AMM Abs in a subject, to purify AMM ligands, and to screen for molecules that inhibit interactions of AMM with other molecules.

Fusion polypeptides can be easily created using recombinant methods. A polynucleotide encoding AMM can be fused in-frame with a non-AMM encoding polynucleotide, to the AMM $NH_2$— or COO—-terminus, or internally. Fusion genes may also be synthesized by conventional techniques, including automated DNA synthesizers. PCR amplification using anchor primers that give rise to complementary overhangs between two consecutive gene fragments that can subsequently be annealed and reamplified can be used to generate a chimeric gene sequence (Ausubel et al., 1987). Many vectors are commercially available that facilitate sub-cloning AMM in-frame to a fusion moiety.

TABLE C

Useful non-AMM fusion polypeptides and usefulness thereof

| Polypeptide | in vitro | in vivo | Notes | Reference |
| --- | --- | --- | --- | --- |
| Human growth hormone (hGH) | Radioimmunoassay | none | Expensive, insensitive, narrow linear range. | (Selden et al., 1986) |
| β-glucuronidase (GUS) | Colorimetric, fluorescent, or chemiluminescent | colorimetric (histo-chemical staining with X-gluc) | sensitive, broad linear range, non-isotopic. | (Gallagher, 1992) |
| Green fluorescent polypeptide (GFP) and related molecules (RFP, BFP, YFP, etc.) | Fluorescent | fluorescent | can be used in live cells; resists photobleaching | (Chalfie et al., 1994) |
| Luciferase (firefly) | bioluminescent | Bioluminescent | polypeptide is unstable, difficult to reproduce, signal is brief | (de Wet et al., 1987) |
| Chloramphenicol acetyltransferase (CAT) | Chromatography, differential extraction, fluorescent, or immunoassay | none | Expensive radioactive substrates, time-consuming, insensitive, narrow linear range | (Gorman et al., 1982) |
| β-galacto-sidase | colorimetric, fluorescence, chemiluminescence | colorimetric (histochemical staining with X-gal), bioluminescent in live cells | sensitive, broad linear range; some cells have high endogenous activity | (Alam and Cook, 1990) |
| Secrete alkaline phosphatase (SEAP) | colorimetric, bioluminescent, chemiluminescent | none | Chemiluminescence assay is sensitive and broad linear range; some cells have endogenous alkaline | (Berger et al., 1988) |

TABLE C-continued

Useful non-AMM fusion polypeptides and usefulness thereof

| Polypeptide | in vitro | in vivo | Notes | Reference |
|---|---|---|---|---|
| | | | phosphatase activity | |

Therapeutic Applications of AMM

Agonists and Antagonists

"Antagonist" includes any molecule that partially or fully blocks, inhibits, or neutralizes a biological activity of an endogenous AMM. Similarly, "agonist" includes any molecule that mimics a biological activity of an endogenous AMM. Molecules that can act as agonists or antagonists include Abs or Ab fragments, fragments or variants of endogenous AMM, peptides, anti-sense oligonucleotides, small organic molecules, etc.

Identifying Antagonists and Agonists

To assay for antagonists, an AMM is added to, or expressed in, a cell along with the compound to be screened for a particular activity. If the compound inhibits the activity of interest in the presence of the AMM, that compound is an antagonist to the AMM; if AMM activity is enhanced, the compound is an agonist.

AMM-expressing cells are easily identified using standard methods. For example, Abs that recognize the amino- or carboxy-terminus of an AMM can be used to screen candidate cells by immunoprecipitation, Western blots, and immunohistochemical techniques. Likewise, SEQ ID NO:1 can be used to design primers and probes that detect an AMM mRNA in cells or samples from cells.

(a) Examples of Potential Antagonists and Agonist

Examples of antagonists and agonists include: (1) small organic and inorganic compounds, (2) small peptides, (3) Abs and derivatives, (4) polypeptides closely related to AMM, (5) anti-sense DNA and RNA, (6) ribozymes, (7) triple DNA helices and (8) polynucleotide aptamers.

Small molecules that bind to the AMM active site or other relevant part of the polypeptide and inhibit the biological activity of an AMM are antagonists. Examples of small molecule antagonists include small peptides, peptide-like molecules, preferably soluble, and synthetic non-peptidyl organic or inorganic compounds. These same molecules, if they enhance AMM activity, are examples of agonists.

Almost any Ab that affects an AMM function is a candidate antagonist, and occasionally, agonist. Examples of Ab antagonists include polyclonal, monoclonal, single-chain, anti-idiotypic, chimeric Abs, or humanized versions of such Abs or fragments. Abs may be from any species in which an immune response can be raised. Humanized Abs are also contemplated.

Alternatively, a potential antagonist or agonist may be a closely related polypeptide, for example, a mutated form of the AMM that recognizes an AMM-interacting polypeptide but imparts no effect other than competitively inhibiting AMM action. Alternatively, a mutated AMM can be constitutively activated and act as an agonist.

Anti-sense RNA or DNA constructs can be effective antagonists. Anti-sense RNA or DNA molecules block function by inhibiting translation by hybridizing to targeted mRNA. Anti-sense technology can be used to control gene expression through triple-helix formation or anti-sense DNA or RNA, both of which depend on polynucleotide binding to DNA or RNA. For example, the 5' coding portion of an AMM sequence is used to design an anti-sense RNA oligonucleotide of from about 10 to 40 base pairs in length. A DNA oligonucleotide is designed to be complementary to a region of the gene involved in transcription (triple helix) (Beal and Dervan, 1991; Cooney et al., 1988; Lee et al, 1979), thereby preventing transcription and the production of an AMM. The anti-sense RNA oligonucleotide hybridizes to the mRNA in vivo and blocks translation of the mRNA molecule into an AMM (anti-sense) (Cohen, 1989; Okano et al., 1991). These oligonucleotides can also be delivered to cells such that the anti-sense RNA or DNA may be expressed in vivo to inhibit production of an AMM. When anti-sense DNA is used, oligodeoxyribonucleotides derived from the translation-initiation site, e.g., between about −10 and +10 positions of the target gene nucleotide sequence, are preferred.

To inhibit transcription, triple-helix polynucleotides that are single-stranded and comprise deoxynucleotides are useful antagonists. These oligonucleotides are designed such that triple-helix formation via Hoogsteen base-pairing rules is promoted, generally requiring stretches of purines or pyrimidines (WO 97/33551, 1997).

Aptamers are short oligonucleotide sequences that recognize and specifically bind almost any type of molecule. The systematic evolution of ligands by exponential enrichment (SELEX) process (Ausubel et al., 1987; Ellington and Szostak, 1990; Tuerk and Gold, 1990) is a powerful technique to identify aptamers. Aptamers have many diagnostic and clinical uses; almost any use in which an Ab is useful clinically or diagnostically, aptamers too may be used. Aptamers can be easily applied to a variety of formats, including administration in pharmaceutical compositions, in bioassays, and diagnostic tests (Jayasena, 1999).

Anti-AMM Abs

The invention encompasses Abs and Ab fragments, such as $F_{ab}$ or $(F_{ab})_2$, that bind immunospecifically to any epitope of an AMM molecule.

"Antibody" (Ab) comprises single Abs directed against an AMM (an anti-AMM Ab; including agonist, antagonist, and neutralizing Abs), anti-AMM Ab compositions with poly-epitope specificity, single chain anti-AMM Abs, and fragments of anti-AMM Abs. A "monoclonal Ab" is obtained from a population of substantially homogeneous Abs, i.e., the individual Abs comprising the population are identical except for possible naturally-occurring mutations that may be present in minor amounts. Exemplary Abs include polyclonal (pAb), monoclonal (mAb), humanized, bi-specific (bsAb), and heteroconjugate Abs.

Polyclonal Abs (pAbs)

Polyclonal Abs can be raised in a mammalian host by one or more injections of an immunogen and, if desired, an adjuvant. Typically, the immunogen (and adjuvant) is injected in the mammal by multiple subcutaneous or intraperitoneal injections. The immunogen may include an AMM, AMM fragment or an AMM fusion polypeptide. Examples of adjuvants include Freund's complete and monophosphoryl Lipid A synthetic-trehalose dicorynomycolate (MPL-TDM). To improve the immune response, an immunogen may be conjugated to a polypeptide that is immunogenic in the host, such as keyhole limpet hemocyanin (KLH), serum albumin, bovine thyroglobulin, and soybean trypsin inhibitor. Protocols for Ab production are well-known (Ausubel et al., 1987; Harlow and Lane, 1988).

Alternatively, pAbs may be made in chickens, producing IgY molecules (Schade et al., 1996).

Monoclonal Abs (mAbs)

Anti-AMM mAbs may be prepared using hybridoma methods (Milstein and Cuello, 1983). Hybridoma methods comprise at least four steps: (1) immunizing a host, or lymphocytes from a host; (2) harvesting the mAb secreting (or potentially secreting) lymphocytes, (3) fusing the lymphocytes to immortalized cells, and (4) selecting those cells that secrete the desired (anti-AMM) mAb.

A mouse, rat, guinea pig, hamster or other appropriate host is immunized to elicit lymphocytes that produce or are capable of producing Abs that will specifically bind to the immunogen. Alternatively, the lymphocytes may be immunized in vitro. If human cells are desired, peripheral blood lymphocytes (PBLs) are generally used; however, spleen cells or lymphocytes from other mammalian sources are preferred. The immunogen typically includes an AMM (or fragment) or an AMM fusion polypeptide.

The lymphocytes are then fused with an immortalized cell line to form hybridoma cells, facilitated by a fusing agent such as polyethylene glycol (Goding, 1996). Rodent, bovine or human myeloma cells immortalized by transformation may be used, or rat or mouse myeloma cell lines. Because pure populations of hybridoma cells and not unfused immortalized cells are preferred, after fusion, the cells are grown in a suitable medium that inhibits the growth or survival of unfused, immortalized cells. A common technique uses parental cells that lack the enzyme hypoxanthine guanine phosphoribosyl transferase (HGPRT or HPRT). In this case, hypoxanthine, aminopterin and thymidine are added to the medium (HAT medium) to prevent the growth of HGPRT-deficient cells while permitting hybridomas to grow.

Preferred immortalized cells fuse efficiently, can be isolated from mixed populations by selecting in a medium such as HAT, and support stable and high-level expression of Ab after fusion. Preferred immortalized cell lines are murine myeloma lines, available from the American Type Culture Collection (Manassas, Va.). Human myeloma and mouse-human heteromyeloma cell lines also have been described for the production of human mAbs (Kozbor et al., 1984; Schook, 1987).

Because hybridoma cells secrete Ab extracellularly, the culture media can be assayed for the presence of mAbs directed against an AMM (anti-AMM mAbs). Immunoprecipitation or in vitro binding assays, such as radio immunoassay (RIA) or enzyme-linked immunoabsorbent assay (ELISA), measure the binding specificity of mAbs (Harlow and Lane, 1988; Harlow and Lane, 1999), including Scatchard analysis (Munson and Rodbard, 1980).

Anti-AMM mAb secreting hybridoma cells may be isolated as single clones by limiting dilution procedures and sub-cultured (Goding, 1996). Suitable culture media include Dulbecco's Modified Eagle's Medium, RPMI-1640, or if desired, a polypeptide-free or -reduced or serum-free medium (e.g., Ultra DOMA PF or HL-1; Biowhittaker; Walkersville, Md.). The hybridoma cells may also be grown in vivo as ascites.

The mAbs may be isolated or purified from the culture medium or ascites fluid by conventional Ig purification procedures such as polypeptide A-Sepharose, hydroxylapatite chromatography, gel electrophoresis, dialysis, ammonium sulfate precipitation or affinity chromatography (Harlow and Lane, 1988; Harlow and Lane, 1999).

The mAbs may also be made by recombinant methods (U.S. Pat. No. 4,166,452, 1979). DNA encoding anti-AMM mAbs can be readily isolated and sequenced using conventional procedures, e.g., using oligonucleotide probes that specifically bind to murine heavy and light Ab chain genes, to probe preferably DNA isolated from anti-AMM-secreting mAb hybridoma cell lines. Once isolated, the isolated DNA fragments are sub-cloned into expression vectors that are then transfected into host cells such as simian COS-7 cells, Chinese hamster ovary (CHO) cells, or myeloma cells that do not otherwise produce Ig polypeptide, to express mAbs. The isolated DNA fragments can be modified by substituting the coding sequence for human heavy and light chain constant domains in place of the homologous murine sequences (U.S. Pat. No. 4,816,567, 1989; Morrison et al., 1987), or by fusing the Ig coding sequence to all or part of the coding sequence for a non-Ig polypeptide. Such a non-Ig polypeptide can be substituted for the constant domains of an Ab, or can be substituted for the variable domains of one antigen-combining site to create a chimeric bivalent Ab.

Monovalent Abs

The Abs may be monovalent Abs that consequently do not cross-link each other. One method to make such Abs involves recombinant expression of Ig light chain and modified heavy chain. Heavy chain truncations generally at any point in the $F_c$ region will prevent heavy chain cross-linking. Alternatively, relevant cysteine residues are substituted with another amino acid residue or are deleted, preventing crosslinking by disulfide binding. In vitro methods are also suitable for preparing monovalent Abs. Abs can be digested to produce fragments, such as $F_{ab}$ (Harlow and Lane, 1988; Harlow and Lane, 1999).

Humanized and Human Abs

Humanized forms of non-human Abs that bind an AMM are chimeric Igs, Ig chains or fragments (such as $F_v$, $F_{ab}$, $F_{ab'}$, $F_{(ab')2}$ or other antigen-binding subsequences of Abs) that contain minimal sequence derived from non-human Ig.

Generally, a humanized Ab has one or more amino acid residues introduced from a non-human source. These non-human amino acid residues are often referred to as "import" residues, which are typically taken from an "import" variable domain. Humanization is accomplished by substituting rodent complementary determining regions (CDRs) or CDR sequences for the corresponding sequences of a human Ab (Jones et al., 1986; Riechmann et al., 1988; Verhoeyen et al., 1988). Such "humanized" Abs are chimeric Abs (U.S. Pat. No. 4,816,567, 1989), wherein substantially less than an intact human variable domain has been substituted by the corresponding sequence from a non-human species. In practice, humanized Abs are typically human Abs in which some CDR residues and possibly some FR residues are substituted by residues from analogous sites in rodent Abs. Humanized Abs include human Igs (recipient Ab) in which residues from a CDR of the recipient are replaced by residues from a CDR of a non-human species (donor Ab) such as mouse, rat or rabbit, having the desired specificity, affinity and capacity. In some instances, corresponding non-human residues replace $F_v$ framework residues of the human Ig. Humanized Abs may comprise residues that are found neither in the recipient Ab nor in the imported CDR or framework sequences. In general, the humanized Ab comprises substantially all of at least one, and typically two, variable domains, in which most if not all of the CDR regions correspond to those of a non-human Ig and most if not all of the FR regions are those of a human Ig consensus sequence. The humanized Ab optimally also comprises at least a portion of an Ig constant region ($F_c$), typically that of a human Ig (Jones et al., 1986; Presta, 1992; Riechmann et al., 1988).

Human Abs can also be produced using various techniques, including phage display libraries (Hoogenboom et al., 1991; Marks et al., 1991) and human mAbs (Boerner et al., 1991; Reisfeld and Sell, 1985). Introducing human Ig genes into transgenic animals in which the endogenous Ig genes have been partially or completely inactivated can be exploited to synthesize human Abs. Upon challenge, human Ab production is observed, which closely resembles that seen in humans in all respects, including gene rearrangement, assembly, and Ab repertoire (U.S. Pat. No. 5,545,807, 1996; U.S. Pat. No. 5,569,825, 1996; U.S. Pat. No. 5,633,425, 1997; U.S. Pat. No. 5,661,016, 1997; U.S. Pat. No. 5,625,126, 1997; Fishwild et al., 1996; Lonberg and Huszar, 1995; Lonberg et al., 1994; Marks et al., 1992).

Bi-specific mAbs

Bi-specific Abs are monoclonal, preferably human or humanized, that have binding specificities for at least two different antigens. For example, a binding specificity is an AMM; the other is for any antigen of choice, preferably a cell-surface polypeptide or receptor or receptor subunit.

The recombinant production of bi-specific Abs is often achieved by co-expressing two Ig heavy-chain/light-chain pairs, each having different specificities (Milstein and Cuello, 1983). The random assortment of these Ig heavy and light chains in the resulting hybridomas (quadromas) produce a potential mixture of ten different Ab molecules, of which only one has the desired bi-specific structure. The desired Ab can be purified using affinity chromatography or other techniques (WO 93/08829, 1993; Traunecker et al., 1991).

To manufacture a bi-specific Ab (Suresh et al., 1986), variable domains with the desired Ab-antigen combining sites are fused to Ig constant domain sequences. The fusion is preferably with an Ig heavy-chain constant domain, comprising at least part of the hinge, CH2, and CH3 regions. Preferably, the first heavy-chain constant region (CH1) containing the site necessary for light-chain binding is in at least one of the fusions. DNAs encoding the Ig heavy-chain fusions and, if desired, the Ig light chain, are inserted into separate expression vectors and are co-transfected into a suitable host organism.

The interface between a pair of Ab molecules can be engineered to maximize the percentage of heterodimers that are recovered from recombinant cell culture (WO 96/27011, 1996). The preferred interface comprises at least part of the CH3 region of an Ab constant domain. In this method, one or more small amino acid side chains from the interface of the first Ab molecule are replaced with larger side chains (e.g. tyrosine or tryptophan). Compensatory "cavities" of identical or similar size to the large side chain(s) are created on the interface of the second Ab molecule by replacing large amino acid side chains with smaller ones (e.g. alanine or threonine). This mechanism increases the yield of the heterodimer over unwanted end products such as homodimers.

Bi-specific Abs can be prepared as full length Abs or Ab fragments (e.g. $F_{(ab')2}$ bi-specific Abs). One technique to generate bi-specific Abs exploits chemical linkage. Intact Abs can be proteolytically cleaved to generate $F_{(ab')2}$ fragments (Brennan et al., 1985). Fragments are reduced with a dithiol complexing agent, such as sodium arsenite, to stabilize vicinal dithiols and prevent intermolecular disulfide formation. The generated $F_{ab'}$ fragments are then converted to thionitrobenzoate (TNB) derivatives. One of the $F_{ab'}$-TNB derivatives is then reconverted to the $F_{ab'}$-thiol by reduction with mercaptoethylamine and is mixed with an equimolar amount of the other $F_{ab'}$-TNB derivative to form the bi-specific Ab. The produced bi-specific Abs can be used as agents for the selective immobilization of enzymes.

$F_{ab'}$ fragments may be directly recovered from $E.$ $coli$ and chemically coupled to form bi-specific Abs. For example, fully humanized bi-specific $F_{(ab')2}$ Abs can be produced (Shalaby et al., 1992). Each $F_{ab'}$ fragment is separately secreted from $E.$ $coli$ and directly coupled chemically in vitro, forming the bi-specific Ab.

Various techniques for making and isolating bi-specific Ab fragments directly from recombinant cell culture have also been described. For example, leucine zipper motifs can be exploited (Kostelny et al., 1992). Peptides from the Fos and Jun polypeptides are linked to the $F_{ab'}$ portions of two different Abs by gene fusion. The Ab homodimers are reduced at the hinge region to form monomers and then re-oxidized to form Ab heterodimers. This method can also produce Ab homodimers. "Diabody" technology (Holliger et al., 1993) provides an alternative method to generate bi-specific Ab fragments. The fragments comprise a heavy-chain variable domain ($V_H$) connected to a light-chain variable domain ($V_L$) by a linker that is too short to allow pairing between the two domains on the same chain. The $V_H$ and $V_L$ domains of one fragment are forced to pair with the complementary $V_L$ and $V_H$ domains of another fragment, forming two antigen-binding sites. Another strategy for making bi-specific Ab fragments is the use of single-chain $F_v$ ($sF_v$) dimers (Gruber et al., 1994). Abs with more than two valencies may also be made, such as tri-specific Abs (Tutt et al., 1991).

Exemplary bi-specific Abs may bind to two different epitopes on a given AMM. Alternatively, cellular defense mechanisms can be restricted to a particular cell expressing the particular AMM: an anti-AMM arm may be combined with an arm that binds to a leukocyte triggering molecule, such as a T-cell receptor molecule (e.g. CD2, CD3, CD28, or B7), or to $F_c$ receptors for IgG ($F_c\gamma R$), such as $F_c\gamma RI$ (CD64), $F_c\gamma RII$ (CD32) and $F_c\gamma RIII$ (CD16). Bi-specific Abs may also be used to target cytotoxic agents to cells that express a particular AMM. These Abs possess an AMM-binding arm and an arm that binds a cytotoxic agent or a radionuclide chelator.

Heteroconjugate Abs

Heteroconjugate Abs, consisting of two covalently joined Abs, target immune system cells to dispose unwanted cells (U.S. Pat. No. 4,676,980, 1987) and for treatment of human immunodeficiency virus (HIV) infection (WO 91/00360, 1991; WO 92/20373, 1992). Abs prepared in vitro using synthetic polypeptide chemistry methods, including those involving cross-linking agents, are contemplated. For example, immunotoxins may be constructed using a disulfide exchange reaction or by forming a thioether bond. Examples of suitable reagents include iminothiolate and methyl-4-mercaptobutyrimidate (U.S. Pat. No. 4,676,980, 1987).

Immunoconjugates

Immunoconjugates comprise an Ab conjugated to a cytotoxic agent such as a chemotherapeutic agent, toxin (e.g., an enzymatically active toxin or fragment of bacterial, fungal, plant, or animal origin), or a radioactive isotope (i.e., a radioconjugate).

Useful enzymatically-active toxins and fragments include Diphtheria A chain, non-binding active fragments of Diphtheria toxin, exotoxin A chain from $Pseudomonas$ $aeruginosa$, ricin A chain, abrin A chain, modeccin A chain, α-sarcin, $Aleurites$ $fordii$ polypeptides, Dianthin polypeptides, $Phytolaca$ $americana$ polypeptides, $Momordica$ $charantia$ inhibitor, curcin, crotin, $Sapaonaria$ $officinalis$ inhibitor, gelonin, mitogellin, restrictocin, phenomycin, enomycin, and the tricothecenes. A variety of radionuclides are available for the production of radioconjugated Abs, such as $^{212}$Bi, $^{131}$I, $^{131}$In, $^{90}$Y, and $^{186}$Re.

Conjugates of the Ab and cytotoxic agent are made using a variety of bi-functional polypeptide-coupling agents, such as N-succinimidyl-3-(2-pyridyldithiol) propionate (SPDP), iminothiolane (IT), bi-functional derivatives of imidoesters (such as dimethyl adipimidate HCl), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared (Vitetta et al., 1987). $^{14}$C-labeled 1-isothiocyanatobenzyl-3-methyldiethylene triaminepentaacetic acid (MX-DTPA) is an exemplary chelating agent for conjugating radionuclide to Ab (WO 94/11026, 1994).

The Ab may be conjugated to a "receptor" (such as streptavidin) to use in tumor pre-targeting, wherein the Ab-receptor conjugate is administered to the patient, followed by removal of unbound conjugate from the circulation using a clearing agent and then administration of a streptavidin "ligand" (e.g., biotin) that is conjugated to a cytotoxic agent (e.g., a radionuclide).

Effect or Function Engineering

Abs can be modified to enhance their effectiveness in treating a disease, such as obesity, to target and kill adipose cells. For example, cysteine residue(s) may be introduced into the $F_c$ region, thereby allowing interchain disulfide bond formation in this region. Such homodimeric Abs often have improved internalization capability and/or increased complement-mediated cell killing and Ab-dependent cellular cytotoxicity (ADCC) (Caron et al., 1992; Shopes, 1992). Homodimeric Abs with enhanced activity can be prepared using hetero-bifunctional cross-linkers (Wolff et al., 1993). Alternatively, an Ab engineered with dual $F_c$ regions may have enhanced complement lysis (Stevenson et al., 1989).

Immunoliposomes

Liposomes containing the Ab (immunoliposomes) may also be formulated (U.S. Pat. No. 4,485,045, 1984; U.S. Pat. No. 4,544,545, 1985; U.S. Pat. No. 5,013,556, 1991; Eppstein et al., 1985; Hwang et al., 1980). Useful liposomes can be generated by a reverse-phase evaporation method with a lipid composition comprising phosphatidylcholine, cholesterol, and PEG-derivatized phosphatidylethanolamine (PEG-PE). Such preparations are extruded through filters of defined pore size to yield liposomes with a desired diameter. $F_{ab'}$ fragments of the Ab can be conjugated to the liposomes (Martin and Papahadjopoulos, 1982) via a disulfide-interchange reaction. A chemotherapeutic agent, such as Doxorubicin, may also be contained in the liposome (Gabizon et al., 1989). Other useful liposomes with different compositions are contemplated.

Diagnostic Applications of Abs Directed Against AMM

Anti-AMM Abs can be used to localize and/or quantitate AMM (e.g., for use in measuring levels of AMM within tissue samples or for use in diagnostic methods, etc.). Anti-AMM epitope Abs can be utilized as pharmacologically active compounds.

Anti-AMM Abs can be used to isolate a specific AMM by standard techniques, such as immunoaffinity chromatography or immunoprecipitation. These approaches facilitate purifying endogenous AMM antigen-containing polypeptides from cells and tissues. Such approaches can be used to detect AMM in a sample to evaluate the abundance and pattern of expression of the antigenic polypeptide. Anti-AMM Abs can be used to monitor polypeptide levels in tissues as part of a clinical testing procedure; for example, to determine the efficacy of a given treatment regimen. Coupling the Ab to a detectable substance (label) allows detection of Ab-antigen complexes. Classes of labels include fluorescent, luminescent, bioluminescent, and radioactive materials, enzymes and prosthetic groups. Useful labels include horseradish peroxidase, alkaline phosphatase, β-galactosidase, acetylcholinesterase, streptavidin/biotin, avidin/biotin, umbelliferone, fluorescein, fluorescein isothiocyanate, rhodamine, dichlorotriazinylamine fluorescein, dansyl chloride, phycoerythrin, luminol, luciferase, luciferin, aequorin, and $^{125}I$, $^{131}I$, $^{35}S$ or $^3H$.

Ab Therapeutics

Abs can be used therapeutically to treat or prevent a disease or pathology in a subject. An Ab preparation, preferably one having high antigen specificity and affinity, generally mediates an effect by binding the target epitope(s). Administration of such Abs may mediate one of two effects: (1) the Ab may prevent ligand binding, eliminating endogenous ligand binding and subsequent signal transduction, or (2) the Ab elicits a physiological response by binding an effector site on the target molecule, initiating signaling.

A therapeutically effective amount of an Ab relates generally to the amount needed to achieve a therapeutic objective, epitope binding affinity, administration rate, and depletion rate of the Ab from a subject. Common ranges for therapeutically effective doses are about 0.1 mg/kg body weight to about 50 mg/kg body weight. Dosing frequencies may range, for example, from twice daily to once a week.

Pharmaceutical Compositions of Abs

Anti-AMM Abs, as well as other AMM interacting molecules (such as aptamers) identified in other assays, can be administered in pharmaceutical compositions to treat various disorders. Principles and considerations involved in preparing such compositions, as well as guidance in the choice of components are well described (de Boer, 1994; Gennaro, 2000; Lee, 1990).

Abs that are internalized are preferred when whole Abs are used as inhibitors and the target is intracellular. Liposomes can be used to deliver intracellularly. Where Ab fragments are used, the smallest inhibitory fragment that specifically binds to the epitope is preferred. For example, peptide molecules can be designed that bind a preferred epitope based on the variable-region sequences of a useful Ab. Such peptides can be synthesized chemically and/or produced by recombinant DNA technology (Marasco et al., 1993). Formulations may also contain more than one active compound for a particular treatment, preferably those with activities that do not adversely affect each other. The composition may comprise an agent that enhances function, such as a cytotoxic agent, cytokine, chemotherapeutic agent, or growth-inhibitory agent.

The active ingredients can also be entrapped in microcapsules prepared by coacervation techniques or by interfacial polymerization; for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration are highly preferred to be sterile. This is readily accomplished by filtration through sterile filtration membranes or any of a number of techniques.

Sustained-release preparations may also be prepared, such as semi-permeable matrices of solid hydrophobic polymers containing the Ab, which matrices are in the form of shaped articles, e.g., films, or microcapsules. Examples of sustained-release matrices include polyesters, hydrogels (for example, poly(2-hydroxyethyl-methacrylate), or poly (vinylalcohol)), polylactides (Boswell and Scribner, U.S. Pat. No. 3,773,919, 1973), copolymers of L-glutamic acid and γ ethyl-L-glutamate, non-degradable ethylene-vinyl acetate, degradable lactic acid-glycolic acid copolymers such as injectable microspheres composed of lactic acid-glycolic acid copolymer, and poly-D-(-)-3-hydroxybutyric acid. While polymers such as ethylene-vinyl acetate and lactic acid-glycolic acid enable release of molecules for over 100 days, certain hydrogels release polypeptides for shorter time periods and may be preferred.

AMM Recombinant Expression Vectors and Host Cells

Vectors are tools used to shuttle DNA between host cells or as a means to express a nucleotide sequence. Some vectors function only in prokaryotes, while others function in both prokaryotes and eukaryotes, enabling large-scale DNA preparation from prokaryotes for expression in eukaryotes. Inserting the DNA of interest, such as an AMM nucleotide sequence or a fragment, is accomplished by ligation techniques and/or mating protocols well known to the skilled artisan. Such DNA is inserted such that its integration does not disrupt any necessary components of the vector. In the case of vectors that are used to express the inserted DNA polypeptide, the introduced DNA is operably-linked to the vector elements that govern its transcription and translation.

Vectors can be divided into two general classes: Cloning vectors are replicating plasmid or phage with regions that are non-essential for propagation in an appropriate host cell, and into which foreign DNA can be inserted; the foreign DNA is replicated and propagated as if it were a component of the vector. An expression vector (such as a plasmid, yeast, or animal virus genome) is used to introduce foreign genetic material into a host cell or tissue in order to transcribe and translate the foreign DNA. In expression vectors, the introduced DNA is operably-linked to elements, such as promoters, that signal to the host cell to transcribe the inserted DNA. Some promoters are exceptionally useful, such as inducible promoters that control gene transcription in response to specific factors. Operably-linking an AMM or anti-sense construct to an inducible promoter can control the expression of an AMM or fragments, or anti-sense constructs. Examples of classic inducible promoters include those responsive to α-interferon, heat-shock, heavy metal ions, and steroids such as glucocorticoids (Kaufman, 1990) and tetracycline. Other desirable inducible promoters include those that are not endogenous to the cells in which the construct is being introduced, but, however, is responsive in those cells when the induction agent is exogenously supplied.

Vectors have many manifestations. A "plasmid" is a circular double stranded DNA molecule that can accept additional DNA fragments. Viral vectors can also accept additional DNA segments into the viral genome. Certain vectors are capable of autonomous replication in a host cell (e.g., bacterial vectors having a bacterial origin of replication and episomal mammalian vectors). Other vectors (e.g., non-episomal mammalian vectors) integrate into the genome of a host cell and replicate as part of the host genome. In general, useful expression vectors are plasmids and viral vectors (e.g., replication defective retroviruses, adenoviruses and adeno-associated viruses); other expression vectors can also be used.

Recombinant expression vectors that comprise an AMM (or fragment(s)) regulate an AMM transcription by exploiting one or more host cell-responsive (or that can be manipulated in vitro) regulatory sequences that is operably-linked to AMM. "Operably-linked" indicates that a nucleotide sequence of interest is linked to regulatory sequences such that expression of the nucleotide sequence is achieved.

Vectors can be introduced in a variety of organisms and/or cells (Table D). Alternatively, the vectors can be transcribed and translated in vitro, for example using T7 promoter regulatory sequences and T7 polymerase.

TABLE D

Examples of hosts for cloning or expression

| Organisms | Examples | Sources and References* |
|---|---|---|
| Prokaryotes | | |
| Enterobacteriaceae | E. coli | |
| | K 12 strain MM294 | ATCC 31,446 |
| | X1776 | ATCC 31,537 |
| | W3110 | ATCC 27,325 |
| | K5 772 | ATCC 53,635 |
| | Enterobacter | |
| | Erwinia | |

TABLE D-continued

Examples of hosts for cloning or expression

| Organisms | Examples | Sources and References* |
|---|---|---|
| | Klebsiella | |
| | Proteus | |
| | Salmonella | |
| | (S. tyhpimurium) | |
| | Serratia (S. marcescans) | |
| | Shigella | |
| | Bacilli (B. subtilis and B. licheniformis) | |
| | Pseudomonas | |
| | (P. aeruginosa) | |
| | Streptomyces | |
| Eukaryotes | | |
| Yeasts | Saccharomyces cerevisiae | |
| | Schizosaccharomyces pombe | |
| | Kluyveromyces | (Fleer et al., 1991) |
| | K. lactis MW98-8C, CBS683, CBS4574 | (de Louvencourt et al., 1983) |
| | K. fragilis | ATCC 12,424 |
| | K. bulgaricus | ATCC 16,045 |
| | K. wickeramii | ATCC 24,178 |
| | K. waltii | ATCC 56,500 |
| | K. drosophilarum | ATCC 36,906 |
| | K. thermotolerans | |
| | K. marxianus; yarrowia | (EPO 402226, 1990) |
| | Pichia pastoris | (Sreekrishna et al., 1988) |
| | Candida | |
| | Trichoderma reesia | |
| | Neurospora crassa | (Case et al., 1979) |
| | Torulopsis | |
| | Rhodotorula | |
| | Schwanniomyces (S. occidentalis) | |
| Filamentous Fungi | Neurospora | |
| | Penicillium | |
| | Tolypocladium | (WO 91/00357, 1991) |
| | Aspergillus (A. nidulans and A.niger) | (Kelly and Hynes, 1985; Tilburn et al., 1983; Yelton et al., 1984) |
| Invertebrate cells | Drosophila S2 | |
| | Spodoptera Sf9 | |
| Vertebrate cells | Chinese Hamster Ovary (CHO) | |
| | simian COS COS-7 HEK 293 | ATCC CRL 1651 |

*Unreferenced cells are generally available from American Type Culture Collection (Manassas, VA).

Vector choice is dictated by the organism or cells being used, and the desired fate of the vector. Vectors may replicate once in the target cells, or may be "suicide" vectors. In general, vectors comprise signal sequences, origins of replication, marker genes, enhancer elements, promoters, and transcription termination sequences. The choice of these elements depends on the organisms in which the vector will be used. Some of these elements may be conditional, such as an inducible or conditional promoter that is turned "on" when conditions are appropriate. Examples of inducible promoters include those that are tissue-specific, which relegate expression to certain cell types, steroid-responsive, or heat-shock reactive. Some bacterial repression systems, such as the lac operon, have been exploited in mammalian cells and transgenic animals (Fieck et al., 1992; Wyborski et al., 1996; Wyborski and Short, 1991). Vectors often use a selectable marker to facilitate identifying those cells that have incorporated the vector. Many selectable markers are well known in the art for the use with prokaryotes, usually antibiotic-resistance genes or the use of autotrophy and auxotrophy mutants. Table F summarizes many of the available markers.

"Host cell" and "recombinant host cell" are used interchangeably. Such terms refer not only to a particular subject cell but also to the progeny or potential progeny of such a cell. Because certain modifications may occur in succeeding generations due to either mutation or environmental influences, such progeny may not, in fact, be identical to the parent cell, but are still included within the scope of the term.

Methods of eukaryotic cell transfection and prokaryotic cell transformation are well known (see Table E for examples). The choice of host cell dictates the preferred technique for introducing the polynucleotide of interest. Introduction of polynucleotides into an organism may also be done with ex vivo techniques that use an in vitro method of transfection, as well as established genetic techniques for that particular organism.

TABLE E

Methods to introduce polynucleotide into cells

| Cells | Methods | References | Notes |
|---|---|---|---|
| Prokaryotes (bacteria) | Calcium chloride | (Cohen et al., 1972; Hanahan, 1983; Mandel and Higa, 1970) | |
| | Electroporation | (Shigekawa and Dower, 1988) | |
| Eukaryotes Mammalian cells | Calcium phosphate transfection | N-(2-Hydroxyethyl)piperazine-N'-(2-ethanesulfonic acid (HEPES) buffered saline solution (Chen and Okayama, 1988; Graham and van der Eb, 1973; Wigler et al., 1978) BES (N,N-bis(2-hydroxyethyl)-2-aminoethanesulfonic acid) buffered solution (Ishiura et al., 1982) | Cells may be "shocked" with glycerol or dimethylsulfoxide (DMSO) to increase transfection efficiency (Ausubel et al., 1987). |
| | Diethylaminoethyl (DEAE)-Dextran transfection | (Fujita et al., 1986; Lopata et al., 1984; Selden et al., 1986) | Most useful for transient, but not stable, transfections. Chloroquine can be used to increase efficiency. |
| | Electroporation | (Neumann et al., 1982; Potter, 1988; Potter et al., 1984; Wong and Neumann, 1982) | Especially useful for hard-to-transfect lymphocytes. |
| | Cationic lipid reagent transfection | (Elroy-Stein and Moss, 1990; Felgner et al., 1987; Rose et al., 1991; Whitt et al., 1990) | Applicable to both in vivo and in vitro transfection. |
| | Retroviral | Production exemplified by (Cepko et al., 1984; Miller and Buttimore, 1986; Pear et al., 1993) Infection in vitro and in vivo: (Austin and Cepko, 1990; Bodine et al., 1991; Fekete and Cepko, 1993; Lemischka et al., 1986; Turner et al., 1990; Williams et al., 1984) | Lengthy process, many packaging lines available at ATCC. Applicable to both in vivo and in vitro transfection. |
| | Polybrene | (Chaney et al., 1986; Kawai and Nishizawa, 1984) | |
| | Microinjection | (Capecchi, 1980) | Can be used to establish cell lines carrying integrated copies of AMM DNA sequences. |
| | Protoplast fusion | (Rassoulzadegan et al., 1982; Sandri-Goldin et al., 1981; Schaffner, 1980) | |
| Insect cells (in vitro) | Baculovirus systems | (Luckow, 1991; Miller, 1988; O'Reilly et al., 1992) | Useful for in vitro production of polypeptides with eukaryotic modifications. |
| Yeast | Electroporation | (Becker and Guarente, 1991) | |
| | Lithium acetate | (Gietz et al., 1998; Ito et al., 1983) | |
| | Spheroplast fusion | (Beggs, 1978; Hinnen et al., 1978) | Laborious, can produce aneuploids. |
| Plant cells (general reference: (Hansen and Wright, 1999)) | Agrobacterium transformation | (Bechtold and Pelletier, 1998; Escudero and Hohn, 1997; Hansen and Chilton, 1999; Touraev and al., 1997) | |
| | Biolistics (microprojectiles) | (Finer et al., 1999; Hansen and Chilton, 1999; Shillito, 1999) | |
| | Electroporation (protoplasts) | (Fromm et al., 1985; Ou-Lee et al., 1986; Rhodes et al., 1988; Saunders et al., 1989) May be combined with liposomes (Trick and al., 1997) | |
| | Polyethylene glycol (PEG) treatment | (Shillito, 1999) | |
| | Liposomes | May be combined with electroporation (Trick and al., 1997) | |
| | in planta microinjection | (Leduc and al., 1996; Zhou and al., 1983) | |
| | Seed imbibition | (Trick and al., 1997) | |
| | Laser beam | (Hoffman, 1996) | |
| | Silicon carbide whiskers | (Thompson and al., 1995) | |

TABLE F

Useful selectable markers for eukaryote cell transfection

| Selectable Marker | Selection | Action | Reference |
|---|---|---|---|
| Adenosine deaminase (ADA) | Media includes 9-β-D-xylofuranosyl adenine (Xyl-A) | Conversion of Xyl-A to Xyl-ATP, which incorporates into polynucleotides, killing cells. ADA detoxifies | (Kaufman et al., 1986) |
| Dihydrofolate reductase (DHFR) | Methotrexate (MTX) and dialyzed serum (purine-free media) | MTX competitive inhibitor of DHFR. In absence of exogenous purines, cells require DHFR, a necessary enzyme in purine biosynthesis. | (Simonsen and Levinson, 1983) |
| Aminoglycoside phosphotransferase ("APH", "neo", "G418") | G418 | G418, an aminoglycoside detoxified by APH, interferes with ribosomal function and consequently, translation. | (Southern and Berg, 1982) |
| Hygromycin-B-phosphotransferase (HPH) | hygromycin-B | Hygromycin-B, an aminocyclitol detoxified by HPH, disrupts polypeptide translocation and promotes mistranslation. | (Palmer et al., 1987) |
| Thymidine kinase (TK) | Forward selection (TK+): Media (HAT) incorporates aminopterin. Reverse selection (TK−): Media incorporates 5-bromodeoxyuridine (BrdU). | Forward: Aminopterin forces cells to synthesize dTTP from thymidine, a pathway requiring TK. Reverse: TK phosphorylates BrdU, which incorporates into polynucleotides, killing cells. | (Littlefield, 1964) |

A host cell, prokaryotic or eukaryotic, can be used to produce an AMM in culture. To accomplish in vitro expression of an AMM, a host cell containing a recombinant expression vector encoding an AMM is expressed, when cultured in a suitable medium. The AMM may then be isolated from the media or culture.

Transgenic AMM Animals

Transgenic animals are useful for studying the function and/or activity of an AMM and for identifying and/or evaluating modulators of an AMM activity. "Transgenic animals" are non-human animals, preferably mammals, more preferably rodents such as rats or mice, in which one or more of the cells include a transgene. Other transgenic animals include primates, sheep, dogs, cows, goats, chickens, amphibians, etc. A "transgene" is exogenous DNA that is integrated into the genome of a cell from which a transgenic animal develops and that remains in the genome of the mature animal. Transgenes preferably direct the expression of an encoded gene product in one or more cell types or tissues, preventing expression of a naturally encoded gene product in one or more cell types or tissues (a "knockout" transgenic animal), over-expressing an encoded gene, or serving as a marker or indicator of an integration, chromosomal location, or region of recombination (e.g. cre/loxP mice). A "homologous recombinant animal" is a non-human animal, such as a rodent, in which an endogenous AMM has been altered by an exogenous DNA molecule that recombines homologously with an endogenous AMM in a (e.g. embryonic) cell prior to development the animal. Host cells with an exogenous AMM can be used to produce non-human transgenic animals, such as fertilized oocytes or embryonic stem cells into which an AMM coding sequence has been introduced. Such host cells can then be used to create non-human transgenic animals or homologous recombinant animals.

Approaches to Transgenic Animal Production

A transgenic animal can be created by introducing an AMM into the male pronuclei of a fertilized oocyte (e.g., by microinjection, retroviral infection, etc.) and allowing the oocyte to develop in a pseudopregnant female foster animal (pffa). The AMM sequences (SEQ ID NO:1) can be introduced as a transgene into the genome of a non-human animal. Alternatively, a homologue of an AMM can be used as a transgene. Intronic sequences and polyadenylation signals can also be included in the transgene to increase transgene expression. Tissue-specific regulatory sequences can be operably-linked to the AMM transgene to direct expression of AMM to particular cells. Methods for generating transgenic animals via embryo manipulation and microinjection, particularly animals such as mice, have become conventional in the art (Evans et al., U.S. Pat. No. 4,870,009, 1989; Hogan, 0879693843, 1994; Leder and Stewart, U.S. Pat. No. 4,736,866, 1988; Wagner and Hoppe, U.S. Pat. No. 4,873,191, 1989). Other non-mice transgenic animals may be made by similar methods. A transgenic founder animal, which can be used to breed additional transgenic animals, can be identified based upon the presence of the transgene in its genome and/or expression of the transgene mRNA in tissues or cells of the animals. Transgenic (e.g. AMM) animals can be bred to other transgenic animals carrying other transgenes.

Vectors for Transgenic Animal Production

To create a homologous recombinant animal, a vector containing at least a portion of an AMM in which a deletion, addition or substitution has been introduced to thereby alter, e.g., functionally disrupt, the AMM can be used. The AMM can be a mouse gene (SEQ ID NO:1) or an AMM homologue. In one approach, a knockout vector functionally disrupts an endogenous AMM gene upon homologous recombination, and thus a non-functional AMM polypeptide, if any, is expressed.

Alternatively, the vector can be designed such that upon homologous recombination, an endogenous AMM is mutated or otherwise altered but still encodes functional polypeptide (e.g., the upstream regulatory region can be altered to thereby alter the expression of an endogenous AMM). In this type of homologous recombination vector, the altered portion of an AMM is flanked at its 5'- and 3'-termini by additional polynucleotide of an AMM to allow for homologous recombination to occur between the exogenous AMM carried by the vector and an endogenous AMM in an embryonic stem cell. The additional flanking AMM polynucleotide is sufficient to engender homologous recombination with the target endogenous AMM. Typically, several kilobases of flanking DNA (both at the 5'- and 3'-termini) are included in the vector (Thomas and Capecchi, 1987). The vector is then introduced into an embryonic stem cell line, and cells in which the introduced AMM has homologously-recombined with an endogenous AMM are selected (Li et al., 1992).

Introduction of AMM Transgene Cells During Development

Selected cells are then injected into a blastocyst of an animal to form aggregation chimeras (Bradley, 1987). A chimeric embryo can then be implanted into a suitable pffa and the embryo brought to term. Progeny harboring the homologously-recombined DNA in their germ cells can be used to breed animals in which all cells of the animal contain the homologously-recombined DNA by germline transmission of the transgene. Methods for constructing homologous recombination vectors and homologous recombinant animals are well-described (Berns et al., WO 93/04169, 1993; Bradley, 1991; Kucherlapati et al., WO 91/01140, 1991; Le Mouellic and Brullet, WO 90/11354, 1990).

Alternatively, transgenic animals that contain selected systems that allow for regulated expression of the transgene can be produced. For example, the cre/loxP recombinase system of bacteriophage P1 (Lakso et al., 1992) or the FLP recombinase system of *Saccharomyces cerevisiae* (O'Gorman et al., 1991) may be used. In cre/loxP recombinase systems, animals containing transgenes encoding both the Cre recombinase and a selected polypeptide are required. Such animals can be produced as "double" transgenic animals, by mating an animal containing a transgene encoding a selected polypeptide to another containing a transgene encoding a recombinase.

Clones of transgenic animals can also be produced (Wilmut et al., 1997). In brief, a cell from a transgenic animal can be isolated and induced to exit the growth cycle and enter $G_0$ phase. The quiescent cell can then be fused to an enucleated oocyte from an animal of the same species from which the quiescent cell is isolated. The reconstructed oocyte is then cultured to develop to a morula or blastocyte and then transferred to a pffa. The offspring borne of this female foster animal will be a clone of the "parent" transgenic animal.

Pharmaceutical Compositions

The AMM polynucleotide molecules, AMM polypeptides, and anti-AMM Abs, and their derivatives, fragments, analogs and homologs, can be incorporated into pharmaceutical compositions. Such compositions typically comprise a polynucleotide molecule, polypeptide, or Ab and a pharmaceutically acceptable carrier. A "pharmaceutically acceptable carrier" includes any and all solvents, dispersion media, coatings, antibacterial and antifungal agents, isotonic and absorption delaying agents, etc., compatible with pharmaceutical administration (Gennaro, 2000). Preferred examples of such carriers or diluents include, but are not limited to, water, saline, finger's solutions, dextrose solution, and 5% human serum albumin. Liposomes and non-aqueous vehicles such as fixed oils may also be used. Except when a conventional media or agent is incompatible with an active compound, use of these compositions is contemplated. Supplementary active compounds can also be incorporated into the compositions.

General Considerations

A pharmaceutical composition is formulated to be compatible with the intended route of administration, including intravenous, intradermal, subcutaneous, oral (e.g., inhalation), transdermal (i.e., topical), transmucosal, and rectal administration. Solutions or suspensions used for parenteral, intradermal, or subcutaneous application can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampules, disposable syringes or multiple dose vials made of glass or plastic.

Injectable Formulations

To access adipose tissue, injection provides a direct and facile route, especially for that tissue that is below the skin. Pharmaceutical compositions suitable for injection include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid so as to be administered using a syringe. Such compositions should be stable during manufacture and storage and must be preserved against contamination from microorganisms such as bacteria and fungi. The carrier can be a solvent or dispersion medium containing, for example, water, ethanol, polyol (such as glycerol, propylene glycol, and liquid polyethylene glycol), and suitable mixtures. Proper fluidity can be maintained, for example, by using a coating such as lecithin, by maintaining the required particle size in the case of dispersion and by using surfactants. Various antibacterial and antifungal agents, such as parabens, chlorobutanol, phenol, ascorbic acid, and thimerosal, can control microorganism contamination. Isotonic agents, such as sugars, polyalcohols such as manitol, sorbitol, and sodium chloride can be included in the composition. Compositions that delay absorption include agents such as aluminum monostearate and gelatin.

Sterile injectable solutions can be prepared by incorporating the active compound (e.g., an AMM or anti-AMM Ab) in an appropriate solvent with one or a combination of ingredients, followed by sterilization. Generally, dispersions are prepared by incorporating the active compound into a sterile vehicle that contains a basic dispersion medium, and any other required ingredients. Sterile powders for the preparation of sterile injectable solutions methods of preparation include vacuum drying and freeze-drying that yield a powder containing the active ingredient and any desired ingredient from a sterile solutions.

Oral Compositions

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally. Pharmaceutically compatible binding agents, and/or adjuvant materials can be included. Tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL, or corn starch; a lubricant such as magnesium stearate or STEROTES; a glidant such as colloidal silicon dioxide; a sweetening agent such as sucrose or saccharin; or a flavoring agent such as peppermint, methyl salicylate, or orange flavoring.

Compositions for Inhalation

For administration by inhalation, the compounds are delivered as an aerosol spray from a nebulizer or a pressurized container that contains a suitable propellant, e.g., a gas such as carbon dioxide.

Systemic Administration

Systemic administration can also be transmucosal or transdermal. For transmucosal or transdermal administration, penetrants that can permeate the target barrier(s) are selected. Transmucosal penetrants include, detergents, bile salts, and fusidic acid derivatives. Nasal sprays or suppositories can be used for transmucosal administration. For transdermal administration, the active compounds are formulated into ointments, salves, gels, or creams.

The compounds can also be prepared in the form of suppositories (e.g., with bases such as cocoa butter and other glycerides) or retention enemas for rectal delivery.

Carriers

In one embodiment, the active compounds are prepared with carriers that protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid (ALZA Corporation; Mountain View, Calif. and NOVA Pharmaceuticals, Inc.; Lake Elsinore, Calif.). Liposomal suspensions can also be used as pharmaceutically acceptable carriers (Eppstein et al., U.S. Pat. No. 4,522,811, 1985).

Unit Dosage

Oral formulations or parenteral compositions in unit dosage form can be created to facilitate administration and dosage uniformity. Unit dosage form refers to physically discrete units suited as single doses for a subject to be treated, containing a therapeutically effective quantity of active compound in association with the required pharmaceutical carrier. The specification for unit dosage forms are dictated by, and directly dependent on, the unique characteristics of the active compound and the particular desired therapeutic effect, and the inherent limitations of compounding the active compound.

Gene Therapy Compositions

The polynucleotide molecules of the invention can be inserted into vectors and used as gene therapy vectors. Gene therapy vectors can be delivered to a subject by, for example, intravenous injection, local administration (Nabel and Nabel, U.S. Pat. No. 5,328,470, 1994), or by stereotactic injection (Chen et al., 1994). The pharmaceutical preparation of a gene therapy vector can include an acceptable diluent, or can comprise a slow release matrix in which the gene delivery vehicle is embedded. Alternatively, where the complete gene delivery vector can be produced intact from recombinant cells, e.g., retroviral vectors, the pharmaceutical preparation can include one or more cells that produce the gene delivery system.

Dosage

The pharmaceutical compositions and methods of the present invention may further comprise other therapeutically active compounds that are usually applied in the treatment of adipose-related pathologies.

In the treatment or prevention of conditions which require modulation of an AMM, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to a patient to be treated. The compounds may be administered on a regimen of 1 to 4 times per day, preferably once or twice per day.

It will be understood, however, that the specific dose level and frequency of dosage for any particular patient may be varied and depends upon a variety of factors, including the activity of the specific compound employed, the metabolic stability and length of action of that compound, the age, body weight, general health, sex, diet, mode and time of administration, rate of excretion, drug combination, the severity of the particular condition, and the host undergoing therapy.

Kits for Pharmaceutical Compositions

The pharmaceutical compositions can be included in a kit, container, pack, or dispenser together with instructions for administration. When the invention is supplied as a kit, the different components of the composition may be packaged in separate containers and admixed immediately before use. Such packaging of the components separately may permit long-term storage without losing the activity of the components.

Kits may also include reagents in separate containers that facilitate the execution of a specific test, such as diagnostic tests or tissue-typing. For example, AMM DNA templates and suitable primers may be supplied for internal controls.

(a) Containers or Vessels

The reagents included in the kits can be supplied in containers of any sort such that the life of the different components are preserved and are not adsorbed or altered by the materials of the container. For example, sealed glass ampules may contain lyophilized luciferase or buffer that have been packaged under a neutral non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include bottles that may be fabricated from similar substances as ampules, and envelopes, that may consist of foil-lined interiors, such as aluminum or an alloy. Other containers include test tubes, vials, flasks, bottles, syringes, etc. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, etc.

(b) Instructional Materials

Kits may also be supplied with instructional materials. Instructions may be printed on paper or other substrate, and/or may be supplied as an electronic-readable medium, such as a floppy disc, CD-ROM, DVD-ROM, Zip disc, videotape, audio tape, etc. Detailed instructions may not be physically associated with the kit; instead, a user may be directed to an internet web site specified by the manufacturer or distributor of the kit, or supplied as electronic mail.

Screening and Detection Methods

The isolated polynucleotides of the invention can be used to express an AMM (e.g., via a recombinant expression vector in a host cell in gene therapy applications), to detect an AMM mRNA (e.g., in a biological sample) or a genetic lesion in an AMM, and to modulate an AMM activity. In addition, AMM polypeptides can be used to screen drugs or compounds that modulate an AMM activity or expression, as well as to treat disorders characterized by insufficient or excessive production of an AMM or production of forms of an AMM that have decreased or aberrant activity compared to AMM wild-type polypeptide, or modulate biological function that involve AMM. In addition, the anti-AMM Abs of the invention can be used to detect and isolate an AMM and modulate an AMM activity.

Screening Assays

The invention provides a method (screening assay) for identifying modalities, i.e., candidate or test compounds or agents (e.g., peptides, peptidomimetics, small molecules or other drugs), foods, combinations thereof, etc., that effect an AMM as a stimulatory or inhibitory effect, including translation, transcription, activity or copies of the gene in cells. The invention also includes compounds identified in screening assays.

Testing for compounds that increase or decrease AMM activity are desirable. A compound may modulate AMM activity by affecting: (1) the number of copies of the gene in the cell (amplifiers and deamplifiers); (2) increasing or decreasing transcription of the AMM (transcription up-regulators and down-regulators); (3) by increasing or decreasing the translation of AMM mRNA into polypeptide (translation up-regulators and down-regulators); or (4) by increasing or decreasing the activity of AMM itself (agonists and antagonists).

(a) Effects of Compounds

To identify compounds that affect an AMM at the DNA, RNA and polypeptide levels, cells or organisms are contacted with a candidate compound, and the corresponding change in the target AMM DNA, RNA or polypeptide is assessed (Ausubel et al., 1987). For DNA amplifiers and deamplifiers, the amount of an AMM DNA is measured; for those compounds that are transcription up-regulators and down-regulators, the amount of AMM mRNA is determined; for translational up- and down-regulators, the amount of AMM polypeptides is measured. Compounds that are agonists or antagonists may be identified by contacting cells or organisms with the compound.

Many assays for screening candidate or test compounds that bind to or modulate the activity of an AMM or AMM polypeptide or biologically active portion are available. Test compounds can be obtained using any of the numerous approaches in combinatorial library methods, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptides, while the other four approaches encompass peptide, non-peptide oligomer or small molecule libraries of compounds (Lam, 1997).

(b) Small Molecules

A "small molecule" refers to a composition that has a molecular weight of less than about 5 kD and more preferably less than about 4 kD, and most preferably less than 0.6 kD. Small molecules can be polynucleotides, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention. Examples of methods for the synthesis of molecular libraries are described (Carell et al., 1994a; Carell et al., 1994b; Cho et al., 1993; DeWitt et al., 1993; Gallop et al., 1994; Zuckermann et al., 1994).

Libraries of compounds may be presented in solution (Houghten et al., 1992) or on beads (Lam et al., 1991), on chips (Fodor et al., 1993), bacteria, spores (Ladner et al., U.S. Pat. No. 5,223,409, 1993), plasmids (Cull et al., 1992) or phage (Cwirla et al., 1990; Devlin et al., 1990; Felici et al., 1991; Ladner et al., U.S. Pat. No. 5,223,409, 1993; Scott and Smith, 1990). A cell-free assay comprises contacting an AMM or biologically-active fragment with a known compound that binds an AMM to form an assay mixture, contacting the assay mixture with a test compound, and determining the ability of the test compound to interact with the target AMM, where determining the ability of the test compound to interact with the target AMM comprises determining the ability of the target AMM to preferentially bind to or modulate the activity of an AMM target molecule.

(c) Cell-free Assays

The cell-free assays of the invention may be used with both soluble or a membrane-bound forms of the various AMMs. In the case of cell-free assays comprising membrane-bound forms, a solubilizing agent can be used to maintain AMM in solution. Examples of such solubilizing agents include non-ionic detergents such as n-octylglucoside, n-dodecylglucoside, n-dodecylmaltoside, octanoyl-N-methylglucamide, decanoyl-N-methylglucamide, t-Octylphenoxypolyethoxyethanol and other polyoxyethylene ethers, polyoxyehtylene 9 lauryl ether, isotridecypoly(ethylene glycol ether)$_n$, N-dodecyl-N, N-dimethyl-3-ammonio-1-propane sulfonate, 3-(3-cholamidopropyl)dimethylamminiol-1-propane sulfonate (CHAPS), or 3-(3-cholamidopropyl)dimethylamminiol-2-hydroxy-1-propane sulfonate (CHAPSO).

(d) Immobilization of Target Molecules to Facilitate Screening

In more than one embodiment of the assay methods, immobilizing either an AMM or one of its partner molecules can facilitate separation of complexed from uncomplexed forms of one or both of the polypeptides, as well as to accommodate high throughput assays. Binding of a test compound to an AMM, or interaction of an AMM with a target molecule in the presence and absence of a candidate compound, can be accomplished in any vessel suitable for containing the reactants, such as microtiter plates, test tubes, and micro-centrifuge tubes. A fusion polypeptide can be provided that adds a domain that allows one or both of the polypeptides to be bound to a matrix. For example, GST-AMM fusion polypeptides or GST-target fusion polypeptides can be adsorbed onto glutathione sepharose beads (SIGMA Chemical, St. Louis, Mo.) or glutathione derivatized microtiter plates that are then combined with the test compound or the test compound and either the non-adsorbed target polypeptide or an AMM, and the mixture is incubated under conditions conducive to complex formation (e.g., at physiological conditions for salt and pH). Following incubation, the beads or microtiter plate wells are washed to remove any unbound components, the matrix immobilized in the case of beads, and complex formation determined either directly or indirectly. Alternatively, the complexes can be dissociated from the matrix, and the level of AMM binding or activity determined using standard techniques.

Other techniques for immobilizing polypeptides on matrices can also be used in screening assays. Either AMM or its target molecule can be immobilized using biotin-avidin or biotin-streptavidin systems. Biotinylation can be accomplished using many reagents, such as biotin-NHS (N-hydroxy-succinimide; Pierce Chemicals, Rockford, Ill.), and immobilized in wells of streptavidin-coated 96 well plates (Pierce Chemical). Alternatively, Abs reactive with an AMM or other target molecules, but which do not interfere with binding of an AMM to its target molecule, can be derivatized to the wells of the plate, and unbound target or AMM trapped in the wells by Ab conjugation. Methods for detecting such complexes, in addition to those described for the GST-immobilized complexes, include immunodetection of complexes using Abs reactive with AMM or its target, as well as enzyme-linked assays that rely on detecting an enzymatic activity associated with the AMM or target molecule.

(e) Screens to Identify Modulators

Modulators of the expression of an AMM can be identified in a method where a cell is contacted with a candidate compound and the expression of an AMM mRNA or polypeptide in the cell is determined. The expression level of an AMM mRNA or polypeptide in the presence of the candidate compound is compared to AMM mRNA or polypeptide levels in the absence of the candidate compound. The candidate compound can then be identified as a modulator of an AMM mRNA or polypeptide expression based upon this comparison. For example, when expression of an AMM mRNA or polypeptide is greater (i.e., statistically significant) in the presence of the candidate compound than in its absence, the candidate compound is identified as a stimulator of that AMM mRNA or polypeptide expression. Alternatively, when expression of an AMM mRNA or polypeptide is less (statistically significant) in the presence of the candidate compound than in its absence, the candidate compound is identified as an inhibitor of that AMM mRNA or polypeptide expression. The level of AMM mRNA or polypeptide expression in cells can be determined by methods described for detecting AMM mRNA or polypeptide.

(i) Hybrid Assays

In yet another aspect of the invention, AMMs can be used as "bait" in two- or three-hybrid assays (Bartel et al., 1993; Brent et al., WO94/10300, 1994; Iwabuchi et al., 1993; Madura et al., 1993; Saifer et al., U.S. Pat. No. 5,283,317, 1994; Zervos et al., 1993) to identify other polypeptides that bind or interact with AMMs and modulate AMM activities. Such AMM-binding partners are also likely to be involved in the propagation of signals by the AMMs as, for example, upstream or downstream elements of an AMM pathway.

The two-hybrid system is based on the modular nature of most transcription factors, which consist of separable DNA-binding and activation domains. Briefly, the assay utilizes two different DNA constructs. In one construct, the gene that codes for an AMM is fused to a gene encoding the DNA binding domain of a known transcription factor (e.g., GAL4). The other construct, a DNA sequence from a library of DNA sequences that encodes an unidentified polypeptide ("prey" or "sample") is fused to a gene that codes for the activation domain of the known transcription factor. If the "bait" and the "prey" polypeptides are able to interact in vivo and form an AMM-dependent complex, the DNA-binding and activation domains of the transcription factor are brought into close proximity. This proximity allows transcription of a reporter gene (e.g., LacZ) that is operably-linked to a transcriptional regulatory site responsive to the transcription factor. Expression of the reporter gene can be detected, and cell colonies containing the functional transcription factor can be isolated and used to obtain the cloned gene that encodes the AMM-interacting polypeptide.

The invention further pertains to novel agents identified by the aforementioned screening assays and their uses for treatments as described herein.

Detection Assays

Portions or fragments of AMM cDNA sequences—and the complete AMM gene sequences—are useful in themselves. These sequences can be used to: (1) identify an individual from a minute biological sample (tissue typing); and (2) aid in forensic identification of a biological sample.

The AMM sequences of the invention can be used to identify individuals from minute biological samples. In this technique, an individual's genomic DNA is digested with one or more restriction enzymes and probed on a Southern blot to yield unique bands. The sequences of the invention are useful as additional DNA markers for "restriction fragment length polymorphisms" (RFLP; (Smulson et al., U.S. Pat. No. 5,272,057, 1993)).

Furthermore, AMM sequences can be used to determine the actual base-by-base DNA sequence of targeted portions of an individual's genome. AMM sequences can be used to prepare two PCR primers from the 5'- and 3'-termini of the sequences that can then be used to amplify an the corresponding sequences from an individual's genome and then sequence the amplified fragment.

Panels of corresponding DNA sequences from individuals can provide unique individual identifications, as each individual will have a unique set of such DNA sequences due to allelic differences. The sequences of the invention can be used to identify such sequences from individuals and from tissue. The AMM sequences of the invention uniquely represent portions of an individual's genome. Allelic variation occurs to some degree in the coding regions of these sequences, and to a greater degree in the noncoding regions. The allelic variation between individual humans occurs with a frequency of about once ever 500 bases. Much of the allelic variation is due to single nucleotide polymorphisms (SNPs), which include RFLPs.

Each AMM sequence can to some degree be used as standards against which DNA from an individual can be compared for identification purposes. Because greater numbers of polymorphisms occur in noncoding regions, fewer sequences are necessary to differentiate individuals. Noncoding sequences can positively identify individuals with a panel of 10 to 1,000 primers that each yield a noncoding amplified sequence of 100 bases. If predicted coding sequences, such as those in SEQ ID NO:1 are used, a more appropriate number of primers for positive individual identification would be 500–2,000.

Predictive Medicine

The invention also pertains to the field of predictive medicine in which diagnostic assays, prognostic assays, pharmacogenomics, and clinical trial monitoring are used for prognostic (predictive) purposes to treat an individual prophylactically. Accordingly, one aspect of the invention relates to diagnostic assays for determining AMM and/or polynucleotide expression as well as AMM activity, in the context of a biological sample (e.g., blood, serum, cells, tissue, including adipose) to determine whether an individual is afflicted with a disease or disorder, or is at risk of developing a disorder, associated with aberrant AMM expression or activity, including cancer. The invention also provides for prognostic (or predictive) assays for determining whether an individual is at risk of developing a disorder associated with an AMM polynucleotide expression or activity. For example, mutations in an AMM can be assayed in a biological sample. Such assays can be used for prognostic or predictive purpose to prophylactically treat an individual prior to the onset of a disorder characterized by or associated with AMM, polynucleotide expression, or biological activity.

Another aspect of the invention provides methods for determining an AMM activity or polynucleotide expression in an individual to select appropriate therapeutic or prophylactic agents for that individual (pharmacogenomics). Pharmacogenomics allows for the selection of modalities (e.g., drugs, foods) for therapeutic or prophylactic treatment of an individual based on the individual's genotype (e.g., the individual's genotype to determine the individual's ability to respond to a particular agent). Another aspect of the invention pertains to monitoring the influence of modalities (e.g., drugs, foods) on the expression or activity of an AMM in clinical trials.

Diagnostic Assays

An exemplary method for detecting the presence or absence of AMM in a biological sample involves obtaining a biological sample from a subject and contacting the biological sample with a compound or an agent capable of detecting an AMM or an AMM polynucleotide such that the presence of AMM is confirmed in the sample. An agent for detecting an AMM message or DNA is a labeled polynucleotide probe that specifically hybridizes the target AMM mRNA or genomic DNA. The polynucleotide probe can be, for example, a full-length AMM polynucleotide, such as the polynucleotide of SEQ ID NO:1 or a portion thereof, such as an oligonucleotide of at least 15, 30, 50, 100, 250 or 500 nucleotides in length and sufficient to specifically hybridize under stringent conditions to AMM mRNA or genomic DNA.

An agent for detecting an AMM polypeptide is an Ab capable of binding to AMM, preferably an Ab with a detectable label. A preferred biological sample is blood. Detection methods can be used to detect an AMM mRNA, polypeptide, or genomic DNA in a biological sample in vitro as well as in vivo.

The methods further involve obtaining a biological sample from a subject to provide a control, contacting the sample with a compound or agent to detect an AMM, and comparing the presence of AMM in the control sample with the presence of AMM, mRNA or genomic DNA in the test sample.

Kits for detecting AMM in a biological sample may comprise a labeled compound or agent capable of detecting an AMM mRNA or polypeptide in a sample; reagent(s) and/or equipment for determining the amount of an AMM in the sample; and reagent(s) and/or equipment for comparing the amount of an AMM in the sample with a standard.

Prognostic Assays

Diagnostic methods can furthermore be used to identify subjects having, or at risk of developing, a disease or disorder associated with aberrant AMM expression or activity, such as obesity or obesity-related complications. Prognostic assays can be used to identify a subject having or at risk for developing a disease or disorder. A method for identifying a disease or disorder associated with aberrant AMM expression or activity would include a test sample obtained from a subject and detecting an AMM or polynucleotide (e.g., mRNA, genomic DNA). A test sample is a biological sample obtained from a subject. For example, a test sample can be a biological fluid (e.g., serum), cell sample, or tissue.

Prognostic assays can be used to determine whether a subject can be administered a modality (e.g., an agonist, antagonist, peptidomimetic, polypeptide, peptide, polynucleotide, small molecule, food, etc.) to treat a disease or disorder associated with aberrant AMM expression or activity. Such methods can be used to determine whether a subject can be effectively treated with an agent for a disorder, such as obesity. Methods for determining whether a subject can be effectively treated with an agent include obtaining a test sample and detecting an AMM or polynucleotide (e.g., where the presence of the AMM or polynucleotide is diagnostic for a subject that can be administered the agent to treat a disorder associated with aberrant AMM expression or activity).

Genetic lesions in an AMM can be used to determine if a subject is at risk for a disorder, such as obesity. Methods include detecting, in a sample from the subject, the presence or absence of a genetic lesion characterized by at an alteration affecting the integrity of a gene encoding an AMM polypeptide or the mis-expression of AMM. Such genetic lesions can be detected by ascertaining: (1) a deletion of one or more nucleotides from AMM; (2) an addition of one or more nucleotides to AMM; (3) a substitution of one or more nucleotides in AMM, (4) a chromosomal rearrangement of an AMM gene; (5) an alteration in the level of an AMM mRNA transcripts, (6) aberrant modification of an AMM, such as a change genomic DNA methylation, (7) the presence of a non-wild-type splicing pattern of an AMM mRNA transcript, (8) a non-wild-type level of AMM, (9) allelic loss of AMM, and/or (10) inappropriate post-translational modification of AMM polypeptide. There are a large number of known assay techniques that can be used to detect lesions in AMM. Any biological sample containing nucleated cells may be used.

In certain embodiments, lesion detection may use a probe/primer in a polymerase chain reaction (PCR) (e.g., (Mullis, U.S. Pat. No. 4,683,202, 1987; Mullis et al., U.S. Pat. No. 4,683,195, 1987), such as anchor PCR or rapid amplification of cDNA ends (RACE) PCR, or, alternatively, in a ligation chain reaction (LCR) (e.g., (Landegren et al., 1988; Nakazawa et al., 1994), the latter is particularly useful for detecting point mutations in AMM-genes (Abravaya et al., 1995). This method includes collecting a sample from a patient, isolating polynucleotides from the sample (if necessary), contacting the polynucleotides with one or more primers that specifically hybridize to AMM under conditions such that hybridization and amplification of the AMM (if present) occurs, and detecting the presence or absence of an amplification product, or detecting the size of the amplification product and comparing the length to a control sample. PCR and/or LCR are often desirable to use as a preliminary amplification step in conjunction with any of the techniques used for detecting mutations.

Alternative amplification methods include self-sustained sequence replication (Guatelli et al., 1990), transcriptional amplification system (Kwoh et al., 1989); Qβ Replicase (Lizardi et al., 1988), or any other polynucleotide amplification method, followed by the detection of the amplified molecules. These detection schemes are especially useful for the detection of low abundance polynucleotide molecules.

Mutations in AMM from a sample can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes can be used to score for the presence of specific mutations by development or loss of a ribozyme cleavage site.

Hybridizing a sample and control polynucleotides, e.g., DNA or RNA, to high-density arrays containing hundreds or thousands of oligonucleotides probes can identify genetic mutations in AMM (Cronin et al., 1996; Kozal et al., 1996). For example, genetic mutations in AMM can be identified in two-dimensional arrays containing light-generated DNA probes (Cronin et al., 1996). Briefly, a first hybridization array of probes can be used to scan through long stretches of DNA in a sample and control to identify base changes between the sequences by making linear arrays of sequential overlapping probes. This step allows the identification of point mutations. A second hybridization array follows that allows the characterization of specific mutations by using smaller, specialized probe arrays complementary to all variants or mutations detected. Each mutation array is composed of parallel probe sets, one complementary to the wild-type gene and the other complementary to the mutant gene.

Any sequencing reaction can be used to directly sequence the target AMM and detect mutations by comparing the sequence of the sample AMM-with the corresponding wild-type (control) sequence. Examples of sequencing reactions include those based on classic techniques (Maxam and Gilbert, 1977; Sanger et al., 1977). Any of a variety of automated sequencing procedures can be used when performing diagnostic assays (Naeve et al., 1995) including sequencing by mass spectrometry (Cohen et al., 1996; Griffin and Griffin, 1993; Koster, WO94/16101, 1994).

Other methods for detecting mutations in the AMM include those in which protection from cleavage agents is used to detect mismatched bases in RNA/RNA or RNA/DNA heteroduplexes (Myers et al., 1985). In general, the technique of "mismatch cleavage" starts by providing heteroduplexes formed by hybridizing (labeled) RNA or DNA containing the wild-type AMM sequence with potentially mutant RNA or DNA obtained from a sample. The double-stranded duplexes are treated with an agent that cleaves single-stranded regions of the duplex such as those that arise from base pair mismatches between the control and sample strands. For instance, RNA/DNA duplexes can be treated with RNase and DNA/DNA hybrids treated with S₁ nuclease to enzymatically digest the mismatched regions. In other embodiments, either DNA/DNA or RNA/DNA duplexes can be treated with hydroxylamine or osmium tetroxide and with piperidine in order to digest mismatched regions. The digested material is then separated by size on denaturing polyacrylamide gels to determine the mutation site (Grompe et al., 1989; Saleeba and Cotton, 1993). The control DNA or RNA can be labeled for detection.

Mismatch cleavage reactions may employ one or more polypeptides that recognize mismatched base pairs in double-stranded DNA (DNA mismatch repair) in defined systems for detecting and mapping point mutations in AMM cDNAs obtained from samples of cells. For example, the mutY enzyme of E. coli cleaves A at G/A mismatches and the thymidine DNA glycosylase from HeLa cells cleaves T at G/T mismatches (Hsu et al., 1994). According to an exemplary embodiment, a probe based on a wild-type AMM sequence is hybridized to a cDNA or other DNA product from a test cell(s). The duplex is treated with a DNA mismatch repair enzyme, and the cleavage products, if any, can be detected from electrophoresis protocols or the like (Modrich et al., U.S. Pat. No. 5,459,039, 1995).

Electrophoretic mobility alterations can be used to identify mutations in AMM. For example, single strand conformation polymorphism (SSCP) may be used to detect differences in electrophoretic mobility between mutant and wild type polynucleotides (Cotton, 1993; Hayashi, 1992; Orita et al., 1989). Single-stranded DNA fragments of sample and control AMM polynucleotides are denatured and then renatured. The secondary structure of single-stranded polynucleotides varies according to sequence; the resulting alteration in electrophoretic mobility allows detection of even a single base change. The DNA fragments may be labeled or detected with labeled probes. Assay sensitivity can be enhanced by using RNA (rather than DNA), in which the secondary structure is more sensitive to a sequence changes. The method may use heteroduplex analysis to separate double stranded heteroduplex molecules on the basis of changes in electrophoretic mobility (Keen et al., 1991).

The migration of mutant or wild-type fragments can be assayed using denaturing gradient gel electrophoresis (DGGE; (Myers et al., 1985)). In DGGE, DNA is modified to prevent complete denaturation, for example by adding a GC clamp of approximately 40 bp of high-melting, GC-rich DNA by PCR. A temperature gradient may also be used in place of a denaturing gradient to identify differences in the mobility of control and sample DNA (Rossiter and Caskey, 1990).

Examples of other techniques for detecting point mutations include selective oligonucleotide hybridization, selective amplification, or selective primer extension. For example, oligonucleotide primers can be prepared in which the known mutation is placed centrally and then hybridized to target DNA under conditions that permit hybridization only if a perfect match is found (Saiki et al., 1986; Saiki et al., 1989). Such allele-specific oligonucleotides are hybridized to PCR-amplified target DNA or a number of different mutations when the oligonucleotides are attached to the hybridizing membrane and hybridized with labeled target DNA.

Alternatively, allele specific amplification technology that depends on selective PCR amplification may be used. Oligonucleotide primers for specific amplifications may carry the mutation of interest in the center of the molecule (so that amplification depends on differential hybridization (Gibbs et al., 1989)) or at the extreme 3'-terminus of one primer where, under appropriate conditions, mismatch can prevent, or reduce polymerase extension (Prosser, 1993). Novel restriction sites in the region of the mutation may be introduced to create cleavage-based detection (Gasparini et al., 1992). Amplification may also be performed using Taq ligase (Barany, 1991). In such cases, ligation occurs only if there is a perfect match at the 3'-terminus of the 5' sequence, allowing detection of a known mutation by scoring for amplification.

The described methods may be performed, for example, by using pre-packaged kits comprising at least one probe (polynucleotide or Ab) that may be conveniently used in clinical settings to diagnose patients exhibiting symptoms or family history of a disease or illness involving an AMM.

Furthermore, any cell type or tissue in which an AMM is expressed may be utilized in prognostic assays.

Pharmacogenomics

Agents or modulators that have a stimulatory or inhibitory effect on an AMM activity or expression, as identified by a screening assay, can be administered to individuals to treat prophylactically or therapeutically. In conjunction with such treatment, the pharmacogenomics (i.e., the study of the relationship between a subject's genotype and the subject's response to a foreign modality, such as a food, compound or drug) may be considered. Metabolic differences of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Pharmacogenomics can further be used to determine appropriate dosages and therapeutic regimens. Accordingly, the activity of an AMM, expression of an AMM polynucleotide, or AMM mutation(s) in an individual can be determined to guide the selection of appropriate agent(s) for therapeutic or prophylactic treatment.

Pharmacogenomics deals with clinically-significant hereditary variations in the response to modalities due to altered modality disposition and abnormal action in affected persons (Eichelbaum and Evert, 1996; Linder et al., 1997). In general, two pharmacogenetic conditions can be differentiated: (1) genetic conditions transmitted as a single factor altering the interaction of a modality with the body (altered drug action) or (2) genetic conditions transmitted as single factors altering the way the body acts on a modality (altered drug metabolism). These pharmacogenetic conditions can occur either as rare defects or as polynucleotide polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) explains the phenomena of some patients who show exaggerated drug response and/or serious toxicity after taking a standard dose. These polymorphisms are expressed in two phenotypes in the population, the extensive metabolizer (EM) and poor metabolizer (PM). The prevalence of PM is different among different populations. For example, the CYP2D6 gene is highly polymorphic and several mutations have been identified in PM that lead to the absence of functional CYP2D6. Poor metabolizers due to mutant CYP2D6 and CYP2C19 frequently experience exaggerated drug responses and side effects when they receive standard doses. If a metabolite is the active therapeutic moiety, PM shows no therapeutic response, as demonstrated for the analgesic effect of codeine mediated by its CYP2D6-formed metabolite morphine. At the other extreme are the ultra-rapid metabolizers who are unresponsive to standard doses. Recently, the molecular basis of ultra-rapid metabolism has been identified to be due to CYP2D6 gene amplification.

The activity of an AMM, expression of an AMM polynucleotide, or mutation content of an AMM in an individual can be determined to select appropriate agent(s) for therapeutic or prophylactic treatment of the individual. In addition, pharmacogenetic studies can be applied to genotyping polymorphic alleles encoding drug-metabolizing enzymes to identify an individual's drug responsiveness phenotype. This knowledge, when applied to dosing or drug selection, can avoid adverse reactions or therapeutic failure and thus enhance therapeutic or prophylactic efficiency when treating a subject with an AMM modulator, such as a modulator identified by one of the described exemplary screening assays.

Monitoring Effects During Clinical Trials

Monitoring the influence of agents (e.g., drugs, compounds) on the expression or activity of an AMM can be applied not only in basic drug screening, but also in clinical trials. For example, the effectiveness of an agent determined by a screening assay to increase expression of an AMM, polypeptide levels, or up-regulate an AMM activity can be monitored in clinical trails of subjects exhibiting decreased AMM expression, polypeptide levels, or down-regulated AMM activity. Alternatively, the effectiveness of an agent determined to decrease AMM expression, polypeptide levels, or down-regulate an AMM activity, can be monitored in clinical trials of subjects exhibiting increased AMM expression, polypeptide levels, or up-regulated AMM activity. In such clinical trials, the expression or activity of an AMM and, preferably, other genes that have been implicated in, for example, obesity, can be used as a "read out" or markers for a particular cell's responsiveness.

For example, genes, including AMM, that are modulated in cells by treatment with a modality (e.g., food, compound, drug or small molecule) can be identified. To study the effect of agents on obesity, for example, in a clinical trial, cells can be isolated and RNA prepared and analyzed for the levels of expression of an AMM and other genes implicated in obesity. The gene expression pattern can be quantified by Northern blot analysis, nuclear run-on or RT-PCR experiments, or by measuring the amount of polypeptide, or by measuring the activity level of an AMM or other gene products. In this manner, the gene expression pattern itself can serve as a marker, indicative of the cellular physiological response to the agent. Accordingly, this response state may be determined before, and at various points during, treatment of the individual with the agent.

The invention provides a method for monitoring the effectiveness of treatment of a subject with an agent (e.g., an agonist, antagonist, polypeptide, peptide, peptidomimetic, polynucleotide, small molecule, food or other drug candidate identified by the screening assays described herein) comprising the steps of (1) obtaining a pre-administration sample from a subject; (2) detecting the level of expression of an AMM, mRNA, or genomic DNA in the preadministration sample; (3) obtaining one or more post-administration samples from the subject; (4) detecting the level of expression or activity of the AMM, mRNA, or genomic DNA in the post-administration samples; (5) comparing the level of expression or activity of the AMM, mRNA, or genomic DNA in the pre-administration sample with the AMM, mRNA, or genomic DNA in the post administration sample or samples; and (6) altering the administration of the agent to the subject accordingly. For example, increased administration of the agent may be desirable to increase the expression or activity of AMM to higher levels than detected, i.e., to increase the effectiveness of the agent. Alternatively, decreased administration of the agent may be desirable to decrease expression or activity of AMM to lower levels than detected, i.e., to decrease the effectiveness of the agent.

Methods of Treatment

The invention provides for both prophylactic and therapeutic methods of treating a subject at risk of (or susceptible to) a disorder or having a disorder associated with aberrant AMM expression or activity, such as obesity.

Disease and Disorders

Diseases and disorders that are characterized by increased AMM levels or biological activity may be treated with therapeutics that antagonize (i.e., reduce or inhibit) activity. Antagonists may be administered in a therapeutic or prophylactic manner. Therapeutics that may be used include: (1) AMM polypeptides, or analogs, derivatives, fragments or homologs thereof; (2) Abs to an AMM polypeptide; (3) AMM polynucleotides; (4) administration of anti-sense polynucleotide and polynucleotides that are "dysfunctional" (i.e., due to a heterologous insertion within the coding sequences) that are used to eliminate endogenous function of by homologous recombination (Capecchi, 1989); or (5) modulators (i.e., inhibitors, agonists and antagonists, including additional peptide mimetic of the invention or Abs specific to AMM) that alter the interaction between AMM and its binding partner.

Diseases and disorders that are characterized by decreased AMM levels or biological activity may be treated with therapeutics that increase (i.e., are agonists to) activity. Therapeutics that upregulate activity may be administered therapeutically or prophylactically. Therapeutics that may be used include peptides, or analogs, derivatives, fragments or homologs thereof; or an agonist that increases bioavailability.

Increased or decreased levels can be readily detected by quantifying peptide and/or RNA, by obtaining a patient tissue sample (e.g., from biopsy tissue) and assaying in vitro for RNA or peptide levels, structure and/or activity of the expressed peptides (or AMM mRNAs). Methods include immunoassays (e.g., Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, and the like).

Prophylactic Methods

The invention provides a method for preventing in a subject a disease or condition associated with an aberrant AMM expression or activity, by administering an agent that modulates expression of an AMM or at least one AMM activity. Subjects at risk for a disease that is caused or contributed to by aberrant AMM expression or activity can be identified by, for example, any or a combination of diagnostic or prognostic assays. Administration of a prophylactic agent can occur prior to the manifestation of symptoms characteristic of the AMM aberrancy, such that a disease or disorder is prevented or, alternatively, delayed in its progression. Depending on the type of AMM aberrancy, for example, an AMM agonist or antagonist can be used to treat the subject. The appropriate agent can be determined based on screening assays.

Therapeutic Methods

Modulating AMM expression or activity can be used therapeutically. Such a modulatory method involves contacting a cell with an agent that modulates one or more of the activities of an AMM activity associated with the cell. An agent that modulates an AMM activity can be a polynucleotide or a polypeptide, a naturally-occurring cognate ligand of an AMM, a peptide, an AMM peptidomimetic, or other small molecule. The agent may stimulate an AMM activity. Examples of such stimulatory agents include active AMM, and an AMM polynucleotide molecule that has been introduced into the cell. In another embodiment, the agent inhibits an AMM activity. Examples of inhibitory agents include anti-sense AMM and anti-AMM Abs. Modulatory methods can be performed in vitro (e.g., by culturing the cell with the agent) or, alternatively, in vivo (e.g., by administering the agent to a subject). As such, the invention provides methods of treating an individual afflicted with a disease or disorder characterized by aberrant expression or activity of an AMM polypeptide or polynucleotide. For example, the method involves administering an agent (e.g., an agent identified by a screening assay), or combination of agents that modulates (e.g., up-regulates or down-regulates) AMM expression or an activity. Alternatively, the method involves administering an AMM or polynucleotide molecule as therapy to compensate for reduced or aberrant AMM expression or activity.

Stimulation of an AMM activity is desirable in situations in which an AMM is abnormally down-regulated and/or in which increased AMM activity is likely to have a beneficial effect.

Determination of the Biological Effect of the Therapeutic

Suitable in vitro or in vivo assays can be performed to determine the effect of a specific therapeutic and whether its administration is indicated for treatment of the affected tissue.

In various specific embodiments, in vitro assays may be performed with representative cells of the type(s) involved in the patient's disorder, to determine if a given therapeutic exerts the desired effect upon the cell type(s). Modalities for use in therapy may be tested in suitable animal model systems including, but not limited to rats, mice, chicken, cows, monkeys, rabbits, and the like, prior to testing in human subjects. Similarly, for in vivo testing, any of the animal model system known in the art may be used prior to administration to human subjects.

Prophylactic and Therapeutic uses of the Compositions of the Invention

AMM polynucleotides and polypeptides are useful in potential prophylactic and therapeutic applications implicated in a variety of disorders including obesity.

As an example, a cDNA encoding an AMM may be useful in gene therapy, and the polypeptide may be useful when administered to a subject in need. The compositions of the invention will have efficacy for treatment of patients suffering from obesity.

AMM polynucleotides or fragments are also useful in diagnostic applications, wherein the presence or amount of the polynucleotide or the polypeptide is to be assessed. A further use could be as an anti-bacterial molecule (i.e., some peptides have been found to possess anti-bacterial properties). These materials are further useful in the generation of Abs that immunospecifically bind to the novel substances of the invention for use in therapeutic or diagnostic methods.

EXAMPLES

The following examples are included to demonstrate preferred embodiments of the present invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention.

Example 1

Fasting/feeding Experiments
Experimental Design Details
Four groups of mice; n=5/group.
1. Ad lib fed mice.
2. Mice fasted for 4 hours.
3. Mice fasted for 24 hours and then refed ad lib for 24 hours.
4. Mice fasted for 48 hours
5. Mice fasted for 48 hours and then refed ad lib for 24 hours.

All studies were done in accordance with guidelines set forth by the Institutional Animal Care and Use Committee at Genentech, Inc. (South San Francisco, Calif.). Male FVB-N/J mice (Jackson Labs; Bar Harbor, Me.) were received at 3 weeks of age and housed at 2 mice/cage until tissue harvest at 6 weeks of age. All mice were fed rodent chow ad libitum (Chow 5010, Ralston Purina; St. Louis, Mo.) and housed on a 12 hour/12 hour light/dark cycle (lights on 06:00 a.m.) at 22° C. Following $CO_2$-induced euthanasia, stomach tissue was excised, carefully cleaned, and snap-frozen in liquid nitrogen for subsequent RNA preparation.

Samples from each treatment group were transferred to CuraGen Corp. (New Haven; Conn.), RNA prepared and reverse-transcribed, and subjected to Quantitative Expression Analysis (QEA; Shimkets, et al., 1999).

The mice were FVB, a more recently adopted strain (as compared to, for example C57B1/6), that was mostly inbred.

Example 2

GeneCalling (Shimkets et al., 1999)

RNA Isolation

Total RNA was isolated with Trizol (Life Technologies, Grand Island, N.Y.) using 0.1 volume of bromochloropropane for phase separation (Molecular Research Center; Cincinnati, Ohio), and treated with DNase I (Promega; Madison, Wis.) in the presence of 0.01 M dithiothreitol (DTT) and 1 U/1 RNasin (Promega). Following phenol/chloroform extraction, RNA quality was evaluated by spectrophotometry and formaldehyde agarose gel electrophoresis, and yield was estimated by fluorometry with OliGreen (Molecular Probes; Eugene, Oreg.). Poly-A+ RNA was prepared from 100 g total RNA using oligo(dT) magnetic beads (PerSeptive; Cambridge, Mass.), and quantified with fluorometry.

First-strand cDNA was prepared from 1.0 g of poly(A)+ RNA with 200 pmol oligo(dT)25V (V=A, C or G) using 400 U of Superscript II reverse transcriptase (BRL). Second-strand synthesis was performed at 16° C. for 2 hours after addition of 10 U of E. coli DNA ligase, 40 U of E. coli DNA polymerase, and 3.5 U of E. coli RNase H (all from BRL). T4 DNA polymerase (5 U) was added, incubated for 5 minutes at 16° C., followed by treatment with arctic shrimp alkaline phosphatase (5 U; United States Biochemicals; Cleveland, Ohio) at 37° C. for 30 minutes. cDNA was purified by phenol/chloroform extraction, and the yield was estimated using fluorometry with PicoGreen (Molecular Probes).

cDNA fragmentation was achieved by digestion in a 50 μl reaction mixture containing 5 U of restriction enzyme (6 base-pair cutters) and 1 ng of double-stranded cDNA. Eighty separate sets of cDNA fragmentation reactions were conducted, each with a different pair of restriction enzymes. These were then ligated to complementary amplification tags with ends compatible to the 5' and 3' ends of the fragments at 16° C. for 1 hour in 10 mM ATP, 2.5% PEG, 10 units T4 DNA ligase, and 1 ligase buffer. Amplification was then performed after addition of 2 µl 10 mM dNTP, 5 µl 10 TB buffer (500 mM Tris, 160 mM (NH4)$_2$SO$_4$, 20 mM MgCl$_2$, pH 9.15), 0.25 µl Klentaq (Clontech Laboratories; Palo Alto, Calif.): PFU (Stratagene, La Jolla, Calif.) (16:1), 32.75 µl H2O. Amplification was carried out for 20 cycles (30 seconds at 96° C., 1 minute at 57° C., 2 minutes at 72° C.), followed by 10 minutes at 72° C. PCR products were purified using streptavidin beads (CPG; Lincoln Park, N.J.). After washing the beads twice with buffer 1 (3 M NaCl, 10 mM Tris-HCl, 1 mM EDTA, pH 7.5), 20 µl of buffer 1 was mixed with the PCR product for 10 minutes at room temperature, separated with a magnet, and washed once with buffer 2 (10 mM Tris, 1 mM EDTA, pH 8.0). The beads were then dried and resuspended in 3 µl of buffer 3 (80% (vol/vol) formamide, 4 mM EDTA, 5% TAMRA- or ROX-tagged molecular size standards (PE-Applied Biosystems, Foster City, Calif.). Following denaturation (96° C. for 3 minutes), samples were loaded onto 5% polyacrylamide, 6 M urea, 0.5 Tris borate EDTA ultrathin gels and electrophoresed on a Niagara instrument. PCR products were visualized by virtue of the fluorescent FAM label at the 5' end of one of the PCR primers, which ensures that all detected fragments have been digested by both enzymes.

Gel Interpretation

Electrophoresis data was processed using the Open Genome Initiative (OGI) software. Gel images were first visually checked and tracked. Each lane contained the FAM-labeled products of a single reaction plus a sizing ladder spanning the range from 50 to 500 bp. The ladder peaks provide a correlation between camera frames (collected at 1 Hz) and DNA fragment size in base pairs. After tracking, lanes were extracted and the peaks in the sizing ladder were found. Linear interpolation between the ladder peaks converted the fluorescence traces from frames to base pairs. A final quality control step checked for low signal-to-noise, poor peak resolution, missing ladder peaks, and lane-to-lane bleed. Data that pass all of these criteria were submitted as point-by-point length versus amplitude addresses to an Oracle 8 database.

Difference Identification

For each restriction enzyme pair in each sample set a composite trace was calculated, compiling all the individual sample replicates followed by application of a scaling algorithm for best fit to normalize the traces of the experimental set versus that of the control. The scaled traces are then compared on a point-by-point basis to define areas of amplitude difference that meet the minimum prespecified threshold for a significant difference. Once a region of difference has been identified, the local maximum for the corresponding traces of each set was then determined. The variance of the difference was calculated by the following expression:

$$\sigma 2_\Delta(j) = \lambda_1(j)^2 \sigma^2_{Total}(j:S_1) + \lambda_2(j)^2 \sigma^2_{Total}(j:S_2)$$

where $\lambda_1(j)$ and $\lambda_2(j)$ represent scaling factors and (j:S) represent scaling factors and (j:S) represents the trace composite values over multiple samples. The probability that the difference is statistically significant is calculated by:

$$P(j) = 1 - \int_{-\Delta}^{\Delta} dy (1/\sqrt{\{2\pi\sigma^2_\Delta\}}) \exp(-y^2/2\sigma^2_\Delta)$$

where y is the relative intensity. All difference peaks are stored as unique database addresses in the specified expression difference analysis.

Gene Confirmation by Oligonucleotide Poisoning

Restriction fragments that map in end sequence and length to known rat genes are used as templates for the design of unlabeled oligonucleotide primers. An unlabeled oligonucleotide designed against one end of the restriction fragment is added in excess to the original reaction, and is reamplified for an additional 15 cycles. This reaction is then electrophoresed and compared to a control reaction reamplified without the unlabeled oligonucleotide to evaluate the selective diminution of the peak of interest.

RNA Doping

DNA templates for RNA in vitro transcription were generated by PCR amplification using cloned human cDNAs as templates. PCR primers were complementary to plasmid sequences flanking the cDNA inserts. In addition, the sense primer contained the T7 RNA polymerase consensus sequence, and the anti-sense primer included a stretch of 25 thymidines for the generation of polyadenylated transcripts. In vitro transcription was performed using the MaxiScript transcription kit (Ambion; Austin, Tex.). The transcripts were poly-A selected on biotin-oligo(dT)25 bound to streptavidin MPG beads (CPG Inc.). The RNA products ranged in size between 1,100 and 2,000 nucleotides. The integrity of the products was monitored by agarose gel electrophoresis, and the concentration determined by fluorometry using RiboGreen dye (Molecular Probes) on a SpectraFluor fluorometer (Tecan; Grundig, Austria). The in vitro transcribed RNAs were mixed at defined ratios with HeLa cell poly-A+ RNA (ATCC) and the RNA was converted to cDNA and subjected to GeneCalling chemistry and analysis as described.

Example 3

Identification of AMM

A novel mouse fragment was identified as differentially-expressed, showing two-fold induction in translation with feeding after fasting. This sequence was extended through CuraTools SeqExtender as described in Example 4 (below). BlastN analyses indicated that the novel mouse fragment matched equally (95%) to two known sequences: *Mus musculus* acidic mammalian chitinase precursor (1530 bp; GenBank Accession No: BC011134; (SEQ ID NO: 10) and *Mus musculus* eosinophil chemotactic cytokine (1538 bp); GenBank Accession No: AF290003; (SEQ ID NO:9).

Example 4

Identification of Novel Acidic Mammalian Molecule

This sequence was assembled from the following components using CuraTools SeqExtender (The results are also present in Table 2 (reproduced below)):

Consensus extension of 1.3610e1167.4cgmm10e1167.4_37627_215 using the 32 sequences: 1.3610e1167.4cgmm10e1167.4_37627_215-, est:gb___AA839173.1-, est:gb__AV061588.1+, est:gb__AV071906.1+, est:gb__AV071959.1+, est:gb__AV072265.1+, est:gb__AV072325.1+, est:gb__AV072529.1+, est:gb__AV072767.1+, est:gb__AV073012.1+, est:gb__AV073124.1+, est:gb__AV074011.1+, est:gb__AV074108.1+, est:gb__AV074945.1+, est:gb__AV076117.1+, est:gb__AV078806.1+, est:gb__AV087174.1+, est:gb__AV090347.1+, est:gb__AV373869.1+, est:gb__AV374941.1+, est:gb__AV375338.1+, est:gb__AV375770.1+, est:gb__AV376169.1+, est:gb__AV377439.1+, est:gb__AV377816.1+, est:gb__AV377825.1+, est:gb__AV378355.1+, est:gb__AV378424.1+, est:gb__AV378736.1+, est:gb__AV378822.1+, est:gb__AV378937.1+, est:gb__BF450121.1

TABLE 2

(reproduced from above)
1.3610e1167.4cgmm10e1167.4_37627_215EXT
polynucleotide sequence

```
gtaggaagtg agagtgtgggg tggaagcttc cggaggaagc tttggaggca gtggattttg  60  (SEQ ID NO:1)

tgccgacaaa gcagatggcc tttaccctgt ggcagatgac agaaatgctt tttggcagtg 120
catcaatgga atcacatacc agcagcattg tcaagcaggg cttgtttttg ataccagctg 180
taattgctgc aactggccat gaacctaatg ccatttttcc agaaattttt gcattttcct 240
ttattcctca ccaaaagtaa cttttttccc tttaaccttta tgcaataaaa ttggtagccg 300
taaaaaaaaa aaaaaaaa 319
```

Example 5

Identification of the Polypeptide Sequence for AMM

The protein sequence encoded by SEQ ID NO:1 (Table 2) represents an ORF (frame 2; SEQ ID NO:2) found in AMM (1.3610e1167.4cgmm10e1167.4_37627_215_EXT polynucleotide sequence; SEQ ID NO:1). (Keywords for this protein: Translated Protein—Frame: 2-Nucleotide 5 to 199)

TABLE 3

(reproduced from above)
1.3610e1167.4cgmm10e1167.4_37627_215_EXT
amino acid sequence

```
Glu Val Arg Val Gly Val Glu Ala Ser Gly Gly Ser Phe Gly Gly Ser  (SEQ ID NO:2)
1               5                   10                  15

Gly Phe Cys Ala Asp Lys Ala Asp Gly Leu Tyr Pro Val Ala Asp Asp
                20              25                  30

Arg Asn Ala Phe Trp Gln Cys Ile Asn Gly Ile Thr Tyr Gln Gln His
            35              40                  45

Cys Gln Ala Gly Leu Val Phe Asp Thr Ser Cys Asn Cys Cys Asn Trp
    50              55                  60

Pro
65
```

Example 6

Use of AAM as a Hybridization Probe (Prophetic Example)

The following method describes use of a nucleotide sequence encoding AAM as a hybridization probe.

DNA comprising the coding sequence of full-length or mature AAM (or unique fragments thereof) is employed as a probe to, for example, detect the presence and quantity of AAM mRNA in a sample (for example, in a diagnostic setting) or to assess a genetic lesion.

Radiolabeled AAM-derived probe is hybridized to filters on which, for example, mRNA has been blotted, in a solution of 50% formamide, 5×SSC, 0.1% SDS, 0.1% sodium pyrophosphate, 50 mM sodium phosphate, pH 6.8, 2× Denhardt's solution, and 10% dextran sulfate at 42° C. for 20 hours. Filters are then washed in 0.1×SSC and 0.1% SDS at 42° C., and the signal detected by exposing the blots to X-ray film. As appropriate, internal controls may be used (for example, measuring the amount of a house-keeping gene when mRNA is being quantified).

Example 7

Expression of AMM E. coli (Prophetic Example)

This example illustrates preparation of an unglycosylated form of AMM by recombinant expression in E. coli.

The DNA sequence encoding AMM is initially amplified using selected PCR primers. The primers optimally contain restriction enzyme sites which correspond to restriction sites in a selected expression vector, and preferably, will enable the correct 5' to 3' orientation of the insert. A variety of expression vectors can be employed, such as the common pBR322 (derived from E. coli; (Bolivar at al., 1977)) that contains ampicillin and tetracycline resistance genes. The vector is digested with an appropriate restriction enzyme and dephosphorylated. The PCR-amplified sequences are then ligated into the vector in vitro using ligase. Preferably, the finished vector includes sequences that encode for an antibiotic resistance gene (such as ampicillin and tetracycline), a trp promoter, a poly-His leader sequence (including the first six STII codons, poly-His sequence, and enterokinase cleavage site; this fusion to the AMM gene allows simple purification of the AMM polypeptides using nickel columns; enterokinase will liberate the poly-His fusion from the AMM polypeptide), the AMM coding region, lambda transcription terminator, and an argU gene.

The ligation mixture is then used to transform a selected E. coli (such as DHα) strain and transformants identified by their ability to grow on Lauria broth (LB) plates supplemented with selective antibiotics (as governed by the chosen vector); antibiotic-resistant colonies are then selected. Plasmid DNA can be isolated and confirmed by restriction analysis and DNA sequencing.

Selected clones can be grown overnight in liquid culture medium such as LB broth supplemented with antibiotics. The overnight culture can subsequently be used to inoculate a larger scale culture. The cells are then grown to a desired optical density (3–5 at $OD_{60D}$) without agitation, during which the expression promoter is activated, expressing the AMM polypeptide. The cultures are then diluted 50–100-fold in CRAP media (prepared by mixing 3.57 g $(NH_4)_2SO_4$, 0.71 g sodium citrate·$H_2O$, 1.07 g KCl, 5.36 g yeast extract (such as Difco), 5.36 g Sheffield hycase SF in 500 mL water, as well as 110 mM MPOS, pH 7.3, 0.55% (w/v) glucose and 7mM $MgSO_4$) and grown for approximately 20–30 hours at 30° C. with agitation. Samples are removed to verify expression by SDS-PAGE analysis, and the bulk culture is centrifuged to pellet the cells. Cell pellets are frozen until purification and refolding.

E. coli paste from 0.5 to 1 L fermentations (6–10 g pellets) is resuspended in 10 volumes (w/v) in 7 M guanidine, 20 mM Tris (pH 8) buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is then centrifuged at 40,000 rpm in a Beckman Ultracentifuge for 30 minutes. The supernatant is diluted with 3–5 volumes of metal chelate column buffer(6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by absorbance at 280 nm using the calculated extinction coefficient based on its amino acid sequence.

To refold the proteins, the sample is slowly diluted into freshly prepared refolding buffer consisting of 20 mM Tris (pH 8.6),0.3 M NaCl, 2.5 M urea, 5 mM cysteine, 20 mM glycine and 1 mM EDTA. Refolding volumes are chosen so that the final protein concentration is between 50 to 100 μg/ml. The refolding solution is stirred gently at 4° C. for 12–36 hours. The refolding reaction is quenched by the addition of trifluoracetic acid (TFA) to a final concentration of 0.4% (pH of approximately 3). Before further purification, the solution is again filtered through a 0.22 micron filter, and acetonitrile is added to 2–10% final concentration. The refolded protein is chromatographed on a Poros R1/H reversed-phase column using a mobile buffer of 0.1% TFA and eluted with a gradient of acetonitrile from 10% to 80%. Aliquots of fractions with $A_{280}$ absorbance are analyzed on SDS polyacrylamide gels, and fractions containing homogeneous refolded protein are pooled. Generally, the properly re-folded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin.

Fractions containing the desired folded AMM polypeptide are pooled and the acetonitrile removed using a gentle stream of nitrogen directed at the solution. Polypeptides are formulated into 20 mM Hepes (pH 6.8) with 0.14 M NaCl and 4% mannitol by dialysis or by gel filtration using G25 Superfine (Pharmacia) resins equilibrated in the formulation buffer and sterile filtered.

Example 8

Expression of AMM in Mammalian Cells (Prophetic Example)

This example illustrates preparation of a glycosylated form of AMM by recombinant expression in mammalian cells.

The vector, pRK5 (EP 307,247), may be used as an appropriate expression vector. Optionally, the AMM DNA is ligated into pRK5 with selected restriction enzymes to allow insertion of the AMM DNA using conventional ligation methods. The resulting vector is called pRK5-AMM. An appropriate mammalian host cell is selected. For example, the intestinal CaCo-2 cell line, or stomach carcinoma cell lines KATO III and NCI-N87 may be used (all available from ATCC); alternatively, a non-digestive tract-specific cell line may be employed, such as 293 cells (ATCC).

For example, human 293 cells are grown to confluence in tissue culture plates in medium such as DMEM supplemented with fetal calf serum and optionally, nutrient components and/or antibiotics. About 10 μg of pRK5-AMM DNA is mixed with about 1 μg DNA encoding the VA RNA gene (Thimmappaya et al., 1982) and dissolved in 500 nl of 1 mM Tris-HCl, 0.1 mM EDTA, 0.227 M $CaCl_2$. To this mixture is added, dropwise, 500 pl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is then aspirated, and 2 ml of 20% glycerol in PBS is added for 30 seconds. After washing the cells with serum-free medium, fresh medium is added, and the cells are cultured for about 5 days.

Approximately 24 hours after transfection, the culture medium is removed and replaced with culture medium (alone) or culture medium containing 200 μCi/ml $^{35}$S-cysteine and 200 μCi/ml $^{35}$S-methionine. After 12 hours, the medium is collected, concentrated in a spin filter, and loaded onto a SDS-PAGE gel. The processed gel is dehydrated and exposed to X-ray film to detect radio-labeled AMM polypeptide. The cultures containing transfected cells can undergo further incubation (in serum free medium) and the medium tested in bioassays.

Alternatively, AMM can be introduced into 293 cells transiently using the dextran sulfate method (Sompayrac and Dnnia 1981). 293 cells are grown to maximal density in a spinner flask, and 700 ng pRK5-AAM DNA is added. The cells are collected by centrifugation and washed with Phosphate-buffered saline (PBS). The DNA-dextran precipitate is incubated on the cell pellet for 4 hours. The cells are then treated with 20% glycerol for 90 seconds, washed with tissue culture medium, and re-introduced into the spinner flask containing tissue culture medium, 5 pg/ml bovine insulin and 0.1 μg/mI bovine transferrin. After about four days, the conditioned media is centrifuged and filtered to remove cells and debris. The sample containing expressed AMM can then be concentrated and purified by any selected method, such as dialysis and/or column chromatography.

AMM can also be expressed in CHO cells. The pRK5-AMM can be transfected into CHO cells using known reagents, such as $CaPO_4$ or DEAE-dextran. As described above, the cell cultures can be incubated, and the medium replaced with culture medium (alone) or medium containing a radiolabel such as $^{35}$S-methionine. After determining the presence of AMM polypeptide, the culture medium is replaced with serum-free medium. Preferably, the cultures are incubated for about 6 days, and then the conditioned medium is harvested. The medium containing the expressed AMM is then concentrated and purified.

Example 9

Expression of AMM in Baculovirus-infected Insect Cells (Prophetic Example)

For example, the sequence encoding AMM is fused upstream of an epitope tag contained within a Baculovirus expression vector. Useful epitope tags include poly-His and immunoglobulins (like $F_c$ regions of IgG). A variety of plasmids can be used, including plasmids derived from commercially-available plasmids, such as pVL1393 (Novagen). Briefly, the sequence encoding AMM or desired fragment is amplified by PCR with primers complementary to the 5' and 3' regions. The 5' primer can incorporate flanking (selected) restriction enzyme sites. The product is then digested with those selected restriction enzymes and subcloned into the expression vector.

Recombinant *Baculovirus* is generated by co-transfecting the above plasmid and BaculoGold TI virtis DNA (Pharmingen) into *Spodoptera frugiperda* ("Sf9") cells (ATCC CRL 1711) using lipofectin (commercially available from GIBCO-BRL). After 4–5 days of incubation at 28° C., the released virus are harvested and used for further amplifications. Viral infection and protein expression is then performed (O'Reilly 1994).

Expressed poly-His tagged AMM can then be purified, for example by $Ni^{2+}$-chelate affinity chromatography. Extracts are prepared from recombinant virus-infected Sf9 cells as described (Ruppert et al., 1993). Sf9 cells are washed, resuspended in sonication buffer (25 ml Hepes (pH 7.9); 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45, u$\mu$ filter. A Ni-NTA agarose column (Qiagen) is prepared with a bed volume of 5 ml, washed with 25 ml of water and equilibrated with 25 ml of loading buffer. The filtered cell extract is loaded onto the column at 0.5 ml per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein.

After reaching the $A_{280}$ baseline again, the column is developed with a 0 to 500 mM Imidazole gradient in the secondary wash buffer. One 1 ml fractions are collected and analyzed by SDS-PAGE and silver staining or Western blot with Ni2+-NTA-conjugated to alkaline phosphatase (Qiagen). Fractions containing the eluted His-tagged AMM are pooled and dialyzed against loading buffer.

Example 10

Preparation of Antibodies that Bind AMM (Prophetic Example)

Techniques for producing the monoclonal antibodies are known in the art (see above). Immunogens that can be employed include purified AMM, fusion proteins containing AMM, and cells expressing recombinant AMM on the cell surface (or fragments thereof). Selection of the immunogen can be made by the skilled artisan without undue experimentation.

Mice, such as Balb/c, are immunized with the AMM immunogen emulsified in complete Freund's adjuvant and injected subcutaneously or intraperitoneally in an amount from 1–100 μg. Alternatively, the immunogen is emulsified in MPL-TDM adjuvant (Ribi Immunochemical Research; Hamilton, Mont.) and injected into the animal's hind foot pads. The immunized mice are then boosted 10 to 12 days later with additional immunogen emulsified in the selected adjuvant.

Thereafter for several weeks, the mice can also be boosted with additional immunization injections. Serum samples are periodically tested in ELISA assays to detect anti-AMM antibodies.

After a suitable antibody titer has been detected, the animals producing the anti-AMM antibodies are injected with a final intravenous injection of AMM antigen. Three to four days later, the mice are sacrificed, and the spleen cells are harvested. The spleen cells are then fused using 35% polyethylene glycol to a selected murine myeloma cell line such as P3X63AgU. 1 (ATCC). The fusions generate hybridoma cells that are then plated in 96 well tissue culture plates containing HAT (hypoxanthine, aminopterin, and thymidine) medium to inhibit proliferation of non-fused cells, myeloma hybrids, and spleen cell hybrids.

The hybridoma cells are screened in an ELISA for reactivity against AMM polypeptide.

The positive hybridoma cells can be injected intraperitoneally into syngencic Balb/c mice to produce ascites containing the anti-AMM monoclonal antibodies. Alternatively, the hybridoma cells are grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed. Conditioned media from cultured hybidoma cells may be used without purification.

Example 11

Purification of AMM Polypeptides Using Specific Antibodies (Prophetic Example)

Native or recombinant AMM polypeptides can be purified by a variety of standard techniques in the art of protein purification. For example, pro-AMM polypeptide, mature AMM polypeptide, or pre-pro AMM polypeptide is purified by immunoaffinity chromatography using antibodies specific for the AMM polypeptide. In general, an immunoaffinity column is constructed by covalently coupling the anti-AMM polypeptide antibody to an activated chromatographic resin.

Polyclonal immunoglobulins are prepared from immune sera either by precipitation with ammonium sulfate or by purification on immobilized Protein A (Pharmacia LKB Biotechnology; Piscataway, N.J.). Likewise, monoclonal antibodies are prepared from mouse ascites fluid by ammonium sulfate precipitation or chromatography on immobilized Protein G. Partially-purified immunoglobulin is covalently attached to a chromatographic resin, such as CnBr-activated SEPHAROSE (Pharmacia LKB Biotechnology). The antibody is coupled to the resin, the resin is blocked, and the derivative resin is washed according to the manufacturer's instructions. Such an immunoaffinity column is utilized in the purification of AMM polypeptide by preparing a fraction from cells containing soluble AMM polypeptide. This preparation is derived by solubilization of the whole cell or of a subcellular fraction obtained via differential centrifugation, by the addition of detergent or by other methods. Alternatively, soluble AMM polypeptide can be secreted in useful quantity into the medium in which the cells are grown, by employing a heterologous secretion signal peptide.

A soluble AMM polypeptide-containing preparation is passed over the immunoaffinity column, and the column is washed under conditions that allow the preferential absorbance of AMM polypeptide (e.g., high ionic strength buffers in the presence of detergent). The column is eluted under conditions that disrupt antibody/AMM polypeptide binding (e.g., a low pH buffer (pH 2–3), or a high concentration of a chaotrope, such as urea orthiocyanateion), and AMM polypeptide is collected.

Example 12

Preparation of AMM Antisense Oligonucleotides (Prophetic Example)

Oligonucleotide Synthesis Unsubstituted and substituted phosphodiester (P=O) oligonucleotides are synthesized on an automated DNA synthesizer (Applied Biosystems model 380B) using standard phosphoramidite chemistry with oxidation by iodine. Phosphorothioates (P=S) are synthesized as for the phosphodiester oligonucleotides, except the standard oxidation bottle is replaced by 0.2 M solution of $^3$H-1,2-benzodithiole-3-one 1,1-dioxide in acetonitrile for the stepwise thiation of the phosphite linkages. The thiation wait step is increased to 68 seconds and is followed by the capping step. After cleavage from the CPG column and deblocking in concentrated ammonium hydroxide at 55° C. (18 hours), the oligonucleotides are purified by precipitating twice with 2.5 volumes of ethanol from a 0.5 M NaCl solution. Phosphinate oligonucleotides are prepared as described (U.S. Pat. No. 5,508,270). Alkyl phosphonate oligonucleotides are prepared as described (U.S. Pat. No. 4,469,863). 3'-deoxy-3'-methylene phosphonate oligonucleotides are prepared as described (U.S. Pat. Nos. 5,610,289 or 5,625,050). Phosphoramidite oligonucleotides are prepared as described (U.S. Pat. No. , 5,256,775 or U.S. Pat. No. 5,366,878). Alkylphosphonothioate oligonucleotides are prepared as described (WO 94/17093 and WO 94/02499, respectively). 3'-Deoxy-3'-amino phosphoramidate oligonucleotides are prepared (U.S. Pat. No. 5,476,925). Phosphotriester oligonucleotides are prepared as described (U.S. Pat. No. 5,023,243). Borano phosphate oligonucleotides are prepared as described (U.S. Pat. Nos. 5,130,302 and 5,177, 198). Methylenemethylimino (MMI)-linked oligonucleosides, methylenedimethylhydrazo (MDH)-linked oligonucleosides, methylenecarbonylamino-linked oligonucleosides (amide-3 linked oligonucleosides), and methyleneaminocarbonyl linked oligonucleosides (amide-4 linked oligonucleosides), as well as mixed backbone compounds having, for instance, alternating MMI and P=O or P=S linkages are prepared as described (U.S. Pat. Nos. 5,378,825, 5,386,023, 5,489,677, 5,602,240 and 5,610,289). Formacetal- and thioformacetal-linked oligonucleosides are prepared as described (U.S. Pat. Nos. 5,264,562 and 5,264, 564). Ethylene oxide-linked oligonucleosides are prepared as described (U.S. Pat. No. 5,223,618).

PNA Synthesis Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 4: 5–23 (1996). They are also prepared in accordance with U.S. Pat. Nos. 5,539,082, 5,700,922, and 5,719,262.

Synthesis of Chimeric Oligonucleotides [2'-0-Me]-[2'-deoxy]-[2'-0-Me] Chimeric Phosphorothioate Oligonucleotides: Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 seconds repeated four times for RNA, and twice for 2'-O-methyl. The fully-protected oligonucleotide is cleaved from the support, and the phosphate group is deprotected in 3:1 ammonia:ethanol at room temperature (22° C.) overnight then lyophilized. Treatment in methanolic ammonia for 24 hours at room temperature is then done to deprotect all bases and sample is again lyophilized. The pellet is resuspended in 1M TBAF in THF for 24 hours at room temperature to deprotect the 2' positions. The reaction is then quenched with 1M TEAA, and the sample is then reduced to ½ volume by Rotovac before being desalted on a G-25 size exclusion column. The recovered oligonucleotides are then analyzed spectrophotometrically for yield and purity by capillary electrophoresis and by mass spectrometry.

[2'-0-(2-Methoxyethyl)]-[2'-deoxy]-[2'-0-(Methoxyethyl)]Chimeric Phosphorothioate Oligonucleotides: [2'-O-(2-methoxyethyl)]-[2'-deoxy]-[-2'-O-(methoxyethyl)]chimeric phosphorothioate oligonucleotides are prepared as per the procedure above for the 2'-O-methyl chimeric oligonucleotide, with the substitution of 2'-0-(methoxyethyl)amidites for the 2'-O-methyl amidites. [2'-O-(2-Methoxyethyl)Phosphodiester]-[2'-deoxy Phosphorothioate]-[2'-O-(2-Methoxyethyl) Phosphodiester] Chimeric Oligonucleotides: [2'-O-(2-methoxyethyl phosphodiester]-[2'-deoxy phosphorothioate]-[2'-O-(methoxyethyl)phosphodiester]chimeric oligonucleotides are prepared as per the above procedure for the 2'-O-methyl chimeric oligonucleotide with the substitution of 2'-O-(methoxyethyl)amidites for the 2'-O-methyl amidites, oxidization with iodine to generate the phosphodiester internucleotide linkages within the wing portions of the chimeric structures and sulfurization using 3H-1,2 benzodithiole-3-one 1,1 dioxide (Beaucage Reagent) to generate the phosphorothioate internucleotide linkages for the center gap. Other chimeric oligonucleotides, chimeric oligonucleosides and mixed chimeric oligonucleotides/oligonucleosides are synthesized according to U.S. Pat. No. 5,623,065.

Example 13

Transgenic AMM Knockout Mouse (Prophetic Example)

Construction of Murine AMM Gene Targeting Vector

A gene targeting vector for inactivating the AMM gene is prepared using standard cloning techniques (Sambrook et al., Molecular Cloning, A Laboratory Manual, Cold Spring Harbor Laboratory Press, 1989).

For example, a targeting vector may contain from 5' to 3': 6.0 kb of 5' homology with the AMM locus; a PGKneomycin (PGKneo) expression cassette inserted in the opposite orientation to the AMM gene; and a fragment homologous to the 3' part of the AMM gene. For negative selection, a MC1-thymidine kinase (TK) gene is cloned upstream of the 5' homologous sequence for negative selection. Targeted recombination between the vector and the wild-type AMM locus will result in the deletion of part or all of the AMM gene and replaced by the neomycin resistance gene.

Targeted Disruption of the AMM Gene in Murine ES Cells

The targeting vector is linearized at a unique restriction site before electroporating into AB2.1 ES cells. The AB2.1 ES cells are cultured on SNL feeder cells and the selection of targeted AMM clones is performed by techniques known in the art. ES cell DNA (8 µg preferably) from the wild-type AB2.1 cells and the clones are digested with a diagnostic restriction enzyme and analyzed by Southern blotting, using hybridization probes homologous to a fragment downstream of the 3' homologous sequence. The restriction enzyme is chosen to distinguish between the wild-type and mutant alleles. The diagnostic fragment is detected by the probe in the targeted clones in addition to the wild-type 8.7 kb fragment.

Production of Chimeric Mice

Six AMM targeted ES clones were injected into C57BL/ 6J recipient blastocysts in separate experiments using routine techniques (Bradley, 1987). As the ES cell line AB2.1 is homozygous for the agouti (A) coat color gene, penetrance of ES cells into the injected (black coat color) C57B1/6 blastocyst will give rise to chimeric coat color mice.

Generation of Heterozygous AMM Knockout Mice and Homozygous AAM Knockout Embryos The chimeric mice are then bred to wild-type C57BL16 female mice. Agouti offspring resulting from the cross will indicate germline transmission. To determine the AMM genotypes, genomic DNA is purified from about 1 cm of tail taken from each mouse. Southern hybridization analysis is then used to confirm offspring that contain the disrupted allele. ES cell DNA from the wild-type AB2.1 cells may be used as controls.

Transgenic offspring that are heterozygous for the AMM disruption (AMM+/−) are then mated with each other to generate mice in which both copies of the AMM gene encoded the targeted, altered AMM allele (homozygous mice, or AMM−/−). Because the disruption is a single gene, simple Mendelian inheritance patterns are predicted, with one-fourth of the offspring being AMM−/−, barring embryonic lethal or penetrance effects. If the defect is embryonic lethal, mouse embryos may be assessed to confirm Mendelian frequencies, as well as the stage at which the embryos aborted.

Confirmation of AMM Inactivation by Western Blot Analysis

Immunoblot of total protein extracts (100 mg) of wild-type (+/+), heterozygous (+/−) and homozygous (−/−) AMM knockout mice (or embryos if homozygous lethal) are performed. Polyclonal rabbit anti-AMM antibodies are usually most useful for detection. Superoxide dismutase 1(SOD1) is used as an internal standard. The effect of gene dosage can then be assessed at the polypeptide level. Homozygous individuals are predicted to synthesize no AMM polypeptides. Heterozygotes may accumulate to approximately 50%–100% of the level of control littermates.

Morphologic Characterization of Homozygous AMM-Deficient Mice

Visual inspection of offspring and/or embryos is performed to assess other phenotypic variations from wild-type mice.

If embryos or adult tissues are desired to be more closely monitored for developmental effects, samples may be prepared for histology. For example, embryos are fixed in 4% paraformaldehyde for 2 hours at 27° C., dehydrated in ethanol series, embedded in paraffin and sectioned at 10 mm using a microtome. Sections are stained with either hematoxylin and eosin or Masson trichrome for histological analysis. For ultrastructural analyses, if desired, samples may be fixed in half-strength Karnovsky's fixative, followed by fixation in 1%–4% $OsO_4$ (diluted in water or suitable non-salt-precipitating buffer), dehydrated through a cold ethanol series, infiltrated with resin (using either ethanol or propylene oxide for hydrophobic resins, such as Polybed 812), polymerized, sectioned with an ultramicrotome to obtain thin sections, and then counterstained with uranium and lead before observing under a transmission electron microscope.

Those of skill in the art will appreciate that many changes and approaches can be made to create a transgenic AMM mouse. For example, the FVB strain may be used instead of C57BL16; the transgene may replace the native gene sequence with an AMM sequence operably-linked to an inducible or tissue-specific promoter, or a cre/lox design may be incorporated to control when the AMM gene is "knocked out." Finally, mice that express anti-sense to AMM (operably-linked to an inducible promoter or not) may also be created; although the site of integration for such a construct is desired to be elsewhere in the genome other than the AMM locus.

Example 14

Characterization of AMM Transgenic Mice in Fasting-feeding Experiments (Prophetic Example)

Experimental Design Details

Four groups of mice; n=5/group.
1. Ad lib feed mice.
2. Mice fasted for 4 hours.
3. Mice fasted for 24 hours and are then refed ad lib for 24 hours.
4. Mice fasted for 48 hours
5. Mice fasted for 48 hours and are then refed ad lib for 24 hours.

Mice that are 3 weeks of age are used and are housed at 2 mice/cage until tissue harvest at 6 weeks of age. All mice are fed rodent chow ad libitum (Chow 5010, Ralston Purina; St. Louis, Mo.) and housed on a 12 hour/12 hour light/dark cycle (lights on 06:00 a.m.) at 22° C.

The mice then may be assessed for a variety of characteristics, including gene expression profiling, weight gain and loss, metabolic profiles, etc.

REFERENCES

U.S. Pat. No. 4,166,452. Apparatus for testing human responses to stimuli. 1979.

U.S. Pat. No. 4,485,045. Synthetic phosphatidyl cholines useful in forming liposomes. 1984.

U.S. Pat. No. 4,544,545. Liposomes containing modified cholesterol for organ targeting. 1985.

U.S. Pat. No. 4,676,980. Target specific cross-linked heteroantibodies. 1987.

U.S. Pat. No. 4,816,567. Recombinant immunoglobin preparations. 1989.

WO 01/23430A2. Chitinase Immunoglobulin Fusion Products. 2001.

WO 90/10448. Covalent conjugates of lipid and oligonucleotide. 1990.

WO 90/13641. Stably transformed eukaryotic cells comprising a foreign transcribable DNA under the control of a pol III promoter. 1990.

EPO 402226. Transformation vectors for yeast Yarrowia. 1990.

WO 91/00360. Bispecific reagents for AIDS therapy. 1991.

WO 91/04753. Conjugates of anti-sense oligonucleotides and therapeutic uses thereof. 1991.

U.S. Pat. No. 5,013,556. Liposomes with enhanced circulation time. 1991.

WO 91/06629. Oligonucleotide analogs with novel linkages. 1991.

WO 92/20373. Heteroconjugate antibodies for treatment of HIV infection. 1992.

WO 93/08829. Compositions that mediate killing of HIV-infected cells. 1993.

WO 94/11026. Therapeutic application of chimeric and radiolabeled antibodies to human B lymphocyte restricted differentiation antigen for treatment of B cells. 1994.

WO 96/27011. A method for making heteromultimeric polypeptides. 1996.

U.S. Pat. No. 5,545,807. Production of antibodies from transgenic animals. 1996.

U.S. Pat. No. 5,569,825. Transgenic non-human animals capable of producing heterologous antibodies of various isotypes. 1996.

WO 97/33551. Compositions and methods for the diagnosis, prevention, and treatment of neoplastic cell growth and proliferation. 1997.

U.S. Pat. No. 5,633,425. Transgenic non-human animals capable of producing heterologous antibodies. 1997.

U.S. Pat. No. 5,661,016. Transgenic non-human animals capable of producing heterologous antibodies of various isotypes. 1997.

U.S. Pat. No. 5,625,126. Transgenic non-human animals for producing heterologous antibodies. 1997.

Abravaya, K., J. J. Carrino, S. Muldoon, and H. H. Lee. 1995. Detection of point mutations with a modified ligase chain reaction (Gap-LCR). *Polynucleotides Res.* 23:675–82.

Alam, J., and J. L. Cook. 1990. Reporter genes: Application to the study of mammalian gene transcription. *Anal. Biochem.* 188:245–254.

Altschul, S. F., W. Gish, W. Miller, E. W. Myers, et al. 1990. Basic local alignment search tool. *J Mol Biol.* 215:403–10.

Altschul, S. F., T. L. Madden, A. A. Schaffer, J. Zhang, et al. 1997. Gapped BLAST and PSI-BLAST: a new generation of protein database search programs. *Polynucleotides Res.* 25:3389–402.

Aron, D., J. Findling, and J. Tyrrell. 1997. Hypothalamus and pituitary. In Basic & clinical endocrinology. F. Greenspan and G. Strewler, editors. Appleton & Lange, Stamford. 95–156.

Austin, C. P., and C. L. Cepko. 1990. Cellular migration patterns in the developing mouse cerebral cortex. *Development.* 110:713–732.

Ausubel, F. M., R. Brent, R. E. Kingston, D. D. Moore, et al. 1987. Current protocols in molecular biology. John Wiley & Sons, New York.

Barany, F. 1991. Genetic disease detection and DNA amplification using cloned thermostable ligase. *Proc Natl Acad Sci USA.* 88:189–93.

Bartel, D. P., and J. W. Szostak. 1993. Isolation of new ribozymes from a large pool of random sequences [see comment]. *Science.* 261:1411–8.

Bartel, P., C. T. Chien, R. Sternglanz, and S. Fields. 1993. Elimination of false positives that arise in using the two-hybrid system. *Biotechniques.* 14:920–4.

Beal, P. A., and P. B. Dervan. 1991. Second structural motif for recognition of DNA by oligonucleotide-directed triple-helix formation. *Science.* 251:1360–3.

Bechtold, N., and G. Pelletier. 1998. In planta Agrobacterium-mediated transformation of adult *Arabidopsis thaliana* plants by vacuum infiltration. *Methods Mol Biol.* 82:259–66.

Beck, B. 2001. KO's and organization of peptidergic feeding behavior mechanisms. *Neurosci Biobehav Rev.* 25:143–58.

Becker, D. M., and L. Guarente. 1991. High-efficiency transformation of yeast by electroporation. *Methods Enzymol.* 194:182–187.

Beggs, J. D. 1978. Transformation of yeast by a replicating hybrid plasmid. *Nature.* 275:104–109.

Berger, J., J. Hauber, R. Hauber, R. Geiger, et al. 1988. Secreted placental alkaline phosphatase: A powerful new quantitative indicator of gene expression in eukaryotic cells. *Gene.* 66:1–10.

Berns, A., R. Mandag, and H. Te Riele. WO 93/04169. GENE TARGETING IN ANIMAL CELLS USING ISOGENIC DNA CONSTRUCTS. 1993.

Bodine, D. M., K. T. McDonagh, N. E. Seidel, and A. W. Nienhuis. 1991. Survival and retrovirus infection of murine hematopoietic stem cells in vitro: effects of 5-FU and method of infection. *Exp. Hematol.* 19:206–212.

Boerner, P., R. Lafond, W. Z. Lu, P. Brams, et al. 1991. Production of antigen-specific human monoclonal antibodies from in vitro-primed human splenocytes. *J Immunol.* 147:86–95.

Bolivar, F., Rodriguez, R. L., Greene, P. J., Betlach, M. C., Heyneker, H. L. and Boyer, H. W. (1977) Construction and characterization of new cloning vehicles. II. A multipurpose cloning system. *Gene* 2, 95–113.

Boot, R. G., Renkema, G. H., Strijland, A., van Zonneveld, A. J. and Aerts, J. M. (1995) Cloning of a cDNA encoding chitotriosidase, a human chitinase produced by macrophages. *J Biol Chem* 270, 26252–26256.

Boot, R. G., E. F. C. Blommaart, E. Swart, K. Ghauharali-van der Vlugt, N. Bijl, C. Moe, A. Place, and J. M. F. G. Aerts. 2001. Identification of a Novel Acidic Mammalian Chitinase Distinct from Chitotriosidase. *J. Biol. Chem.* 276(9):6770–6778.

Boswell, G. A., and R. M. Scribner. U.S. Pat. No. 3,773,919. Polylactide-drug mixtures. 1973.

Bradley. 1987. Teratocarcinomas and Embryonic Stem Cells: A Practical Approach. Oxford University Press, Inc., Oxford. 268 pp.

Bradley, A. 1991. Modifying the mammalian genome by gene targeting. *Curr Opin Biotechnol.* 2:823–9.

Brennan, M., P. F. Davison, and H. Paulus. 1985. Preparation of bispecific antibodies by chemical recombination of monoclonal immunoglobulin G1 fragments. *Science.* 229:81–3.

Brent, R., J. Gyunris, and E. Golemis. WO94/10300. INTERACTION TRAP SYSTEM FOR ISOLATING NOVEL PROTEINS. 1994.

Cancela, J. M. 2001. Specific Ca2+ signaling evoked by cholecystokinin and acetylcholine: the roles of NAADP, cADPR, and IP3. *Annu Rev Physiol.* 63:99–117.

Capecchi, M. R. 1980. High efficiency transformation by direct microinjection of DNA into cultured mammalian cells. *Cell.* 22:479.

Capecchi, M. R. 1989. Altering the genome by homologous recombination. *Science.* 244:1288–92.

Carell, T., E. A. Wintner, and J. Rebek Jr. 1994a. A novel procedure for the synthesis of libraries containing small organic molecules. *Angewandte Chemie International Edition.* 33:2059–2061.

Carell, T., E. A. Wintner, and J. Rebek Jr. 1994b. A solution phase screening procedure for the isolation of active compounds from a molecular library. *Angewandte Chemie International Edition.* 33:2061–2064.

Caron, P.C., W. Laird, M. S. Co, N.M. Avdalovic, et al. 1992. Engineered humanized dimeric forms of IgG are more effective antibodies. *J Exp Med.* 176:1191–5.

Carter, P. 1986. Site-directed mutagenesis. *Biochem J.* 237:1–7.

Case, M. E., M. Schweizer, S. R. Kushner, and N. H. Giles. 1979. Efficient transformation of Neurospora crassa by utilizing hybrid plasmid DNA. *Proc Natl Acad Sci USA.* 76:5259–63.

Cech, T. R., F. L. Murphy, and A. J. Zaug. U.S. Pat. No. 5,116,742. RNA ribozyme restriction endoribonucleases and methods. 1992.

Cech, T. R., A. J. Zaug, and M. D. Been. U.S. Pat. No. 4,987,071. RNA ribozyme polymerases, dephosphorylases, restriction endoribonucleases and methods. 1991.

Cepko, C. L., B. E. Roberts, and R. E. Mulligan. 1984. Construction and applications of a highly transmissible murine retrovirus shuttle vector. *Cell.* 37:1053–1062.

Chalfie, M., Y. tu, G. Euskirchen, W. W. Ward, et al. 1994. Green fluorescent protein as a marker for gene expression. *Science.* 263:802–805.

Chaney, W. G., D. R. Howard, J. W. Pollard, S. Sallustio, et al. 1986. High-frequency transfection of CHO cells using Polybrene. *Somatic Cell Mol Genet.* 12:237.

Chen, C., and H. Okayama. 1988. Calcium phosphate-mediated gene transfer: A highly efficient system for stably transforming cells with plasmid DNA. *BioTechniques.* 6:632–638.

Chen, S. H., H. D. Shine, J. C. Goodman, R. G. Grossman, et al. 1994. Gene therapy for brain tumors: regression of experimental gliomas by adenovirus-mediated gene transfer in vivo. *Proc Natl Acad Sci USA.* 91:3054–7.

Cho, C. Y., E. J. Moran, S. R. Cherry, J. C. Stephans, et al. 1993. An unnatural biopolymer. *Science.* 261:1303–5.

Clement, K., C. Vaisse, N. Lahlou, S. Cabrol, et al. 1998. A mutation in the human leptin receptor gene causes obesity and pituitary dysfunction. *Nature.* 392:398–401.

Cohen, A. S., D. L. Smisek, and B. H. Wang. 1996. Emerging technologies for sequencing anti-sense oligonucleotides: capillary electrophoresis and mass spectrometry. *Adv Chromatogr.* 36:127–62.

Cohen, J. S. 1989. Oligodeoxynucleotides: Anti-sense inhibitors of gene expression. CRC Press, Boca Raton, Fla. 255 pp.

Cohen, S. M. N., A. C. Y. Chang, and L. Hsu. 1972. Nonchromosomal antibiotic resistance in bacteria: Genetic transformation of *Escherichia coli* by R-factor DNA. Proc. Natl. Acad. Sci. USA. 69:2110.

Comuzzie, A. G., and D. B. Allison. 1998. The search for human obesity genes. *Science.* 280:1374–7.

Cooney, M., G. Czernuszewicz, E. H. Postel, S. J. Flint, et al. 1988. Site-specific oligonucleotide binding represses transcription of the human c-myc gene in vitro. *Science.* 241:456–9.

Cotton, R. G. 1993. Current methods of mutation detection. Mutat Res. 285:125–44.

Cronin, M. T., R. V. Fucini, S. M. Kim, R. S. Masino, et al. 1996. Cystic fibrosis mutation detection by hybridization to light-generated DNA probe arrays. *Hum Mutat.* 7:244–55.

Cull, M. G., J. F. Miller, and P. J. Schatz. 1992. Screening for receptor ligands using large libraries of peptides linked to the C terminus of the lac repressor. *Proc Natl Acad Sci USA.* 89:1865–9.

Cwirla, S. E., E. A. Peters, R. W. Barrett, and W. J. Dower. 1990. Peptides on phage: a vast library of peptides for identifying ligands. *Proc Natl Acad Sci USA.* 87:6378–82.

de Boer, A. G. 1994. Drug absorption enhancement: Concepts, possibilities, limitations and trends. Harwood Academic Publishers, Langhorne, Pa.

de Louvencourt, L., H. Fukuhara, H. Heslot, and M. Wesolowski. 1983. Transformation of Kluyveromyces lactis by killer plasmid DNA. *J Bacteriol.* 154:737–42.

de Wet, J. R., K. V. Wood, M. DeLuca, D. R. Helinski, et al. 1987. Structure and expression in mammalian cells. *Mol. Cell Biol.* 7:725–737.

Demerec, M., E. A. Adelberg, A. J. Clark, and P. E. Hartman. 1966. A proposal for a uniform nomenclature in bacterial genetics. *Genetics.* 54:61–76.

Devlin, J. J., L. C. Panganiban, and P. E. Devlin. 1990. Random peptide libraries: a source of specific protein binding molecules. Science. 249:404–6.

DeWitt, S. H., J. S. Kiely, C. J. Stankovic, M. C. Schroeder, et al. 1993. "Diversomers": an approach to nonpeptide, nonoligomeric chemical diversity. *Proc Natl Acad Sci USA.* 90:6909–13.

Ebihara, K., Y. Ogawa, H. Masuzaki, M. Shintani, et al. 2001. Transgenic overexpression of leptin rescues insulin resistance and diabetes in a mouse model of lipoatrophic diabetes. *Diabetes.* 50:1440–8.

Eichelbaum, M., and B. Evert. 1996. Influence of pharmacogenetics on drug disposition and response. *Clin Exp Pharmacol Physiol.* 23:983–5.

Ellington, A. D., and J. W. Szostak. 1990. In vitro selection of RNA molecules that bind specific ligands. *Nature.* 346:818–22.

Elroy-Stein, O., and B. Moss. 1990. Cytoplasmic expression system based on constitutive synthesis of bacteriophage T7 RNA polymerase in mammalian cells. *Proc. Natl. Acad. Sci. USA.* 87:6743–6747.

EP 307,247

Eppstein, D. A., E. B. Fraser-Smith, and T. R. Mattews. U.S. Pat. No. 4,522,811. Serial injection of muramyldipeptides and liposomes enhances the anti-infective activity of muramyldipeptides Serial injection of muramyldipeptides and liposomes enhances the anti-infective activity of muramyldipeptides. 1985.

Eppstein, D. A., Y. V. Marsh, M. van der Pas, P. L. Felgner, et al. 1985. Biological activity of liposome-encapsulated murine interferon gamma is mediated by a cell membrane receptor. *Proc Natl Acad Sci USA.* 82:3688–92.

Escudero, J., and B. Hohn. 1997. Transfer and integration of T-DNA without cell injury in the host plant. *Plant Cell.* 9:2135–2142.

Evans, R., R. D. Palmiter, and R. L. Brinster. U.S. Pat. No. 4,870,009. Method of obtaining gene product through the generation of transgenic animals. 1989.

Farooqi, I. S., S. A. Jebb, G. Langmack, E. Lawrence, et al. 1999. Effects of recombinant leptin therapy in a child with congenital leptin deficiency. *N Engl J. Med.* 341:879–84.

Fekete, D. M., and C. L. Cepko. 1993. Retroviral infection coupled with tissue transplantation limits gene transfer in the chick embryo. *Proc. Natl. Acad. Sci. USA.* 90:2350–2354.

Felgner, P. L., T. R. Gadek, M. Holm, R. Roman, et al. 1987. Lipofectin: A highly efficient, lipid-mediated DNA/transfection procedure. *Proc. Natl. Acad. Sci. USA.* 84:7413–7417.

Felici, F., L. Castagnoli, A. Musacchio, R. Jappelli, et al. 1991. Selection of antibody ligands from a large library of oligopeptides expressed on a multivalent exposition vector. *J Mol Biol.* 222:301–10.

Fieck, A., D. L. Wyborski, and J. M. Short. 1992. Modifications of the *E. coli* Lac repressor for expression in eukaryotic cells: effects of nuclear signal sequences on protein activity and nuclear accumulation. *Polynucleotides Res.* 20:1785–91.

Finer, J. J., K. R. Finer, and T. Ponappa. 1999. Particle bombardment-mediated transformation. *Current Topics in microbiology and immunology.* 240:59–80.

Finn, P. J., N. J. Gibson, R. Fallon, A. Hamilton, et al. 1996. Synthesis and properties of DNA-PNA chimeric oligomers. *Polynucleotides Res.* 24:3357–63.

Fishwild, D. M., S. L. O'Donnell, T. Bengoechea, D. V. Hudson, et al. 1996. High-avidity human IgG kappa monoclonal antibodies from a novel strain of minilocus transgenic mice [see comments]. *Nat Biotechnol.* 14:845–51.

Fleer, R., P. Yeh, N. Amellal, I. Maury, et al. 1991. Stable multicopy vectors for high-level secretion of recombinant human serum albumin by Kluyveromyces yeasts. *Biotechnology (N Y).* 9:968–75.

Fodor, S. P., R. P. Rava, X. C. Huang, A. C. Pease, et al. 1993. Multiplexed biochemical assays with biological chips. *Nature.* 364:555–6.

Fromm, M., L. P. Taylor, and V. Walbot. 1985. Expression of genes transferred into monocot and dicot plant cells by electroporation. *Proc. Natl. Acad. Sci. USA.* 82:5824–5828.

Fujiki, Y. 2000. Peroxisome biogenesis and peroxisome biogenesis disorders. *FEBS Lett.* 476:42–6.

Fujita, T., H. Shubiya, T. Ohashi, K. Yamanishi, et al. 1986. Regulation of human interleukin-2 gene: Functional DNA sequences in the 5' flanking region for the gene expression in activated T lymphocytes. *Cell.* 46:401–407.

Gabizon, A., R. Shiota, and D. Papahadjopoulos. 1989. Pharmacokinetics and tissue distribution of doxorubicin encapsulated in stable liposomes with long circulation times. *J Natl Cancer Inst.* 81:1484–8.

Gallagher, S. R. 1992. GUS protocols: Using the GUS gene as a reporter of gene expression. Academic Press, San Diego, Calif.

Gallop, M. A., R. W. Barrett, W. J. Dower, S. P. Fodor, et al. 1994. Applications of combinatorial technologies to drug discovery. 1. Background and peptide combinatorial libraries. *J Med Chem.* 37:1233–51.

Gasparini, P., A. Bonizzato, M. Dognini, and P. F. Pignatti. 1992. Restriction site generating-polymerase chain reaction (RG-PCR) for the probeless detection of hidden genetic variation: application to the study of some common cystic fibrosis mutations. *Mol Cell Probes.* 6:1–7.

Gautier, C., F. Morvan, B. Rayner, T. Huynh-Dinh, et al. 1987. Alpha-DNA. IV: Alpha-anomeric and beta-anomeric tetrathymidylates covalently linked to intercalating oxazolopyridocarbazole. Synthesis, physicochemical properties and poly (rA) binding. *Polynucleotides Res.* 15:6625–41.

Gennaro, A. R. 2000. Remington: The science and practice of pharmacy. Lippincott, Williams & Wilkins, Philadelphia, Pa.

Gibbs, R. A., P. N. Nguyen, and C. T. Caskey. 1989. Detection of single DNA base differences by competitive oligonucleotide priming. *Polynucleotides Res.* 17:2437–48.

Gietz, R. D., R. A. Woods, P. Manivasakam, and R. H. Schiestl. 1998. Growth and transformation of *Saccharomyces cerevisiae*. In Cells: A laboratory manual. Vol. I. D. Spector, R. Goldman, and L. Leinwand, editors. Cold Spring Harbor Press, Cold Spring Harbor, N.Y.

Giraldo, P., Cenarro, A., Alfonso, P., Perez-Calvo, J. I., Rubio-Felix, D., Giralt, M. and Pocovi, M. (2001) Chitotriosidase genotype and plasma activity in patients type 1 Gaucher's disease and their relatives (carriers and non carriers). *Haematologica* 86, 977–984.

Goding, J. W. 1996. Monoclonal antibodies: Principles and Practice. Academic Press, San Diego. 492 pp.

Gorman, C. M., L. F. Moffat, and B. H. Howard. 1982. Recombinant genomes which express chloramphenicol acetyltransferase in mammalian cells. *Mol. Cell. Biol.* 2:1044–1051.

Graham, F. L., and A. J. van der Eb. 1973. A new technique for the assay of infectivity of human adenovirus 5 DNA. *Virology.* 52:456-.

Griffin, H. G., and A. M. Griffin. 1993. DNA sequencing. Recent innovations and future trends. *Appl Biochem Biotechnol.* 38:147–59.

Grompe, M., D. M. Muzny, and C. T. Caskey. 1989. Scanning detection of mutations in human ornithine transcarbamoylase by chemical mismatch cleavage. *Proc Natl Acad Sci USA.* 86:5888–92.

Gruber, M., B. A. Schodin, E. R. Wilson, and D. M. Kranz. 1994. Efficient tumor cell lysis mediated by a bispecific single chain antibody expressed in *Escherichia coli*. *J Immunol.* 152:5368–74.

Guan, X. M., H. Yu, and L. H. Van der Ploeg. 1998. Evidence of altered hypothalamic pro-opiomelanocortin/neuropeptide Y mRNA expression in tubby mice. *Brain Res Mol Brain Res.* 59:273–9.

Guatelli, J. C., K. M. Whitfield, D. Y. Kwoh, K. J. Barringer, et al. 1990. Isothermal, in vitro amplification of polynucleotides by a multienzyme reaction modeled after retroviral replication. *Proc Natl Acad Sci USA.* 87:1874–8.

Hanahan, D. 1983. Studies on transformation of *Escherichia coli* with plasmids. *J. Mol. Biol.* 166:557–580.

Hansen, G., and M.-D. Chilton. 1999. Lessons in gene transfer to plants by a gifted microbe. *Curr. Top. Microbiol. Immunol.* 240:21–57.

Hansen, G., and M. S. Wright. 1999. Recent advances in the transformation of plants. *Trends Plant Sci.* 4:226–231.

Harlow, E., and D. Lane. 1988. Antibodies: A laboratory manual. Cold Spring Harbor Laboratory Press, Cold Spring Harbor. 726 pp.

Harlow, E., and D. Lane. 1999. Using antibodies: A laboratory manual. Cold Spring Harbor Laboratory PRess, Cold Spring Harbor, N.Y.

Haseloff, J., and W. L. Gerlach. 1988. Simple RNA enzymes with new and highly specific endoribonuclease activities. *Nature.* 334:585–91.

Hayashi, K. 1992. PCR-SSCP: A method for detection of mutations. *Genetic and Analytical Techniques Applications.* 9:73–79.

Helene, C. 1991. The anti-gene strategy: control of gene expression by triplex-forming-oligonucleotides. *Anticancer Drug Des.* 6:569–84.

Helene, C., N. T. Thuong, and A. Harel-Bellan. 1992. Control of gene expression by triple helix-forming oligonucleotides. The antigene strategy. *Ann NY Acad Sci.* 660:27–36.

Heymsfield, S. B., A. S. Greenberg, K. Fujioka, R. M. Dixon, et al. 1999. Recombinant leptin for weight loss in obese and lean adults: a randomized, controlled, dose-escalation trial. *Jama.* 282:1568–75.

Hill, J. O., and J. C. Peters. 1998. Environmental contributions to the obesity epidemic. *Science.* 280:1371–4.

Hinnen, A., J. B. Hicks, and G. R. Fink. 1978. Transformation of yeast. *Proc. Natl. Acad. Sci. USA.* 75:1929–1933.

Hoffman, F. 1996. Laser microbeams for the manipulation of plant cells and subcellular structures. *Plant Sci.* 113:1–11.

Hogan, B., Beddington, R., Costantini, F., Lacy, E. 1994. Manipulating the Mouse Embryo: A Laboratory Manual. Cold Spring Harbor Laboratory Press. 500 pp.

Hollak, C. E., van Weely, S., van Oers, M. H. and Aerts, J. M. (1994) Marked elevation of plasma chitotriosidase activity. A novel hallmark of Gaucher disease. *J Clin Invest* 93, 1288–1292.

Holliger, P., T. Prospero, and G. Winter. 1993. "Diabodies": small bivalent and bispecific antibody fragments. *Proc Natl Acad Sci USA.* 90:6444–8.

Hoogenboom, H. R., A. D. Griffiths, K. S. Johnson, D. J. Chiswell, et al. 1991. Multi-subunit proteins on the surface of filamentous phage: methodologies for displaying antibody (Fab) heavy and light chains. *Polynucleotides Res.* 19:4133–7.

Houghten, R. A., J. R. Appel, S. E. Blondelle, J. H. Cuervo, et al. 1992. The use of synthetic peptide combinatorial libraries for the identification of bioactive peptides. *Biotechniques.* 13:412–21.

Hsu, I. C., Q. Yang, M. W. Kahng, and J. F. Xu. 1994. Detection of DNA point mutations with DNA mismatch repair enzymes. *Carcinogenesis.* 15:1657–62.

Hwang, K. J., K. F. Luk, and P. L. Beaumier. 1980. Hepatic uptake and degradation of unilamellar sphingomyelin/cholesterol liposomes: a kinetic study. *Proc Natl Acad Sci USA.* 77:4030–4.

Hyrup, B., and P. E. Nielsen. 1996. Peptide polynucleotides (PNA): synthesis, properties and potential applications. *Bioorg Med Chem.* 4:5–23.

Infante, J. P., and V. A. Huszagh. 2001. Zellweger syndrome knockout mouse models challenge putative peroxisomal beta-oxidation involvement in docosahexaenoic acid (22:6n-3) biosynthesis. *Mol Genet Metab.* 72:1–7.

Inoue, H., Y. Hayase, A. Imura, S. Iwai, et al. 1987a. Synthesis and hybridization studies on two complementary nona(2'-O-methyl)ribonucleotides. *Polynucleotides Res.* 15:6131–48.

Inoue, H., Y. Hayase, S. Iwai, and E. Ohtsuka. 1987b. Sequence-dependent hydrolysis of RNA using modified oligonucleotide splints and RNase H. *FEBS Lett.* 215:327–30.

Ishiura, M., S. Hirose, T. Uchida, Y. Hamada, et al. 1982. Phage particle-mediated gene transfer to cultured mammalian cells. *Molecular and Cellular Biology.* 2:607–616.

Ito, H., Y. Fukuda, K. Murata, and A. Kimura. 1983. Transformation of intact yeast cells treated with alkali cations. *J Bacteriol.* 153:163–168.

Iwabuchi, K., B. Li, P. Bartel, and S. Fields. 1993. Use of the two-hybrid system to identify the domain of p53 involved in oligomerization. *Oncogene.* 8:1693–6.

Jayasena, S. D. 1999. Aptamers: an emerging class of molecules that rival antibodies in diagnostics. *Clin Chem.* 45:1628–50.

Jones, P. T., P. H. Dear, J. Foote, M. S. Neuberger, et al. 1986. Replacing the complementarity-determining regions in a human antibody with those from a mouse. *Nature.* 321:522–5.

Kaufman, R. J. 1990. Vectors used for expression in mammalian cells. *Methods Enzymol.* 185:487–511.

Kaufman, R. J., P. Murtha, D. E. Ingolia, C.-Y. Yeung, et al. 1986. Selection and amplification of heterologous genes encoding adenosine deaminase in mammalian cells. *Proc. Natl. Acad. Sci. USA.* 83:3136–3140.

Kawai, S., and M. Nishizawa. 1984. New procedure for DNA transfection with polycation and dimethyl sulfoxide. *Mol. Cell. Biol.* 4:1172.

Keen, J., D. Lester, C. Inglehearn, A. Curtis, et al. 1991. Rapid detection of single base mismatches as heteroduplexes on Hydrolink gels. *Trends Genet.* 7:5.

Kelly, J. M., and M. J. Hynes. 1985. Transformation of *Aspergillus niger* by the amdS gene of *Aspergillus nidulans. Embo J.* 4:475–9.

Kersten, S. 2001. Mechanisms of nutritional and hormonal regulation of lipogenesis. *EMBO Rep.* 2:282–6.

Kostelny, S. A., M. S. Cole, and J. Y. Tso. 1992. Formation of a bispecific antibody by the use of leucine zippers. *J Immunol.* 148:1547–53.

Koster, H. WO94/16101. DNA SEQUENCING BY MASS SPECTROMETRY. 1994.

Kozal, M. J., N. Shah, N. Shen, R. Yang, et al. 1996. Extensive polymorphisms observed in HIV-1 clade B protease gene using high-density oligonucleotide arrays. *Nat Med.* 2:753–9.

Kozbor, D., P. Tripputi, J. C. Roder, and C. M. Croce. 1984. A human hybrid myeloma for production of human monoclonal antibodies. *J Immunol.* 133:3001–5.

Kriegler, M. 1990. Gene transfer and expression: A laboratory manual. Stockton Press, New York. 242 pp.

Kucherlapati, R. S., B. H. Koller, and 0. Smithies. WO 91/01140. HOMOLOGOUS RECOMBINATION FOR UNIVERSAL DONOR CELLS AND CHIMERIC MAMMALIAN HOSTS. 1991.

Kwoh, D. Y., G. R. Davis, K. M. Whitfield, H. L. Chappelle, et al. 1989. Transcription-based amplification system and detection of amplified human immunodeficiency virus type 1 with a bead-based sandwich hybridization format. *Proc Natl Acad Sci USA.* 86:1173–7.

Ladner, R. C., S. K. Guterman, B. L. Roberts, W. Markland, et al. U.S. Pat. No. 5,223,409. Directed evolution of novel binding proteins. 1993.

Lakso, M., B. Sauer, B. Mosinger, E. J. Lee, et al. 1992. Targeted oncogene activation by site-specific recombination in transgenic mice. *Proc Natl Acad Sci USA.* 89:6232–6.

Lam, K. S. 1997. Application of combinatorial library methods in cancer research and drug discovery. *Anticancer Drug Design.* 12:145–167.

Lam, K. S., S. E. Salmon, E. M. Hersh, V. J. Hruby, et al. 1991. General method for rapid synthesis of multicomponent peptide mixtures. *Nature.* 354:82–84.

Landegren, U., R. Kaiser, J. Sanders, and L. Hood. 1988. A ligase-mediated gene detection technique. *Science.* 241:1077–80.

Le Mouellic, H., and P. Brullet. WO 90/11354. Process for the specific replacement of a copy of a gene present in the receiver genome via the integration of a gene. 1990.

Leder, P., and T. A. Stewart. U.S. Pat. No. 4,736,866. Transgenic non-human animals. 1988.

Leduc, N., and e. al. 1996. Isolated maize zygotes mimic in vivo embryogenic development and express microinjected genes when cultured in vitro. *Dev. Biol.* 10:190–203.

Lee, J. S., D. A. Johnson, and A. R. Morgan. 1979. Complexes formed by (pyrimidine)n. (purine)$_n$ DNAs on lowering the pH are three-stranded. *Polynucleotides Res.* 6:3073–91.

Lee, V. H. L. 1990. Peptide and protein drug delivery. Marcel Dekker, New York, N.Y.

Lefebvre, O., M. P. Chenard, R. Masson, J. Linares, et al. 1996. Gastric mucosa abnormalities and tumorigenesis in mice lacking the pS2 trefoil protein. *Science.* 274:259–62.

Lemaitre, M., B. Bayard, and B. Lebleu. 1987. Specific antiviral activity of a poly(L-lysine)-conjugated oligodeoxyribonucleotide sequence complementary to vesicular stomatitis virus N protein mRNA initiation site. *Proc Natl Acad Sci USA.* 84:648–52.

Lemischka, I. R., D. H. Raulet, and R. C. Mulligan. 1986. Developmental potential and dynamic behavior of hematopoietic stem cells. *Cell.* 45:917–927.

Letsinger, R. L., G. R. Zhang, D. K. Sun, T. Ikeuchi, et al. 1989. Cholesteryl-conjugated oligonucleotides: synthesis, properties, and activity as inhibitors of replication of human immunodeficiency virus in cell culture. *Proc Natl Acad Sci USA.* 86:6553–6.

Li, E., T. H. Bestor, and R. Jaenisch. 1992. Targeted mutation of the DNA methyltransferase gene results in embryonic lethality. *Cell.* 69:915–26.

Linder, M. W., R. A. Prough, and R. Valdes. 1997. Pharmacogenetics: a laboratory tool for optimizing therapeutic efficiency. *Clin Chem.* 43:254–66.

Littlefield, J. W. 1964. Selection of hybrids from matings of fibroblasts in vitro and their presumed recombinants. *Science.* 145:709–710.

Lizardi, P. M., C. E. Guerra, H. Lomeli, I. Tussie-Luna, et al. 1988. Exponential amplification of recombinant-RNA hybridization probes. *Biotechnology.* 6:1197–1202.

Lonberg, N., and D. Huszar. 1995. Human antibodies from transgenic mice. *Int Rev Immunol.* 13:65–93.

Lonberg, N., L. D. Taylor, F. A. Harding, M. Trounstine, et al. 1994. Antigen-specific human antibodies from mice comprising four distinct genetic modifications [see comments]. *Nature.* 368:856–9.

Lopata, M. A., D. W. Cleveland, and B. Sollner-Webb. 1984. High-level expression of a chloramphenicol acetyltransferase gene by DEAEdextran-mediated DNA transfection coupled with a dimethylsulfoxide or glycerol shock treatment. *Polynucleotides Research.* 12:5707.

Luckow, V. A. 1991. Cloning and expression of heterologous genes in insect cells with baculovirus vectors. In Recombinant DNA technology and applications. A. Prokop, R. K. Bajpai, and C. Ho, editors. McGraw-Hill, New York. 97–152.

Madura, K., R. J. Dohmen, and A. Varshavsky. 1993. N-recognin/Ubc2 interactions in the N-end rule pathway. *J Biol Chem.* 268:12046–54.

Maher, L. J. 1992. DNA triple-helix formation: an approach to artificial gene repressors? *Bioessays.* 14:807–15.

Mandel, M., and A. Higa. 1970. Calcium-dependent bacteriophage DNA infection. *J. Mol. biol.* 53:159–162.

Marasco, W. A., W. A. Haseltine, and S. Y. Chen. 1993. Design, intracellular expression, and activity of a human anti-human immunodeficiency virus type 1 gp120 single-chain antibody. *Proc Natl Acad Sci USA.* 90:7889–93.

Marks, J. D., A. D. Griffiths, M. Malmqvist, T. P. Clackson, et al. 1992. By-passing immunization: building high affinity human antibodies by chain shuffling. *Biotechnology (NY).* 10:779–83.

Marks, J. D., H. R. Hoogenboom, T. P. Bonnert, J. McCafferty, et al. 1991. By-passing immunization. Human antibodies from V-gene libraries displayed on phage. *J. Mol. Biol.* 222:581–97.

Martin, F. J., and D. Papahadjopoulos. 1982. Irreversible coupling of immunoglobulin fragments to preformed vesicles. An improved method for liposome targeting. *J Biol. Chem.* 257:286–8.

Maxam, A. M., and W. Gilbert. 1977. A new method for sequencing DNA. *Proc Natl Acad Sci USA.* 74:560–4.

Miller, A. D., and C. Buttimore. 1986. Redesign of retrovirus packaging cell lines to avoid recombination leading to helper virus production. *Mol. Cell biol.* 6:2895–2902.

Miller, L. K. 1988. Baculoviruses as gene expression vectors. *Annu. Rev. Microbiol.* 42:177–199.

Milstein, C., and A. C. Cuello. 1983. Hybrid hybridomas and their use in immunohistochemistry. *Nature.* 305:537–40.

Modrich, P., S.-S. Su, K. G. Au, and R. S. Lahue. U.S. Pat. No. 5,459,039. Methods for mapping genetic mutations. 1995.

Montague, C. T., I. S. Farooqi, J. P. Whitehead, M. A. Soos, et al. 1997. Congenital leptin deficiency is associated with severe early-onset obesity in humans. *Nature.* 387:903–8.

Morrison, S. L., L. Wims, S. Wallick, L. Tan, et al. 1987. Genetically engineered antibody molecules and their application. *Ann NY Acad Sci.* 507:187–98.

Mullis, K. B. U.S. Pat. No. 4,683,202. Process for amplifying polynucleotide sequences. 1987.

Mullis, K. B., H. A. Erlish, N. Arnheim, G. T. Horn, et al. U.S. Pat. No. 4,683,195. Process for amplifying, detecting, and/or cloning polynucleotide sequences. 1987.

Munson, P. J., and D. Rodbard. 1980. Ligand: a versatile computerized approach for characterization of ligand-binding systems. *Anal Biochem.* 107:220–39.

Myers, R. M., Z. Larin, and T. Maniatis. 1985. Detection of single base substitutions by ribonuclease cleavage at mismatches in RNA:DNA duplexes. *Science.* 230:1242–6.

Nabel, E. G., and G. J. Nabel. U.S. Pat. No. 5,328,470. Treatment of diseases by site-specific, instillation of cells or site-specific transformation of cells and kits therefore. 1994.

Naeve, C. W., G. A. Buck, R. L. Niece, R. T. Pon, et al. 1995. Accuracy of automated DNA sequencing: a multi-laboratory comparison of sequencing results. *Biotechniques.* 19:448–53.

Nakai, K., and P. Horton. 1999. PSORT: a program for detecting sorting signals in proteins and predicting their subcellular localization. *Trends Biochem Sci.* 24:34–6.

Nakazato, M., N. Murakami, Y. Date, M. Kojima, et al. 2001. A role for ghrelin in the central regulation of feeding. *Nature.* 409:194–8.

Nakazawa, H., D. English, P. L. Randell, K. Nakazawa, et al. 1994. UV and skin cancer: specific p53 gene mutation in normal skin as a biologically relevant exposure measurement. *Proc Natl Acad Sci USA.* 91:360–4.

Neumann, E., M. Schaefer-Ridder, Y. Wang, and P. H. Hofschneider. 1982. Gene transfer into mouse lyoma cells by electroporation in high electric fields. *EMBO J.* 1:841–845.

Norman, R. A., C. Bogardus, and E. Ravussin. 1995. Linkage between obesity and a marker near the tumor necrosis factor-alpha locus in Pima Indians. *J Clin Invest.* 96:158–62.

O'Gorman, S., D. T. Fox, and G. M. Wahl. 1991. Recombinase-mediated gene activation and site-specific integration in mammalian cells. *Science.* 251:1351–5.

Okano, H., J. Aruga, T. Nakagawa, C. Shiota, et al. 1991. Myelin basic protein gene and the function of anti-sense RNA in its repression in myelin-deficient mutant mouse. *J Neurochem.* 56:560–7.

O'Reilly, D. R., L. K. Miller, and V. A. Luckow. 1992. Baculovirus expression vectors. W. H. Freeman and Company, New York.

O'Reilly, D. R. (1994) *Baculovirus expression vectors: a laboratory manual*/David R. O'Reilly, Lois K. Miller, Verne A. Luckow. New York: Oxford University Press.

Orita, M., H. Iwahana, H. Kanazawa, K. Hayashi, et al. 1989. Detection of polymorphisms of human DNA by gel electrophoresis as single-strand conformation polymorphisms. *Proc Natl Acad Sci USA.* 86:2766–70.

Ou-Lee, T. M., R. Turgeon, and R. Wu. 1986. Uptake and expression of a foreign gene linked to either a plant virus or Drosophila promoter in protoplasts of rice, wheat and sorghum. *Proc. Natl. Acad. Sci. USA.* 83:6815–6819.

Owhashi, M., H. Arita, and N. Hayai. 2000. Identification of a Novel Eosinophil Chemotactic Cytokine (ECF-L) as a Chitinase Family Protein. *J. Biol. Chem.* 275(2):1279–1286.

Palmer, T. D., R. A. Hock, W. R. A. Osborne, and A. D. Miller. 1987. Efficient retrovirus-mediated transfer and expression of a human adenosine deaminase gene in diploid skin fibroblasts from an adenosine-deficient human. *Proc. Natl. Acad. Sci. USA.* 84:1055–1059.

Pardridge, W., and P. Schimmel. WO89/10134. Chimeric peptides for neuropeptide delivery through the blood-brain barrier. 1989.

Pear, W., G. Nolan, M. Scott, and D. Baltimore. 1993. Production of high-titer helper-free retroviruses by transient transfection. *Proc. Natl. Acad. Sci. USA.* 90:8392–8396.

Perry-O'Keefe, H., X. W. Yao, J. M. Coull, M. Fuchs, et al. 1996. Peptide polynucleotide pre-gel hybridization: an alternative to southern hybridization. *Proc Natl Acad Sci USA.* 93:14670–5.

Perusse, L., and C. Bouchard. 1999. Role of genetic factors in childhood obesity and in susceptibility to dietary variations. *Ann Med.* 31 Suppl 1:19–25.

Petersen, K. H., D. K. Jensen, M. Egholm, O. Buchardt, et al 1976. A PNA-DNA linker synthesis of N-((4,4'-dimethoxytrityloxy)ethyl)-N-(thymin-1-ylacetyl)glycine. *Biorganic and Medicinal Chemistry Letters.* 5:1119–1124.

Phillips, M. S., Q. Liu, H. A. Hammond, V. Dugan, et al. 1996. Leptin receptor missense mutation in the fatty Zucker rat. *Nat Genet.* 13:18–9.

Pi-Sunjer, F. C., and E. NHLBI Obesity Education Initiative Expert Panel on the Identification, and Treatment of Overweight and Obesity in Adults. 1998. Clinical guidelines on the identification, evaluation, and treatment of overweight and obesity in adults. In The evidence report. National Institutes of Health, Bethesda, Md. 263.

Playford, R. J., T. Marchbank, R. A. Goodlad, R. A. Chinery, et al. 1996. Transgenic mice that overexpress the human trefoil peptide pS2 have an increased resistance to intestinal damage. *Proc Natl Acad Sci USA*. 93:2137–42.

Potter, H. 1988. Electroporation in biology: Methods, applications, and instrumentation. *Analytical Biochemistry*. 174:361–373.

Potter, H., L. Weir, and P. Leder. 1984. Enhancer-dependent expression of human kappa immunoglobulin genes introduced into mouse pre-B lymphocytes by electroporation. *Proc. Natl. Acad. Sci. USA*. 81:7161–7165.

Presta, L. G. 1992. Antibody engineering. *Curr Opin Biotechnol*. 3:394–8.

Prosser, J. 1993. Detecting single-base mutations. *Trends Biotechnol*. 11:238–46.

Rassoulzadegan, M., B. Binetruy, and F. Cuzin. 1982. High frequency of gene transfer after fusion between bacteria and eukaryotic cells. *Nature*. 295:257.

Reisfeld, R. A., and S. Sell. 1985. Monoclonal antibodies and cancer therapy: Proceedings of the Roche-UCLA symposium held in Park City, Utah, January 26–Feb. 2, 1985. Alan R. Liss, New York. 609 pp.

Renkema, G. H., Boot, R. G., Muijsers, A. O., Donker-Koopman, W. E. and Aerts, J. M. (1995) Purification and characterization of human chitotriosidase, a novel member of the chitinase family of proteins. *J Biol Chem* 270, 2198–2202.

Report, A. 1997. Position of the American Dietetic Association: weight management. *J Am Diet Assoc*. 97:71–4.

Rhodes, C. A., D. A. Pierce, I. J. Mettler, D. Mascarenhas, et al. 1988. Genetically transformed maize plants from protoplasts. *Science*. 240:204–207.

Riechmann, L., M. Clark, H. Waldmann, and G. Winter. 1988. Reshaping human antibodies for therapy. *Nature*. 332:323–7.

Rose, J. K., L. Buonocore, and M. Whitt. 1991. A new cationic liposome reagent mediating nearly quantitative transfection of animal cells. *BioTechniques*. 10:520–525.

Rossiter, B. J., and C. T. Caskey. 1990. Molecular scanning methods of mutation detection. *J Biol Chem*. 265:12753–6.

Ruppert, S., Wang, E. H. and Tjian, R. (1993) Cloning and expression of human TAFII250: a TBP-associated factor implicated in cell-cycle regulation. *Nature* 362, 175–179.

Saifer, M., R. Somack, and L. D. Williams. U.S. Pat. No. 5,283,317. Intermediates for conjugation of polypeptides with high molecular weight polyalkylene glycols. 1994.

Saiki, R. K., T. L. Bugawan, G. T. Horn, K. B. Mullis, et al. 1986. Analysis of enzymatically amplified beta-globin and HLA-DQ alpha DNA with allele-specific oligonucleotide probes. *Nature*. 324:163–6.

Saiki, R. K., P. S. Walsh, C. H. Levenson, and H. A. Erlich. 1989. Genetic analysis of amplified DNA with immobilized sequence-specific oligonucleotide probes. *Proc Natl Acad Sci USA*. 86:6230–4.

Sakurai, T., A. Amemiya, M. Ishii, I. Matsuzaki, et al. 1998a. Orexins and orexin receptors: a family of hypothalamic neuropeptides and G protein-coupled receptors that regulate feeding behavior. *Cell*. 92:573–85.

Sakurai, T., A. Amemiya, M. Ishii, I. Matsuzaki, et al. 1998b. Orexins and orexin receptors: a family of hypothalamic neuropeptides and G protein-coupled receptors that regulate feeding behavior. *Cell*. 92:1 page following 696.

Saleeba, J. A., and R. G. Cotton. 1993. Chemical cleavage of mismatch to detect mutations. *Methods Enzymol*. 217:286–95.

Sambrook, J. 1989. Molecular cloning: a laboratory manual. Cold Spring Harbor Laboratory, Cold Spring Harbor.

Sandri-Goldin, R. M., A. L. Goldin, J. C. Glorioso, and M. Levine. 1981. High-frequency transfer of cloned herpes simplex virus type I sequences to mammalian cells by protoplast fusion. *Mol. Cell. Biol*. 1:7453–752.

Sanger, F., S. Nicklen, and A. R. Coulson. 1977. DNA sequencing with chain-terminating inhibitors. *Proc Natl Acad Sci USA*. 74:5463–7.

Saunders, J. A., B. F. Matthews, and P. D. Miller. 1989. Plant gene transfer using electrofusion and electroporation. In Electroporation and electrofusion in cell biology. E. Neumann, A. E. Sowers, and C. A. Jordan, editors. Plenum Press, New York. 343–354.

Schade, R., C. Staak, C. Hendriksen, M. Erhard, et al. 1996. The production of avian (egg yolk) antibodies: IgY. The report and recommendations of ECVAM workshop. *Alternatives to Laboratory Animals (ATLA)*. 24:925–934.

Schaffner, W. 1980. Direct transfer of cloned genes from bacteria to mammalian cells. *Proc. Natl. Acad. Sci. USA*. 77:2163.

Schook, L. B. 1987. Monoclonal antibody production techniques and applications. Marcel Dekker, Inc., New York. 336 pp.

Schrauwen, P., K. Walder, and E. Ravussin. 1999. Human uncoupling proteins and obesity. *Obes Res*. 7:97–105.

Scott, J. K., and G. P. Smith. 1990. Searching for peptide ligands with an epitope library. *Science*. 249:386–90.

Selden, R. F., K. Burke-Howie, M. E. Rowe, H. M. Goodman, et al. 1986. Human growth hormone as a reporter gene in regulation studies employing transient gene expression. *Molecular and Cellular Biology*. 6:3173–3179.

Shalaby, M. R., H. M. Shepard, L. Presta, M. L. Rodrigues, et al. 1992. Development of humanized bispecific antibodies reactive with cytotoxic lymphocytes and tumor cells overexpressing the HER2 protooncogene. *J Exp Med*. 175:217–25.

Shigekawa, K., and W. J. Dower. 1988. Electroporation of eukaryotes and prokaryotes: A general approach to the introduction of macromolecules into cells. *BioTechniques*. 6:742–751.

Shillito, R. 1999. Methods of genetic transformations: Electroporation and polyethylene glycol treatment. In Molecular improvement of cereal crop. I. Vasil, editor. Kluwer, Dordrecht, The Netherlands. 9–20.

Shilo, B. Z., and R. A. Weinberg. 1981. DNA sequences homologous to vertebrate oncogenes are conserved in *Drosophila melanogaster*. *Proc Natl Acad Sci USA*. 78:6789–92.

Shimkets, R. A., D. G. Lowe, J. T. Tai, P. Sehl, et al. 1999. Gene expression analysis by transcript profiling coupled to a gene database query. *Nat Biotechnol*. 17:798–803.

Shopes, B. 1992. A genetically engineered human IgG mutant with enhanced cytolytic activity. *J Immunol*. 148:2918–22.

Simonsen, C. C., and A. D. Levinson. 1983. Isolation and expression of an altered mouse dihydrofolate reductase cDNA. *Proc. Natl. Acad. Sci. USA*. 80:2495–2499.

Sjarif, D. R., J. K. Ploos van Amstel, M. Duran, F. A. Beemer, et al. 2000. Isolated and contiguous glycerol kinase gene disorders: a review. *J Inherit Metab Dis*. 23:529–47.

Smulson, M. E., B. Kishor, and H. Konrad. U.S. Pat. No. 5,272,057. Method of detecting a predisposition to cancer by the use of restriction fragment length polymorphism of the gene for human poly (ADP-ribose) polymerase. 1993.

Sompayrac, L. M. and Danna, K. J. (1981) Efficient infection of monkey cells with DNA of simian virus 40. *Proc Natl Acad Sci USA* 78, 7575–7578.

Southern, P. J., and P. Berg. 1982. Transformation of mammalian cells to antibiotic resistance with a bacterial gene under control of the SV40 early region promoter. *J. Mol. Appl. Gen.* 1:327–341.

Spiegelman, B. M., and J. S. Flier. 1996. Adipogenesis and obesity: rounding out the big picture. *Cell.* 87:377–89.

Sreekrishna, K., R. H. Potenz, J. A. Cruze, W. R. McCombie, et al. 1988. High level expression of heterologous proteins in methylotrophic yeast *Pichia pastoris*. *J Basic Microbiol.* 28:265–78.

Stein, C. A., and J. S. Cohen. 1988. Oligodeoxynucleotides as inhibitors of gene expression: a review. *Cancer Res.* 48:2659–68.

Stevenson, G. T., A. Pindar, and C. J. Slade. 1989. A chimeric antibody with dual Fc regions (bisFabFc) prepared by manipulations at the IgG hinge. *Anticancer Drug Des.* 3:219–30.

Strosberg, A. D. 1997. Structure and function of the beta 3-adrenergic receptor. *Annu Rev Pharmacol Toxicol.* 37:421–50.

Suresh, M. R., A. C. Cuello, and C. Milstein. 1986. Bispecific monoclonal antibodies from hybrid hybridomas. *Methods Enzymol.* 121:210–28.

Thimmappaya, B., Weinberger, C., Schneider, R. J. and Shenk, T. (1982) Adenovirus VAI RNA is required for efficient translation of viral mRNAs at late times after infection. *Cell* 31, 543–551.

Thomas, K. R., and M. R. Capecchi. 1987. Site-directed mutagenesis by gene targeting in mouse embryo-derived stem cells. *Cell.* 51:503–12.

Thompson, J., D. Higgins, and T. Gibson. 1994. CLUSTAL W: Improving the sensitivity of progressive multiple sequence alignment through sequence weighting, positions-specific gap penalties and weight matrix choice. *Nucl. Ac. Res.* 22:4673–4680.

Thompson, J. A., and e. al. 1995. Maize transformation utilizing silicon carbide whiskers: A review. *Euphytica.* 85:75–80.

Tilburn, J., C. Scazzocchio, G. G. Taylor, J. H. Zabicky-Zissman, et al. 1983. Transformation by integration in *Aspergillus nidulans*. *Gene.* 26:205–21.

Touraev, A., and e. al. 1997. Plant male germ line transformation. *Plant J.* 12:949–956.

Traunecker, A., F. Oliveri, and K. Karjalainen. 1991. Myeloma based expression system for production of large mammalian proteins. *Trends Biotechnol.* 9:109–13.

Trick, H. N., and e. al. 1997. Recent advances in soybean transformation. *Plant Tissue Cult. Biotechnol.* 3:9–26.

Tuerk, C., and L. Gold. 1990. Systematic evolution of ligands by exponential enrichment: RNA ligands to bacteriophage T4 DNA polymerase. *Science.* 249:505–10.

Turner, D. L., E. Y. Snyder, and C. L. Cepko. 1990. Lineage-independent determination of cell type in the embryonic mouse retina. *Neuron.* 4:833–845.

Tutt, A., G. T. Stevenson, and M. J. Glennie. 1991. Trispecific F(ab')3 derivatives that use cooperative signaling via the TCR/CD3 complex and CD2 to activate and redirect resting cytotoxic T cells. *J Immunol.* 147:60–9.

U.S. Pat. No. 4,469,863
U.S. Pat. No. 5,177,198
U.S. Pat. No. 5,366,878
U.S. Pat. No. 5,023,243
U.S. Pat. No. 5,130,302
U.S. Pat. No. 5,223,618
U.S. Pat. No. 5,264,562
U.S. Pat. No. 5,264,564
U.S. Pat. No. 5,378,825
U.S. Pat. No. 5,386,023
U.S. Pat. No. 5,476,925
U.S. Pat. No. 5,489,677
U.S. Pat. No. 5,508,270
U.S. Pat. No. 5,602,240
U.S. Pat. No. 5,610,289
U.S. Pat. No. 5,610,289
U.S. Pat. No. 5,623,065
U.S. Pat. No. 5,625,050
U.S. Pat. No. 5,719,262,
U.S. Pat. No. 5,256,775 van der Krol, A. R., J. N. Mol, and A. R. Stuitje. 1988a. Modulation of eukaryotic gene expression by complementary RNA or DNA sequences. *Biotechniques.* 6:958–76.

van der Krol, A. R., J. N. Mol, and A. R. Stuitje. 1988b. Modulation of eukaryotic gene expression by complementary RNA or DNA sequences. *Biotechniques.* 6:958–76.

Verhoeyen, M., C. Milstein, and G. Winter. 1988. Reshaping human antibodies: grafting an antilysozyme activity. *Science.* 239:1534–6.

Vitetta, E. S., R. J. Fulton, R. D. May, M. Till, et al. 1987. Redesigning nature's poisons to create anti-tumor reagents. *Science.* 238:1098–104.

Wagner, T. E., and P. C. Hoppe. U.S. Pat. No. 4,873,191. Genetic transformation of zygotes. 1989.

Weigle, D. S., and J. L. Kuijper. 1996. Obesity genes and the regulation of body fat content. *Bioessays.* 18:867–74.

Wells, J. A., M. Vasser, and D. B. Powers. 1985. Cassette mutagenesis: an efficient method for generation of multiple mutations at defined sites. *Gene.* 34:315–23.

Whitt, M. A., L. Buonocore, J. K. Rose, V. Ciccarone, et al. 1990. TransfectACE reagent promotes transient transfection frequencies greater than 90%. *Focus.* 13:8–12.

Wigler, M., A. Pellicer, S. Silversttein, and R. Axel. 1978. Biochemical transfer of single-copy eukaryotic genes using total cellular DNA as donor. *Cell.* 14:725.

Wikberg, J. E., R. Muceniece, I. Mandrika, P. Prusis, et al. 2000. New aspects on the melanocortins and their receptors. *Pharmacol Res.* 42:393–420.

Williams, D. A., I. R. Lemischka, D. G. Nathan, and R. C. Mulligan. 1984. Introduction of a new genetic material into pluripotent haematopoietic stem cells of the mouse. *Nature.* 310:476–480.

Wilmut, I., A. E. Schnieke, J. McWhir, A. J. Kind, et al. 1997. Viable offspring derived from fetal and adult mammalian cells. *Nature.* 385:810–3.

WO 94/02499
WO 94/17093

Wolff, E. A., G. J. Schreiber, W. L. Cosand, and H. V. Raff. 1993. Monoclonal antibody homodimers: enhanced anti-tumor activity in nude mice. *Cancer Res.* 53:2560–5.

Wong, T. K., and E. Neumann. 1982. Electric field mediated gene transfer. *Biochemical and Biophysical Research Communications.* 107:584–587.

Wong, W. M., R. Poulsom, and N. A. Wright. 1999. Trefoil peptides. *Gut.* 44:890–5.

Wright, N. A., W. Hoffmann, W. R. Otto, M. C. Rio, et al. 1997. Rolling in the clover: trefoil factor family (TFF)-domain peptides, cell migration and cancer. *FEBS Lett.* 408:121–3.

Wyborski, D. L., L. C. DuCoeur, and J. M. Short. 1996. Parameters affecting the use of the lac repressor system in eukaryotic cells and transgenic animals. *Environ Mol Mutagen.* 28:447–58.

Wyborski, D. L., and J. M. Short. 1991. Analysis of inducers of the *E. coli* lac repressor system in mammalian cells and whole animals. *Polynucleotides Res.* 19:4647–53.

Yaswen, L., N. Diehl, M. B. Brennan, and U. Hochgeschwender. 1999. Obesity in the mouse model of pro-opiomelanocortin deficiency responds to peripheral melanocortin. *Nat Med.* 5:1066–70.

Yelton, M. M., J. E. Hamer, and W. E. Timberlake. 1984. Transformation of Aspergillus nidulans by using a trpC plasmid. *Proc Natl Acad Sci USA.* 81:1470–4.

Zervos, A. S., J. Gyuris, and R. Brent. 1993. Mxi1, a protein that specifically interacts with Max to bind Myc-Max recognition sites. *Cell.* 72:223–32.

Zhou, G., and e. al. 1983. Introduction of exogenous DNA into cotton embryos. *Methods Enzymol.* 101:433–481.

Zoller, M. J., and M. Smith. 1987. Oligonucleotide-directed mutagenesis: a simple method using two oligonucleotide primers and a single-stranded DNA template. *Methods Enzymol.* 154:329–50.

Zon, G. 1988. Oligonucleotide analogues as potential chemotherapeutic agents. *Pharm Res.* 5:539–49.

Zuckermann, R. N., E. J. Martin, D. C. Spellmeyer, G. B. Stauber, et al. 1994. Discovery of nanomolar ligands for 7-transmembrane G-protein-coupled receptors from a diverse N-(substituted)glycine peptide library. *J Med Chem.* 37:2678–85.

What is claimed is:

1. A method of monitoring metabolism in an animal having a metabolic disorder comprising:
   (a) contacting a biological sample from the animal with an agent capable of detecting expression levels of an Acidic Mammalian Molecule (AMM) polypeptide comprising SEQ ID NO:2; and
   (b) comparing the expression levels of AMM polypeptide in a control sample with the expression levels of AMM polypeptide in said biological sample to ascertain the AMM polypeptide expression levels in the biological sample, wherein increased expression of AMM polypeptide indicates an increase in metabolism and a decrease in expression indicates a decrease in metabolism.

2. The method of 1, wherein said metabolic disorder is associated with an up-regulation of expression of Acidic Mammalian Molecule polypeptide.

3. The method of claim 2, wherein said metabolic disorder is cachexia.

4. The method of 1, wherein said metabolic disorder is associated with a down-regulation of expression of Acidic Mammalian Molecule polypeptide.

5. The method of claim 4, wherein said metabolic disorder is selected from the group consisting of obesity and diabetes.

6. The method of claim 1, wherein the agent that detects expression levels of a Acidic Mammalian Molecule polypeptide comprising SEQ ID NO:2 is a probe that hybridizes under stringent conditions to a nucleotide sequence of SEQ ID NO:1 or a complement of SEQ ID NO:1.

7. The method of claim 1, wherein the probe is detectably labeled.

8. The method of claim 1, wherein the agent that detects expression levels is a primer that is complementary to a portion of a nucleotide sequence of SEQ ID NO:1 or a complement of SEQ ID NO:1.

* * * * *

UNITED STATES PATENT AND TRADEMARK OFFICE
CERTIFICATE OF CORRECTION

| | | |
|---|---|---|
| PATENT NO. | : 6,872,704 B2 | Page 1 of 8 |
| APPLICATION NO. | : 10/268919 | |
| DATED | : March 29, 2005 | |
| INVENTOR(S) | : Kelly et al. | |

It is certified that error appears in the above-identified patent and that said Letters Patent is hereby corrected as shown below:

Title page, (56) References Cited, Other Publications, Aron reference: "Appleton & Lang," should read --Appleton & Lange,--

Other Publications, Page 2, Hollack reference: "Hollack" should read --Hollak--

Other Publications, Page 2, Boot reference: "Boot, R.B.," should read --Boot, R.G.,--

Col. 7, line 67: "fragments thereof The" should read --fragments thereof. The--

Cols. 9-10, Table 4: Table 4 should not be split. The entire table should be in Col. 9

Col. 15, lines 64-67: Delete lines 64-67 starting with "Table 9" and ending with "416-475)."

Col. 23, Table 13, line 2: "220" should read --120--

Col. 27, Table 14, first column, second row of each group: "1.36GBbc011134Mmehemokine" should read --1.36GBbc011134Mmchemokine--

Col. 28, Table 14, second column, last row of second group, last 10 nucleotides in the row for HsAMCaseprecAF290004.1: "ACTGGCCCTTT" should read --ACTGCCCCTTT --

Col. 28, Table 14, second column, second row of third group, last 17 nucleotides in the row 1.36GBbc011134Mmchemokine: "ACCTCAGTGATGAAATT" should read --ACCTCAGTCATCAAATT--

Col. 28, Table 14, second column, fourth row of third group, last 17 nucleotides in the row for HsEosChemokineNM021797: "ACCTGAGTCATGAAATT" should read --ACCTCAGTCATCAAATT--

Col. 28, Table 14, second column, third row of last group, nucleotides 18-27 in the row for 1.36GBaf290003Mmchitinaseprecu: "ACAATGGACC" should read --ACAATGGAGC--

Col. 28, Table 14, second column, fourth row of last group, nucleotides 29-45 in the row HsEosChemokineNM021797: "CCACCTGAGAAGCTCAT" should read --CCAGCTGAGAAGCTCAT--

UNITED STATES PATENT AND TRADEMARK OFFICE
CERTIFICATE OF CORRECTION

PATENT NO. : 6,872,704 B2
APPLICATION NO. : 10/268919
DATED : March 29, 2005
INVENTOR(S) : Kelly et al.

It is certified that error appears in the above-identified patent and that said Letters Patent is hereby corrected as shown below:

Col. 28, Table 14, second column, fifth row of last group, nucleotides 29-45 in the row HsAMCaseprecAF290004.1: "CCACCTGAGAAGCTCAT" should read --CCAGCTGAGAAGCTCAT--

Col. 29, Table 14, first column, second row of each group: "1.36GBbc011134Mmehemokine" should read --1.36GBbc011134Mmchemokine--

Col. 30, Table 14, second column, first row of 9th group, nucleotides 20-28 in the row 1.3610e1167.4cgmml0el167.4_376: "CAAAGGAGA" should read --CAAAGCAGA--

Col. 30, Table 14, second column, second row of 9th group, nucleotides 20-28 of the row 1.36GBbc011134Mmchemokine: "CAAAGGAGA" should read --CAAAGCAGA--

Col. 30, Table 14, second column, third row of 9th group, nucleotides 20-28 of the row 1.36GBaf290003Mmchitinaseprecu: "CAAAGGAGA" should read --CAAAGCAGA--

Col. 30, Table 14, second column, fourth row of 9th group, nucleotides 42-47 of the row HsEosChemokineNM021797: "GTGGGA" should read --GTGGCA--

Col. 30, Table 14, second column, second row of 11th group, last 12 nucleotides in the row 1.36GBbc011134Mmchemokine: "ATTTTTCCAGAA" should read --ATTCTTCCAGAA--

Col. 30, Table 14, second column, third row of 11th group, last 12 nucleotides of the row 1.36GBaf290003Mmchitinaseprecu: "ATTTTTCCAGAA" should read --ATTCTTCCAGAA--

Cols. 31-32, Table 15: "473 aa 11" should read --473 aa SEQ ID NO: 11--

Cols. 31-32, Table 15: "365 aa 4" should read --365 aa SEQ ID NO: 4--

Cols. 31-32, Table 15: "368 aa 13" should read --368 an SEQ ID NO:13--

Cols. 31-32, Table 15; "476 aa 5" should read --476 aa SEQ ID NO:5--

Cols. 31-32, Table 15: "65 aa 2" should read --65aa SEQ ID NO:2--

UNITED STATES PATENT AND TRADEMARK OFFICE
CERTIFICATE OF CORRECTION

PATENT NO. : 6,872,704 B2
APPLICATION NO. : 10/268919
DATED : March 29, 2005
INVENTOR(S) : Kelly et al.

It is certified that error appears in the above-identified patent and that said Letters Patent is hereby corrected as shown below:

Cols. 31-32, Table 15, first column, first row of each group: "1 36Q99PH2MmAMCase" should read --1.36Q99PH2MmAMCase--

Cols. 31-32, Table 15, first column, second row of each group: "1 36aaH11134MmEosChemo" should read --1.36AAH11134MmEosChemo--

Cols. 31-32, Table 15, first column, third row of each group: "1 3610e11674cgmm10311674_376" should read --1.3610e1167.4cgmml0el 167.4_376--

Cols. 31-32, Table 15, first column, fourth row of each group: "1 36Q9ULY4HsNovChitmase" should read --1.36Q9ULY4HsNovChitinase--

Cols. 31-32, Table 15, first column, fifth row of each group: "136Q9BZP6HsAMCasePrec" should read --1.36Q9BZP6HsAMCasePrec--

Cols. 31-32, Table 15, second column, first row of third group, amino acids 138-149 of the row 1.36Q99PH2MmAMCase: "DWEYFGSRGSPP" should read --DWEYPGSRGSPP--

Cols. 31-32, Table 15, second column, second row of third group, amino acids 30-41 of the row 1.36AAH11134MmEosChemo: "DWEYFGSRGSPP" should read --DWEYPGSRGSPP--

Cols. 31-32, Table 15, second column, fourth row of third group, amino acids 30-41 of the row 1.36Q9ULY4HsNovChitinase: "DWEYFGSRGSPP" should read --DWEYPGSRGSPP--

Cols. 31-32, Table 15, second column, fifth row of third group, amino acids 138-149 of the row 1.36Q9BZP6HsAMCasePrec: "DWEYFGSRGSPP" should read --DWEYPGSRGSPP--

Cols. 31-32, Table 15, second column, first row of fourth group, amino acids 197-208 of the row 1.36Q99PH2MmAMCase: "IPELSKVLDFIH" should read --IPELSKYLDFIH--

Cols. 31-32, Table 15, second column, second row of fourth group, amino acids 89-100 of the row 1.36AAH11134MmEosChemo: "IPELSKVLDFIH" should read --IPELSKYLDFIH--

Cols. 31-32, Table 15, second column, fourth row of fourth group, amino acids

UNITED STATES PATENT AND TRADEMARK OFFICE
CERTIFICATE OF CORRECTION

PATENT NO. : 6,872,704 B2  Page 4 of 8
APPLICATION NO. : 10/268919
DATED : March 29, 2005
INVENTOR(S) : Kelly et al.

It is certified that error appears in the above-identified patent and that said Letters Patent is hereby corrected as shown below:

89-100 of the row 1.36Q9ULY4HsNovChitinase: "IPQLSQVLDYIH" should read --IPQLSQYLDYIH--

Cols. 31-32, Table 15, second column, fifth row of fourth group, amino acids 197-208 of the row 1.36Q9BZP6HsAMCasePrec: "IPQLSQVLDYIH" should read --IPQLSQYLDYIH--

Cols. 31-32, Table 15, second column, first row of fifth group, amino acids 289-300 of the row 1.36Q99PH2MmAMCase: "GPAGA TRQAGF" should read --GPAGAYTRQAGF--

Cols. 31-32, Table 15, second column, first row of last group, amino acids 354-360 of the row 1.36Q99PH2MmAMCase: "FGGAMI" should read --FGGAMIW--

Cols. 31-32, Table 15, second column, second row of last group, amino acids 246-252 of the row 1.36AAH11134MmEosChemo: "FGGAMI" should read --FGGAMIW--

Cols. 31-32, Table 15, second column, fourth row of last group, amino acids 246-252 of the row 1.36Q9ULY4HsNovChitinase: "FGGAMV "should read --FGGAMVW--

Cols. 31-32, Table 15, second column, fifth row of last group, amino acids 354-360 of the row 1.36Q9BZP6HsAMCasePrec: "FGGAMV "should read --FGGAMVW--

Cols. 33-34, Table 15, first column, first row of each group:
"1 36Q99PH2MmAMCase" should read --1.36Q99PH2MmAMCase--

Cols. 33-34, Table 15, first column, second row of each group:
"1 36AAH11134MmEosChemo" should read --1.36AAH11134MmEosChemo--

Cols. 33-34, Table 15, first column, third row of each group:
"1 3610e11674cgmm103l1674_376" should read -1.3610e1167.4cgmm10e1167.4_376--

Cols. 33-34, Table 15, first column, fourth row of each group:
"1 36Q9ULY4HsNovChitmase" should read--1.36Q9ULY4HsNovChitinase--

Cols. 33-34, Table 15, first column, fifth row of each group: "1 36Q9BZP6HsAMCasePrec" should read --1.36Q9BZP6HsAMCasePrec--

UNITED STATES PATENT AND TRADEMARK OFFICE
CERTIFICATE OF CORRECTION

PATENT NO.      : 6,872,704 B2
APPLICATION NO. : 10/268919
DATED           : March 29, 2005
INVENTOR(S)     : Kelly et al.

It is certified that error appears in the above-identified patent and that said Letters Patent is hereby corrected as shown below:

Cols. 33-34, Table 15, second column, first row of first group, amino acids 394-417 of the row 1.36Q99PH2MmAMCase: "STAFDVPSEPVTTPP---GSGSGGGS" should read -- CTAPDVPSEPVTTPP---GSGSGGGSS--

Cols. 33-34, Table 15, second column, second row of first group, amino acids 286-309 of the row 1.36AAH11134MmEosChemo: "STAFDVPSEPVTTPP---GSGSGGGS " should read --CTAPDVPSEPVTTPP---GSGSGGGSS--

Cols. 33-34, Table 15, second column, third row of first group, amino acids 1-9 of the row 1.3610e1167.4cgmm10e1167.4_376: "EVRVGVEA" should read --EVRVGVEAS--

Cols. 33-34, Table 15, second column, fourth row of first group, amino acids 286-312 of the row 1.36Q9ULY4HsNovChitinase: "STAFAQPIEPITAAPSGSGNGSGSSS " should read --CTAPAQPIEPITAAPSGSGNGSGSSSS--

Cols. 33-34, Table 15, second column, fifth row of first group, amino acids 394-420 of the row 1.36Q9BZP6HsAMCasePrec: "STAFAQPIEPITAAPSGSGNGSGSSS " should read -- CTAPAQPIEPITAAPSGSGNGSGSSSS--

Cols. 33-34, Table 15, second column, first row of second group, amino acids 451-462 of the row 1.36Q99PH2MmAMCase: "ITYQQHGQAGLV" should read --ITYQQHCQAGLV--

Cols. 33-34, Table 15, second column, second row of second group, amino acids 343-354 of the row 1.36AAH11134MmEosChemo: "ITYQQHGQAGLV" should read --ITYQQHCQAGLV--

Cols. 33-34, Table 15, second column, third row of second group, amino acids 43-54 of the row 1.36 l0e1167.4cgmm10e1167.4_376: "ITYQQHGQAGLV" should read --ITYQQHCQAGLV--

Cols. 33-34, Table 15, second column, fourth row of second group, amino acids 346-357 of the row 1.36Q9ULY4HsNovChitinase: "ITYQQNGQAGLV" should read --VTYQQNCQAGLV--

Cols. 33-34, Table 15, second column, fifth row of second group, amino acids 454-465 of the row 1.36Q9BZP6HsAMCasePrec: "ITYQQNGQAGLV" should read --VTYQQNCQAGLV--

UNITED STATES PATENT AND TRADEMARK OFFICE
CERTIFICATE OF CORRECTION

| | |
|---|---|
| PATENT NO. | : 6,872,704 B2 |
| APPLICATION NO. | : 10/268919 |
| DATED | : March 29, 2005 |
| INVENTOR(S) | : Kelly et al. |

It is certified that error appears in the above-identified patent and that said Letters Patent is hereby corrected as shown below:

Col. 36, line 1: "in SEq ID NO:2," should read --in SEQ ID NO:2,--

Col. 37, line 19: "shown in SEq ID NO:2." should read --shown in SEQ ID NO:2.--

Col. 43, line 44: "SEq ID NO:2. The" should read --SEQ ID NO:2. The--

Col. 43, line 47: "SEq ID NO:2, while" should read --SEQ ID NO:2, while--

Col. 45, line 1: "(SEq ID NO:2) that" should read --(SEQ ID NO:2) that--

Col. 45, line 12: "in SEq ID NO:2, or" should read --in SEQ ID NO:2, or--

Col. 45, line 13: "to SEq ID NO:2, and" should read --to SEQ ID NO:2, and--

Col. 45, line 14: "SEq ID NO:2, yet differs" should read --SEQ ID NO:2, yet differs--

Col. 45, line 18: "of SEq ID NO:2, and" should read --of SEQ ID NO:2, and--

Col. 46, line 1: "(SEq ID NO:2). An AMM" should read --(SEQ ID NO:2). An AMM--

Col. 59, line 51: "to development the" should read --to development of the--

Col. 66, line 3: "membrane-bound forms" should read --membrane-bound form--

Col. 73, line 20: "clinical trails of subjects" should read --clinical trials of subjects--

Col. 74, line 16: "endogenous function of" should read --endogenous function--

Col. 75, line 33: "animal model system" should read --animal model systems--

Col. 79, line 49" "Use of AAM" should read --Use of AMM--

Col. 79, line 52: "sequence encoding AAM" should read --sequence encoding AMM--

UNITED STATES PATENT AND TRADEMARK OFFICE
CERTIFICATE OF CORRECTION

PATENT NO. : 6,872,704 B2
APPLICATION NO. : 10/268919
DATED : March 29, 2005
INVENTOR(S) : Kelly et al.

It is certified that error appears in the above-identified patent and that said Letters Patent is hereby corrected as shown below:

Col 79, line 54: "mature AAM (or unique" should read --mature AMM (or unique--

Col. 79, line 56: "AAM mRNA in a sample" should read --AMM mRNA in a sample--

Col. 79, line 58: "Radiolabeled AAM-derived" should read --Radiolabeled AMM-derived--

Col. 81, line 5: "density (3-5 at $0D_{60D}$)" should read --density (3-5 at $0D_{600}$)--

Col. 81, line 13: "30°C. with agitalion." should read --30°C. with agitation.--

Col. 82, line 38: "pRKS-AAM DNA is added." should read --pRK5-AMM DNA is added.--

Col. 83, line 38: "One 1 ml fractions" should read --One (1) ml fractions--

Col. 84, line 66: "Oligonucleotide Synthesis" should read --<u>Oligonucleotide Synthesis</u>--

Col. 85, line 37: "PNA Synthesis" should read --PNA <u>Synthesis</u>--

Col. 85, line 43: "Synthesis of Chimeric Oligonucleotides" should read --<u>Synthesis of Chimeric Oligonucleotides</u>--

Col. 86, line 63: "Homozygous AAM Knockout" should read --Homozygous AMM Knockout--

Col. 102, line 14: Delete duplicate "U.S. Pat. No. 5,610,289"

Col. 119, line 42, claim 1: "agent capable of detecting" should read --agent that detects--

Col. 119, line 53, claim 2: "The method of 1," should read --The method of claim 1,--

UNITED STATES PATENT AND TRADEMARK OFFICE
CERTIFICATE OF CORRECTION

PATENT NO. : 6,872,704 B2
APPLICATION NO. : 10/268919
DATED : March 29, 2005
INVENTOR(S) : Kelly et al.

It is certified that error appears in the above-identified patent and that said Letters Patent is hereby corrected as shown below:

Col. 120, line 38, claim 4: "The method of 1," should read --The method of claim 1,--

Signed and Sealed this

Twelfth Day of December, 2006

JON W. DUDAS
*Director of the United States Patent and Trademark Office*

SEQUENCE LISTING

<160> NUMBER OF SEQ ID NOS: 10

<210> SEQ ID NO 1
<211> LENGTH: 319
<212> TYPE: DNA
<213> ORGANISM: Mus musculus

<400> SEQUENCE: 1
gtaggaagtg agagtgggggg tggaagcttc cggaggaagc tttggaggca gtggattttg     60
tgccgacaaa gcagatggcc tttaccctgt ggcagatgac agaaatgctt tttggcagtg    120
catcaatgga atcacatacc agcagcattg tcaagcaggg cttgttttttg ataccagctg    180 taattgctgc aactggccat gaacctaatg ccattttttcc agaaattttt gcattttcct    240
ttattcctca ccaaaagtaa cttttttccc tttaacctta tgcaataaaa ttggtagccg    300
taaaaaaaaa aaaaaaaaa                                                 319

<210> SEQ ID NO 2
<211> LENGTH: 65
<212> TYPE: PRT
<213> ORGANISM: Mus musculus

<400> SEQUENCE: 2

Glu Val Arg Val Gly Val Glu Ala Ser Gly Gly Ser Phe Gly Gly Ser
1               5                   10                  15

Gly Phe Cys Ala Asp Lys Ala Asp Gly Leu Tyr Pro Val Ala Asp Asp
            20                  25                  30

Arg Asn Ala Phe Trp Gln Cys Ile Asn Gly Ile Thr Tyr Gln Gln His
        35                  40                  45

Cys Gln Ala Gly Leu Val Phe Asp Thr Ser Cys Asn Cys Cys Asn Trp
    50                  55                  60

Pro
65

<210> SEQ ID NO 3
<211> LENGTH: 520
<212> TYPE: PRT
<213> ORGANISM: Mus musculus

<400> SEQUENCE: 3

Gly Ile Gly Asx Ala Ala Gly Ala Phe Ala Cys Ile Asp Ile Cys Met
1               5                   10                  15

Ala Met Met Ala Leu Ile Ala Asn Cys His Ile Thr Ile Asn Ala Ser

-continued

```
            20                  25                  30
Glu Pro Arg Glu Cys Arg Ser Arg Met Ser Met Ser Cys Leu Ser Met
            35                  40                  45
Ala Lys Leu Leu Leu Val Thr Gly Leu Ala Leu Leu Leu Asn Ala Gln
50                  55                  60
Leu Gly Ser Ala Tyr Asn Leu Ile Cys Tyr Phe Thr Asn Trp Ala Gln
65                  70                  75                  80
Tyr Arg Pro Gly Leu Gly Ser Phe Lys Pro Asp Asp Ile Asn Pro Cys
                85                  90                  95
Leu Cys Thr His Leu Ile Tyr Ala Phe Ala Gly Met Gln Asn Asn Glu
            100                 105                 110
Ile Thr Thr Ile Glu Trp Asn Asp Val Thr Leu Tyr Lys Ala Phe Asn
            115                 120                 125
Asp Leu Lys Asn Arg Asn Ser Lys Leu Lys Thr Leu Leu Ala Ile Gly
            130                 135                 140
Gly Trp Asn Phe Gly Thr Ala Pro Phe Thr Thr Met Val Ser Thr Ser
145                 150                 155                 160
Gln Asn Arg Gln Thr Phe Ile Thr Ser Val Ile Lys Phe Leu Arg Gln
                165                 170                 175
Tyr Gly Phe Asp Gly Leu Asp Leu Asp Trp Glu Tyr Pro Gly Ser Arg
            180                 185                 190
Gly Ser Pro Pro Gln Asp Lys His Leu Phe Thr Val Leu Val Lys Glu
        195                 200                 205
Met Arg Glu Ala Phe Glu Gln Glu Ala Ile Glu Ser Asn Arg Pro Arg
    210                 215                 220
Leu Met Val Thr Ala Ala Val Ala Gly Gly Ile Ser Asn Ile Gln Ala
225                 230                 235                 240
Gly Tyr Glu Ile Pro Glu Leu Ser Lys Tyr Leu Asp Phe Ile His Val
                245                 250                 255
Met Thr Tyr Asp Leu His Gly Ser Trp Glu Gly Tyr Thr Gly Glu Asn
            260                 265                 270
Ser Pro Leu Tyr Lys Tyr Pro Thr Glu Thr Gly Ser Asn Ala Tyr Leu
        275                 280                 285
Asn Val Asp Tyr Val Met Asn Tyr Trp Lys Asn Asn Gly Ala Pro Ala
    290                 295                 300
Glu Lys Leu Ile Val Gly Phe Pro Glu Tyr Gly His Thr Phe Ile Leu
305                 310                 315                 320
Arg Asn Pro Ser Asp Asn Gly Ile Gly Ala Pro Thr Ser Gly Asp Gly
                325                 330                 335
Pro Ala Gly Ala Tyr Thr Arg Gln Ala Gly Phe Trp Ala Tyr Tyr Glu
            340                 345                 350
Ile Cys Thr Phe Leu Arg Ser Gly Ala Thr Glu Val Trp Asp Ala Ser
        355                 360                 365
Gln Glu Val Pro Tyr Ala Tyr Lys Ala Asn Glu Trp Leu Gly Tyr Asp
    370                 375                 380
Asn Ile Lys Ser Phe Ser Val Lys Ala Gln Trp Leu Lys Gln Asn Asn
385                 390                 395                 400
Phe Gly Gly Ala Met Ile Trp Ala Ile Asp Leu Asp Asp Phe Thr Gly
                405                 410                 415
Ser Phe Cys Asp Gln Gly Lys Phe Pro Leu Thr Ser Thr Leu Asn Lys
            420                 425                 430
Ala Leu Gly Ile Ser Thr Glu Gly Cys Thr Ala Pro Asp Val Pro Ser
        435                 440                 445
```

```
Glu Pro Val Thr Thr Pro Pro Gly Ser Gly Ser Gly Gly Gly Ser Ser
    450                 455                 460

Gly Gly Ser Ser Gly Gly Ser Gly Phe Cys Ala Asp Lys Ala Asp Gly
465             470                 475                 480

Leu Tyr Pro Val Ala Asp Asp Arg Asn Ala Phe Trp Gln Cys Ile Asn
                485                 490                 495

Gly Ile Thr Tyr Gln Gln His Cys Gln Ala Gly Leu Val Phe Asp Thr
                500                 505                 510

Ser Cys Asn Cys Cys Asn Trp Pro
        515                 520

<210> SEQ ID NO 4
<211> LENGTH: 415
<212> TYPE: PRT
<213> ORGANISM: Mus musculus

<400> SEQUENCE: 4

Gly Ile Gly Asx Ala Ala His Ala Ala His Ser Ile Met Ile Leu Ala
1               5                   10                  15

Arg Thr Glu Ser Ile Asn Pro His Ile Leu Cys His Glu Met Thr Ala
            20                  25                  30

Cys Thr Ile Cys Cys Tyr Thr Lys Ile Asn Glu Met Ser Met Ser Cys
        35                  40                  45

Leu Ser Met Val Ser Thr Ser Gln Asn Arg Gln Thr Phe Ile Thr Ser
    50                  55                  60

Val Ile Lys Phe Leu Arg Gln Tyr Gly Phe Asp Gly Leu Asp Leu Asp
65                  70                  75                  80

Trp Glu Tyr Pro Gly Ser Arg Gly Ser Pro Gln Asp Lys His Leu
                85                  90                  95

Phe Thr Val Leu Val Lys Glu Met Arg Glu Ala Phe Glu Gln Glu Ala
                100                 105                 110

Ile Glu Ser Asn Arg Pro Arg Leu Met Val Thr Ala Ala Val Ala Gly
            115                 120                 125

Gly Ile Ser Asn Ile Gln Ala Gly Tyr Glu Ile Pro Glu Leu Ser Lys
    130                 135                 140

Tyr Leu Asp Phe Ile His Val Met Thr Tyr Asp Leu His Gly Ser Trp
145                 150                 155                 160

Glu Gly Tyr Thr Gly Glu Asn Ser Pro Leu Tyr Lys Tyr Pro Thr Glu
                165                 170                 175

Thr Gly Ser Asn Ala Tyr Leu Asn Val Asp Tyr Val Met Asn Tyr Trp
                180                 185                 190

Lys Asn Asn Gly Ala Pro Ala Glu Lys Leu Ile Val Gly Phe Pro Glu
            195                 200                 205

Tyr Gly His Thr Phe Ile Leu Arg Asn Pro Ser Asp Asn Gly Ile Gly
    210                 215                 220

Ala Pro Thr Ser Gly Asp Gly Pro Ala Gly Pro Tyr Thr Arg Gln Ala
225                 230                 235                 240

Gly Phe Trp Ala Tyr Tyr Glu Ile Cys Thr Phe Leu Arg Ser Gly Ala
                245                 250                 255

Thr Glu Val Trp Asp Ala Ser Gln Glu Val Pro Tyr Ala Tyr Lys Ala
                260                 265                 270

Asn Glu Trp Leu Gly Tyr Asp Asn Ile Lys Ser Phe Ser Val Lys Ala
            275                 280                 285

Gln Trp Leu Lys Gln Asn Asn Phe Gly Gly Ala Met Ile Trp Ala Ile
```

```
            290                 295                 300
Asp Leu Asp Asp Phe Thr Gly Ser Phe Cys Asp Gln Gly Lys Phe Pro
305                 310                 315                 320

Leu Thr Ser Thr Leu Asn Lys Ala Leu Gly Ile Ser Thr Glu Gly Cys
                325                 330                 335

Thr Ala Pro Asp Val Pro Ser Glu Pro Val Thr Thr Pro Pro Gly Ser
                340                 345                 350

Gly Ser Gly Gly Gly Ser Ser Gly Gly Ser Ser Gly Gly Ser Gly Phe
                355                 360                 365

Cys Ala Asp Lys Ala Asp Gly Leu Tyr Pro Val Ala Asp Asp Arg Asn
370                 375                 380

Ala Phe Trp Gln Cys Ile Asn Gly Ile Thr Tyr Gln Gln His Cys Gln
385                 390                 395                 400

Ala Gly Leu Val Phe Asp Thr Ser Cys Asn Cys Cys Asn Trp Pro
                405                 410                 415

<210> SEQ ID NO 5
<211> LENGTH: 476
<212> TYPE: PRT
<213> ORGANISM: Homo sapiens

<400> SEQUENCE: 5

Met Thr Lys Leu Ile Leu Leu Thr Gly Leu Val Leu Ile Leu Asn Leu
1               5                   10                  15

Gln Leu Gly Ser Ala Tyr Gln Leu Thr Cys Tyr Phe Thr Asn Trp Ala
                20                  25                  30

Gln Tyr Arg Pro Gly Leu Gly Arg Phe Met Pro Asp Asn Ile Asp Pro
            35                  40                  45

Cys Leu Cys Thr His Leu Ile Tyr Ala Phe Ala Gly Arg Gln Asn Asn
        50                  55                  60

Glu Ile Thr Thr Ile Glu Trp Asn Asp Val Thr Leu Tyr Gln Ala Phe
65                  70                  75                  80

Asn Gly Leu Lys Asn Lys Asn Ser Gln Leu Lys Thr Leu Leu Ala Ile
                85                  90                  95

Gly Gly Trp Asn Phe Gly Thr Ala Pro Phe Thr Ala Met Val Ser Thr
            100                 105                 110

Pro Glu Asn Arg Gln Thr Phe Ile Thr Ser Val Ile Lys Phe Leu Arg
        115                 120                 125

Gln Tyr Glu Phe Asp Gly Leu Asp Phe Asp Trp Glu Tyr Pro Gly Ser
130                 135                 140

Arg Gly Ser Pro Pro Gln Asp Lys His Leu Phe Thr Val Leu Val Gln
145                 150                 155                 160

Glu Met Arg Glu Ala Phe Glu Gln Glu Ala Lys Gln Ile Asn Lys Pro
                165                 170                 175

Arg Leu Met Val Thr Ala Ala Val Ala Ala Gly Ile Ser Asn Ile Gln
            180                 185                 190

Ser Gly Tyr Glu Ile Pro Gln Leu Ser Gln Tyr Leu Asp Tyr Ile His
        195                 200                 205

Val Met Thr Tyr Asp Leu His Gly Ser Trp Glu Gly Tyr Thr Gly Glu
210                 215                 220

Asn Ser Pro Leu Tyr Lys Tyr Pro Thr Asp Thr Gly Ser Asn Ala Tyr
225                 230                 235                 240

Leu Asn Val Asp Tyr Val Met Asn Tyr Trp Lys Asp Asn Gly Ala Pro
                245                 250                 255
```

```
Ala Glu Lys Leu Ile Val Gly Phe Pro Thr Tyr Gly His Asn Phe Ile
            260                 265                 270
Leu Ser Asn Pro Ser Asn Thr Gly Ile Gly Ala Pro Thr Ser Gly Ala
            275                 280                 285
Gly Pro Ala Gly Pro Tyr Ala Lys Glu Ser Gly Ile Trp Ala Tyr Tyr
            290                 295                 300
Glu Ile Cys Thr Phe Leu Lys Asn Gly Ala Thr Gln Gly Trp Asp Ala
305                 310                 315                 320
Pro Gln Glu Val Pro Tyr Ala Tyr Gln Gly Asn Val Trp Val Gly Tyr
                325                 330                 335
Asp Asn Ile Lys Ser Phe Asp Ile Lys Ala Gln Trp Leu Lys His Asn
            340                 345                 350
Lys Phe Gly Gly Ala Met Val Trp Ala Ile Asp Leu Asp Asp Phe Thr
            355                 360                 365
Gly Thr Phe Cys Asn Gln Gly Lys Phe Pro Leu Ile Ser Thr Leu Lys
            370                 375                 380
Lys Ala Leu Gly Leu Gln Ser Ala Ser Cys Thr Ala Pro Ala Gln Pro
385                 390                 395                 400
Ile Glu Pro Ile Thr Ala Ala Pro Ser Gly Ser Gly Asn Gly Ser Gly
                405                 410                 415
Ser Ser Ser Ser Gly Gly Ser Ser Gly Gly Ser Gly Phe Cys Ala Val
            420                 425                 430
Arg Ala Asn Gly Leu Tyr Pro Val Ala Asn Asn Arg Asn Ala Phe Trp
            435                 440                 445
His Cys Val Asn Gly Val Thr Tyr Gln Gln Asn Cys Gln Ala Gly Leu
            450                 455                 460
Val Phe Asp Thr Ser Cys Asp Cys Cys Asn Trp Ala
465                 470                 475

<210> SEQ ID NO 6
<211> LENGTH: 1354
<212> TYPE: DNA
<213> ORGANISM: Homo sapiens

<400> SEQUENCE: 6
gaaacctcct cgtctgtgca cgaacaggtg gccgactctg gagcccaggc tgttgctttc      60
cagtctggtg gtgaatcctc catagtctgg aacagccagc tgaaaactct cctggccatt     120
ggaggctgga acttcaggac tgccccttc actgccatgg tttctactcc tgagaaccgc     180
cagactttca tcacctcagt catcaaattc ctgcgccagt atgagtttga cgggctggac     240
tttgactggg agtaccctgg ctctcgtggg agccctcctc aggacaagca tctcttcact     300
gtcctggtgc aggaaatgcg tgaagctttt gagcaggagg ccaagcagat caacaagccc     360
aggctgatgg tcactgctgc agtagctgct ggcatctcca atatccagtc tggctatgag     420 atccccaac tgtcacagta cctggactac atccatgtca tgacctacga cctccatggc     480
tcctgggagg gctacactgg agagaacagc cccctctaca atacccgac tgacaccggc     540 agcaacgcct acctcaatgt ggattatgtc atgaactact ggaaggacaa tggagcacca     600
gctgagaagc tcatcgttgg attccctacc tatggacaca cttcatcct gagcaacccc     660 tccaacactg gaattggtgc ccccacctct ggtgctggtc ctgctgggcc ctatgccaag     720
gagtctggga tctgggctta ctacgagatc tgtaccttcc tgaaaaatgg agccactcag     780
ggatgggatg cccctcagga agtgccttat gcctatcagg gcaatgtgtg ggttggctat     840
gacaacgtca agagcttcga tattaaggct caatggctta agcacaacaa atttggaggc     900
```

```
gccatggtct gggccattga tctggatgac ttcactggca ctttctgcaa ccagggcaag      960 tttccctaa  tctccaccct gaagaaggcc cttggcctgc agagtgcaag ttgcacggct     1020
ccagctcagc ccattgagcc aataactgct gctcccagtg gcagcgggaa cgggagcggg     1080
agtagcagct ctggaggcag ctcgggaggc agtggattct gtgctggcag agccaacggc     1140
ctctaccccg tggcaaataa cagaaatgcc ttctggcact gcgtgaatgg agtcacgtac     1200
cagcagaact gccaggccgg gcttgtcttc gacaccagct gtgattgctg caactgggca     1260
taaacctgac ctggtctata ttccctagag ttccagtctc ttttgcttag gacatgttgc     1320
ccctacctaa agtcctgcaa taaaatcagc agtc                                 1354
```

<210> SEQ ID NO 7
<211> LENGTH: 368
<212> TYPE: PRT
<213> ORGANISM: Homo sapiens

<400> SEQUENCE: 7

```
Met Val Ser Thr Pro Glu Asn Arg Gln Thr Phe Ile Thr Ser Val Ile
1               5                   10                  15

Lys Phe Leu Arg Gln Tyr Glu Phe Asp Gly Leu Asp Phe Asp Trp Glu
            20                  25                  30

Tyr Pro Gly Ser Arg Gly Ser Pro Pro Gln Asp Lys His Leu Phe Thr
        35                  40                  45

Val Leu Val Gln Glu Met Arg Glu Ala Phe Glu Gln Glu Ala Lys Gln
    50                  55                  60

Ile Asn Lys Pro Arg Leu Met Val Thr Ala Ala Val Ala Ala Gly Ile
65                  70                  75                  80

Ser Asn Ile Gln Ser Gly Tyr Glu Ile Pro Gln Leu Ser Gln Tyr Leu
                85                  90                  95

Asp Tyr Ile His Val Met Thr Tyr Asp Leu His Gly Ser Trp Glu Gly
            100                 105                 110

Tyr Thr Gly Glu Asn Ser Pro Leu Tyr Lys Tyr Pro Thr Asp Thr Gly
        115                 120                 125

Ser Asn Ala Tyr Leu Asn Val Asp Tyr Val Met Asn Tyr Trp Lys Asp
    130                 135                 140

Asn Gly Ala Pro Ala Glu Lys Leu Ile Val Gly Phe Pro Thr Tyr Gly
145                 150                 155                 160

His Asn Phe Ile Leu Ser Asn Pro Ser Asn Thr Gly Ile Gly Ala Pro
                165                 170                 175

Thr Ser Gly Ala Gly Pro Ala Gly Pro Tyr Ala Lys Glu Ser Gly Ile
            180                 185                 190

Trp Ala Tyr Tyr Glu Ile Cys Thr Phe Leu Lys Asn Gly Ala Thr Gln
        195                 200                 205

Gly Trp Asp Ala Pro Gln Glu Val Pro Tyr Ala Tyr Gln Gly Asn Val
    210                 215                 220

Trp Val Gly Tyr Asp Asn Val Lys Ser Phe Asp Ile Lys Ala Gln Trp
225                 230                 235                 240

Leu Lys His Asn Lys Phe Gly Gly Ala Met Val Trp Ala Ile Asp Leu
                245                 250                 255

Asp Asp Phe Thr Gly Thr Phe Cys Asn Gln Gly Lys Phe Pro Leu Ile
            260                 265                 270

Ser Thr Leu Lys Lys Ala Leu Gly Leu Gln Ser Ala Ser Cys Thr Ala
        275                 280                 285
```

```
           Pro Ala Gln Pro Ile Glu Pro Ile Thr Ala Ala Pro Ser Gly Ser Gly
               290                 295                 300

Asn Gly Ser Gly Ser Ser Ser Gly Gly Ser Ser Gly Gly Ser Gly
           305                 310                 315                 320

Phe Cys Ala Gly Arg Ala Asn Gly Leu Tyr Pro Val Ala Asn Asn Arg
                           325                 330                 335

Asn Ala Phe Trp His Cys Val Asn Gly Val Thr Tyr Gln Gln Asn Cys
                       340                 345                 350

Gln Ala Gly Leu Val Phe Asp Thr Ser Cys Asp Cys Cys Asn Trp Ala
                   355                 360                 365

<210> SEQ ID NO 8
<211> LENGTH: 1625
<212> TYPE: DNA
<213> ORGANISM: Homo sapiens

<400> SEQUENCE: 8
gctttccagt ctggtggtga atcctccata gtctgaagcc tttgtgataa ccacagaatc        60
agaacatata aaaagctctg cgggactggt gctgactgca accatgacaa agcttattct       120
cctcacaggt cttgtcctta tactgaattt gcagctcggc tctgcctacc agctgacatg       180
ctacttcacc aactgggccc agtaccggcc aggcctgggg cgcttcatgc ctgacaacat       240 cgaccccctgc ctctgtaccc acctgatcta cgcctttgct gggaggcaga caacgagat       300 caccaccatc gaatgaacg atgtgactct ctaccaagct ttcaatggcc tgaaaaataa       360
gaacagccag ctgaaaactc tcctggccat tggaggctgg aacttcggga ctgcccttt        420 cactgccatg gtttctactc ctgagaaccg ccagactttc atcacctcag tcatcaaatt       480
cctgcgccag tatgagtttg acgggctgga ctttgactgg gagtaccctg gctctcgtgg       540
gagccctcct caggacaagc atctcttcac tgtcctggtg caggaaatgc gtgaagcttt       600
tgagcaggag gccaagcaga tcaacaagcc caggctgatg gtcactgctg cagtagctgc       660
tggcatctcc aatatccagt ctggctatga tcccccaa ctgtcacagt acctggacta        720
catccatgtc atgacctacg acctccatg ctcctgggag ggctacactg agagaacag         780 ccccctctac aaatacccga ctgacaccgg cagcaacgcc tacctcaatg tggattatgt       840
catgaactac tggaaggaca tggagcacc agctgagaag ctcatcgttg gattccctac        900
ctatggacac aacttcatcc tgagcaaccc ctccaacact ggaattggtg cccccacctc       960
tggtgctggt cctgctgggc cctatgccaa ggagtctggg atctgggctt actacgagat      1020
ctgtaccttc ctgaaaaatg gagccactca gggatgggat gccctcagg aagtgcctta      1080 tgcctatcag gcaatgtgt gggttggcta tgacaacatc aagagcttcg atattaaggc       1140
tcaatggctt aagcacaaca atttggagg cgccatggtc tgggcattg atctggatga       1200 cttcactggc actttctgca accagggcaa gtttccccta atctccaccc tgaagaaggc       1260
cctcggcctg cagagtgcaa gttgcacggc tccagctcag cccattgagc caataactgc       1320
tgctcccagt ggcagcggga acgggagcgg gagtagcagc tctggaggca gctcgggagg      1380
cagtggattc tgtgctgtca gagccaacgg cctctacccc gtggcaaata acagaaatgc      1440
cttctggcac tgcgtgaatg gagtcacta ccagcagaac tgccaggccg gcttgtctt        1500 cgacaccagc tgtgattgct gcaactgggc ataaacctga cctggtctat attccctaga      1560
gttccagtct cttttgctta ggacatgttg cccctaccta agtcctgca ataaaatcag        1620 cagtc                                                                1625
```

<210> SEQ ID NO 9
<211> LENGTH: 1530
<212> TYPE: DNA
<213> ORGANISM: Mus musculus

<400> SEQUENCE: 9

| | | | | | |
|---|---|---|---|---|---|
| cgatggccaa | gctacttctc | gtcacaggtc | tggctcttct | gctgaatgct | cagctggggt | 60 |
| ctgcctacaa | tctgatatgc | tatttcacca | actgggccca | gtatcggcca | ggtctgggga | 120 |
| gcttcaagcc | tgatgacatt | aaccctgcc | tgtgtactca | cctgatctat | gcctttgctg | 180 |
| ggatgcagaa | caatgagatc | accaccatag | aatggaatga | tgttactctc | tataaagctt | 240 |
| tcaatgactt | gaaaaacagg | aacagcaaac | tgaaaaccct | cctggcaatt | ggaggctgga | 300 |
| actttggaac | tgctcctttc | actaccatgg | tttccacttc | tcagaaccgc | cagaccttca | 360 |
| ttacctcagt | catcaaattt | ctgcgtcagt | atgggtttga | tggactggac | tggactgggg | 420 |
| aatacccagc | tcacgtggg | agccctcctc | aggacaagca | tctcttcact | gtcctggtga | 480 |
| aggaaatgcg | tgaagctttt | gagcaggagg | ctattgagag | caacaggccc | agactgatgg | 540 |
| ttactgctgc | tgtagctggt | gggatttcca | acatccaggc | tggctatgag | atccctgaac | 600 |
| tttctaagta | cctggatttc | atccatgtca | tgacatatga | cctccatggc | tcctgggagg | 660 |
| gctacactgg | ggagaatagt | cctctttaca | aataccctac | tgagactggt | agcaatgcct | 720 |
| acctcaatgt | ggattatgtc | atgaactatt | ggaagaacaa | tggagcccca | gctgagaagc | 780 |
| tcattgttgg | attcccagag | tatggacaca | ccttcatcct | gagaaacccc | tctgataatg | 840 |
| gaattggtgc | ccctacctct | ggtgatggcc | ctgctggcgc | ctataccaga | caggctgggt | 900 |
| tctgggccta | ctatgagatt | tgcacctttc | tgagaagtgg | agccactgag | gtctgggatg | 960 |
| cctcccaaga | agtgccctat | gcctataagg | ccaacgagtg | gcttggctat | gacaatatca | 1020 |
| agagcttcag | tgttaaggct | cagtggctta | agcagaacaa | ttttgaggt | gccatgatct | 1080 |
| ggccattga | ccttgatgac | ttcactggct | ctttctgtga | tcagggaaaa | tttcctctga | 1140 |
| cttctacttt | gaacaaagcc | cttggcatat | ccactgaagg | ttgcacagct | cctgacgtgc | 1200 |
| cttccgagcc | agtgactact | cctccaggaa | gtgggagtgg | gggtggaagc | tccggaggaa | 1260 |
| gctctggagg | cagtggattc | tgtgccgaca | aagcagatgg | cctctaccct | gtggcagatg | 1320 |
| acagaaatgc | tttttggcag | tgcatcaatg | gaatcacata | ccagcagcat | tgtcaagcag | 1380 |
| ggcttgtttt | tgataccagc | tgtaattgct | gcaactggcc | atgaacctaa | tgccattctt | 1440 |
| ccagaaattt | ctgcactctc | ctttactcct | caccaaaagt | aactatcttc | cctttaacct | 1500 |
| tatgcaataa | aattggtagc | caaaacaaaa | | | | 1530 |

<210> SEQ ID NO 10
<211> LENGTH: 1538
<212> TYPE: DNA
<213> ORGANISM: Mus musculus

<400> SEQUENCE: 10

| | | | | | |
|---|---|---|---|---|---|
| ggccaagcta | cttctcgtca | caggtctggc | tcttctgctg | aatgctcagc | tggggtctgc | 60 |
| ctacaatctg | atatgctatt | tcaccaactg | gcccagtat | cggccaggtc | tggggagctt | 120 |
| caagcctgat | gacattaacc | cctgcctgtg | tactcacctg | atctatgcct | ttgctgggat | 180 |
| gcagaacaat | gagatcacca | ccatagaatg | gaatgatgtt | actctctata | agctttcaa | 240 |
| tgacttgaaa | aacaggaaca | gcaaactgaa | aaccctcctg | gcaattggag | gctggaactt | 300 |
| tggaactgct | cctttcacta | ccatggtttc | cacttctcag | aaccgccaga | ccttcattac | 360 |

```
-continued ctcagtcatc aaatttctgc gtcagtatgg gtttgatgga ctggacctgg actgggaata      420
cccaggctca cgtgggagcc ctcctcagga caagcatctc ttcactgtcc tggtgaagga      480
aatgcgtgaa gcttttgagc aggaggctat tgagagcaac aggcccagac tgatggttac      540
tgctgctgta gctggtggga tttccaacat ccaggctggc tatgagatcc ctgaactttc      600
taagtacctg gatttcatcc atgtcatgac atatgacctc catggctcct gggagggcta      660
cactggggag aatagtcctc tttacaaata ccctactgag actggtagca atgcctacct      720
caatgtggat tatgtcatga actattggaa gaacaatgga gccccagctg agaagctcat      780
tgttggattc ccagagtatg gacacacctt catcctgaga aacccctctg ataatggaat      840
tggtgcccct acctctggtg atggccctgc tgggccctat accagacagg ctgggttctg      900
ggcctactat gagatttgca cctttctgag aagtggagcc actgaggtct gggatgcctc      960
ccaagaagtg ccctatgcct ataaggccaa cgagtggctt ggctatgaca atatcaagag     1020
cttcagtgtt aaggctcagt ggcttaagca gaacaatttt ggaggtgcca tgatctgggc     1080
cattgacctt gatgacttca ctggctcttt ctgtgatcag ggaaaatttc ctctgacttc     1140
tactttgaac aaagcccttg gcatatccac tgaaggttgc acagctcctg acgtgccttc     1200
cgagccagtg actactcctc caggaagtgg gagtgggggt ggaagctccg gaggaagctc     1260
tggaggcagt ggattctgtg ccgacaaagc agatggcctc taccctgtgg cagatgacag     1320
aaatgctttt tggcagtgca tcaatggaat cacataccag cagcattgtc aagcagggct     1380
tgtttttgat accagctgta attgctgcaa ctggccatga acctaatgcc attcttccag     1440
aaatttctgc actctccttt actcctcacc aaaagtaact atcttccctt taaccttatg     1500
caataaaatt ggtagccaaa acaaaaaaaa aaaaaaa                              1538
```